US010969390B2

(12) United States Patent
Sasaki et al.

(10) Patent No.: US 10,969,390 B2
(45) Date of Patent: Apr. 6, 2021

(54) METHOD FOR EVALUATING EFFICACY OF CHEMORADIOTHERAPY AGAINST SQUAMOUS CELL CARCINOMA

(71) Applicants: NATIONAL CANCER CENTER, Tokyo (JP); KYOTO UNIVERSITY, Kyoto (JP); OTSUKA PHARMACEUTICAL CO., LTD., Tokyo (JP)

(72) Inventors: Hiroki Sasaki, Tokyo (JP); Kazuhiko Aoyagi, Tokyo (JP); Manabu Muto, Kyoto (JP); Hiroo Takahashi, Tokyo (JP)

(73) Assignees: NATIONAL CANCER CENTER, Tokyo (JP); KYOTO UNIVERSITY, Kyoto (JP); OTSUKA PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 15/513,707

(22) PCT Filed: Sep. 24, 2015

(86) PCT No.: PCT/JP2015/076927
§ 371 (c)(1),
(2) Date: Mar. 23, 2017

(87) PCT Pub. No.: WO2016/047688
PCT Pub. Date: Mar. 31, 2016

(65) Prior Publication Data
US 2017/0292955 A1  Oct. 12, 2017

(30) Foreign Application Priority Data
Sep. 24, 2014  (JP) .............................. JP2014-194379

(51) Int. Cl.
*C12Q 1/68* (2018.01)
*G01N 33/574* (2006.01)
*C12N 15/79* (2006.01)
*C12Q 1/6806* (2018.01)
*C12Q 1/6853* (2018.01)
*C12Q 1/686* (2018.01)
*C12Q 1/6886* (2018.01)
*C12N 15/09* (2006.01)

(52) U.S. Cl.
CPC .......... *G01N 33/574* (2013.01); *C12N 15/79* (2013.01); *C12Q 1/68* (2013.01); *C12Q 1/6806* (2013.01); *C12Q 1/686* (2013.01); *C12Q 1/6853* (2013.01); *C12Q 1/6886* (2013.01); *C12N 15/09* (2013.01); *C12Q 2600/106* (2013.01); *C12Q 2600/158* (2013.01); *G01N 33/5743* (2013.01)

(58) Field of Classification Search
None
See application file for complete search history.

(56) References Cited

U.S. PATENT DOCUMENTS

| 8,053,183 | B2 * | 11/2011 | Nakamura | ........... C12Q 1/6886 |
| | | | | 435/287.1 |
| 8,211,643 | B2 * | 7/2012 | Tsao | ..................... C12Q 1/6886 |
| | | | | 435/6.12 |
| 8,440,407 | B2 * | 5/2013 | Chudin | ................ C12Q 1/6886 |
| | | | | 435/6.14 |
| 2009/0269772 | A1 * | 10/2009 | Califano | ................ G16C 20/50 |
| | | | | 435/6.16 |
| 2011/0224088 | A1 | 9/2011 | Lyng et al. | |
| 2015/0301058 | A1 * | 10/2015 | Schettini | ................ G01N 33/53 |
| | | | | 424/193.1 |

FOREIGN PATENT DOCUMENTS

| EP | 2 554 994 A1 | 2/2013 | |
| WO | 2004/012847 A1 | 2/2004 | |
| WO | 2010/053717 A1 | 5/2010 | |
| WO | WO-2010065940 A1 * | 6/2010 | ........... C12Q 1/6886 |

OTHER PUBLICATIONS

Ishibashi et al. (Cancer Research, 2003, 63:5159-6164).*
Ishibashi et al. (Cancer Research, 2003, 63:5159-6164) (Year: 2003).*
International Preliminary Report on Patentability, dated Apr. 6, 2017, issued by the International Bureau in International Application No. PCT/JP2015/076927.
Akio Ashida et al., "Expression profiling of esophageal squamous cell carcinoma patients treated with definitive chemoradiotherapy: Clinical implications", International Journal of Oncology, 2006, pp. 1345-1352, vol. 28.
Rajyalakshmi Luthra et al., "Gene Expression Profiling of Localized Esophageal Carcinomas: Association With Pathologic Response to Preoperative Chemoradiation", Journal of Clinical Oncology, Jan. 10, 2006, pp. 259-267, vol. 24, No. 2.
Danielle M. Greenawalt et al., "Gene expression profiling of esophageal cancer: Comparative analysis of Barrett's esophagus, adenocarcinoma, and squamous cell carcinoma", Int. J. Cancer, 2007, pp. 1914-1921, vol. 120.

(Continued)

*Primary Examiner* — Stephanie K Mummert
(74) *Attorney, Agent, or Firm* — Sughrue Mion, PLLC

(57) ABSTRACT

A method for evaluating an efficacy of a chemoradiotherapy against squamous cell carcinoma comprises the following steps (a) to (c):
(a) detecting an expression level of at least one gene selected from a SIM2 gene and genes co-expressed with the SIM2 gene in a squamous cell carcinoma specimen isolated from a subject;
(b) comparing the expression level detected in the step (a) with a reference expression level of the corresponding gene; and
(c) determining that an efficacy of a chemoradiotherapy against squamous cell carcinoma in the subject is high if the expression level in the subject is higher than the reference expression level as a result of the comparison in the step (b).

6 Claims, 14 Drawing Sheets
(1 of 14 Drawing Sheet(s) Filed in Color)
Specification includes a Sequence Listing.

(56) References Cited

OTHER PUBLICATIONS

Cuong Duong et al., "Pretreatment Gene Expression Profiles Can Be Used to Predict Response to Neoadjuvant Chemoradiotherapy in Esophageal Cancer", Annals of Surgical Oncology, 2007, pp. 3602-3609, vol. 14, No. 12.

Stephen G. Maher et al., "Gene Expression Analysis of Diagnostic Biopsies Predicts Pathological Response to Neoadjuvant Chemoradiotherapy of Esophageal Cancer", Annals of Surgery, Nov. 2009, pp. 729-737, vol. 250, No. 5.

Soo Mi Kim et al., "Prognostic Biomarkers for Esophageal Adenocarcinoma Identified by Analysis of Tumor Transcriptome", Plos One, Nov. 2010, pp. 1-8, vol. 5, issue 11.

Hiroki Sasaki et al., "Gene expression-based subtyping of esophageal cancer and personalized medicine", the 12th Annual Meeting of Japanese Society of Medical Oncology, 2014.

J. Wen et al. "Gene expression analysis of pretreatment biopsies predicts the pathological response of esophageal squamous cell carcinomas to neo-chemoradiotherapy", Annals of Oncology, Jun. 6, 2014, pp. 1769-1774, vol. 25, No. 9.

Ju-Sheng An et al., "A preliminary study of genes related to concomitant chemoradiotherapy resistance in advanced uterine cervical squamous cell carcinoma", Chinese Medical Journal, 2013, pp. 4109-4115, vol. 126, No. 21.

International Search Report for PCT/JP2015/076927, dated Dec. 28, 2015.

"Technical Note: Design and Performance of the GeneChip® Human Genome U133 Plus 2.0 and Human Genome U133A 2.0 Arrays", AFFYMETRIX publication, Jan. 1, 2003, pp. 1-9 (total 9 pages).

Ju-Sheng et al., "A preliminary study of genes related to concomitant chemoradiotherapy resistance in advanced uterine cervical squamous cell carcinoma", Chinese Medical Journal, 2013, vol. 126, No. 21, pp. 4109-4115 (total 7 pages).

Wen et al., "Gene expression analysis of pretreatment biopsies predicts the pathological response of esophageal squamous cell carcinomas to neo-chemoradiotherapy", Annals of Oncology, Sep. 2014, vol. 25, No. 9, pp. 1769-1774 (total 6 pages).

Lu et al., "The Role of the Transcription Factor SIM2 in Prostate Cancer", PLOS ONE, Dec. 2011, vol. 6, Issue 12, e28837, pp. 1-10.

Communication, dated Feb. 12, 2018, issued by the European Patent Office in counterpart European Application No. 15843387.0.

* cited by examiner

METHOD FOR EVALUATING EFFICACY OF CHEMORADIOTHERAPY AGAINST SQUAMOUS CELL CARCINOMA

CROSS REFERENCE TO RELATED APPLICATIONS

This application is a National Stage Entry of International Application No. PCT/JP2015/076927 filed Sep. 24, 2015, claiming priority based on Japanese Patent Application No. 2014-194379, filed Sep. 24, 2014, the contents of all of which are incorporated herein by reference in their entirety.

TECHNICAL FIELD

The present invention relates to a method for evaluating an efficacy of a chemoradiotherapy against squamous cell carcinoma, or an agent used in the method.

BACKGROUND ART

Squamous cell carcinoma is malignant basal cells of stratified squamous epithelium and the like, and observed mainly in esophageal cancer, head and neck cancer, cervical cancer, lung cancer, and so forth.

Especially, squamous cell carcinoma accounts for 90% or more cases of esophageal cancer among Mongoloid races in East Asia. Among Caucasian races in Europe and the United States also, squamous cell carcinoma occurs more frequently than adenocarcinoma, which is another esophageal cancer. These two types of the cancer, squamous cell carcinoma and adenocarcinoma, differ from each other in the diseased tissue and the origin. However, the two types of esophageal cancer are treated similarly at present. The standard therapy against locally advanced cancers at the stages of II and III is neoadjuvant chemotherapy (CT) and definitive chemoradiotherapy (CRT) in Japan, while neoadjuvant chemoradiotherapy in Europe and the United States. Definitive CRT results in a five-year survival rate of approximately 50%, which is slightly inferior to that of 55% by neoadjuvant CT. Nevertheless, definitive CRT is capable of organ preservation and is very effective for elderly patients and patients associated also with stomach cancer or head and neck cancer, which accounts for approximately 10% of the esophageal cancer patients. Hence, before a treatment, it is strongly desired to predict and select patients for whom neoadjuvant CRT is effective.

There is a method for evaluating an efficacy of such a therapy against breast cancer, colorectal cancer, and so forth, in which gene expression profiles of biopsies are utilized. Particularly, it has been shown that a subtype classification method is effective.

Efforts have been made to identify clinically useful subtypes of esophageal cancer, too. However, while the number of adenocarcinoma samples is large, the number of squamous cell carcinoma samples analyzed is too small to identify CRT-sensitive subtypes thereof. Further, the disease stages also vary among samples (NPLs 1 to 6. Note that the numbers of esophageal squamous cell carcinoma samples analyzed in NPLs 1 to 6 are respectively 33, 2, 26, 21, 7, and 0). Hence, no reliable results have been obtained which can contribute to predictive medical practice against locally advanced cancers, and a method for predicting chemoradiotherapy sensitivity and prognosis of squamous cell carcinoma has not been developed yet.

CITATION LIST

Non Patent Literatures

[NPL 1] Ashida A. et al., Int J Oncology, 2006, Vol. 28, pp. 1345-1352
[NPL 2] Luthra R. et al., Journal of Clinical Oncology, 2006, Vol. 24, pp. 259-267
[NPL 3] Greenawalt. et al., Int J Cancer, 2007, Vol. 120, pp. 1914-1921
[NPL 4] Duong C. et al., Ann Surg Oncol, 2007, Vol. 14, pp. 3602-3609
[NPL 5] Maher S G. et al., Ann Surg, 2009, Vol. 250, pp. 729-737
[NPL 6] Kim S M. et al., Plos one, 2010, 5: e15074

SUMMARY OF INVENTION

Technical Problem

The present invention has been made in view of the above-described problems of the conventional techniques. An object of the present invention is to provide a method and an agent which enable a high-precision evaluation of an efficacy of a chemoradiotherapy against squamous cell carcinoma (sensitivity and prognosis prediction).

Solution to Problem

In order to achieve the above object, the present inventors conducted an unsupervised cluster analysis based on a comprehensive gene expression profile to identify subtypes correlated with treatment prognoses after a chemoradiotherapy (CRT) against squamous cell carcinoma. As a result, the inventors found out that it was possible to classify, with good reproducibility, squamous cell carcinoma into five case clusters (subtypes) expressing high levels of a particular gene probe set. Moreover, it was revealed that, among the five subtypes, cases belonging to subtype-7 were a good prognosis group, while cases belonging to subtype-5 were a poor prognosis group.

Further, a transcription factor controlling expressions of a gene group expressed at high levels in subtype-7 was searched for by a correlation analysis on expression amounts in each case, so that a SIM2 gene was found. In addition, as a result of the same searching in subtype-5, FOXE1 was found as a transcription factor controlling expressions of a gene group of the subtype. Then, genes defining subtype-7 sensitive to CRT, that is, a SIM2 gene and genes co-expressed with the SIM2 gene (191 genes), were identified. Further, genes defining subtype-5 not sensitive to CRT, that is, a FOXE1 gene and genes co-expressed with the FOXE1 gene (121 genes) were identified.

Additionally, among squamous cell carcinoma cases, cases classified as subtype-7 but not classified as subtype-5 were selected as pure subtype-7. Similarly, cases classified as subtype-5 but not classified as subtype-7 were selected as pure subtype-5. Then, cases belonging to these re-classified pure subtype-7 and pure subtype-5 were analyzed for the post-CRT complete response rates, survival curves, and five-year survival rates. The analysis revealed that it was possible to classify, with a high precision, cases belonging to pure subtype-7 as a good prognosis group and cases belonging to pure subtype-5 as a poor prognosis group. On the other hand, although the same analysis was also conducted on cases who had been subjected to not CRT but surgical resection, no significant difference was found surprisingly in survival rate between the cases belonging to pure subtype-7 and the cases belonging to pure subtype-5. Thus, it was revealed that subtype-5 and subtype-7, or this subtype classification method, were not prognosis factors for predicting surgical resection prognosis but were effective specially in predicting a CRT efficacy.

Meanwhile, the SIM2 gene identified as the gene involved in the CRT sensitivity of squamous cell carcinoma as described above was evaluated for the differentiation-inducing activity. The evaluation revealed that the SIM2 gene was able to induce differentiation of undifferentiated basal cells. Further, it was also found out that introducing the SIM2 gene into squamous cell carcinoma cells promoted the anticancer-agent sensitivity and γ-ray sensitivity of the cancer. It was verified from the viewpoint of the molecular mechanism also that an evaluation of a CRT efficacy against squamous cell carcinoma was possible on the basis of subtype-7 (expressions of the SIM2 gene and the genes co-expressed with the SIM2 gene).

Further, microarray data on esophageal squamous cell carcinoma from China and head and neck squamous cell carcinoma from France were analyzed by the same method as described above. The result verified the presences of subtypes-5 and -7 also in esophageal squamous cell carcinoma in the other country and further in squamous cell carcinoma other than esophageal squamous cell carcinoma (i.e., head and neck squamous cell carcinoma). It was found out that an evaluation of a CRT efficacy against not only esophageal squamous cell carcinoma but also other squamous cell carcinoma was possible on the basis of the expressions of the SIM2 gene and the genes co-expressed with the SIM2 gene as well as the expressions of the FOXE1 gene and the genes co-expressed with the FOXE1 gene.

Furthermore, in order to apply the above-described comprehensive gene expression analysis result to analyses by PCR and the like in which only a limited number of genes were analyzed, a large number of genes (reference genes) whose expression variations were small among squamous cell carcinoma samples were identified successfully. Moreover, based on the expression of an SRSF3 gene determined to be the most useful among these reference genes, the SIM2 gene and the genes co-expressed with the SIM2 gene (191 genes) as well as the FOXE1 gene and the genes co-expressed with the FOXE1 gene (121 genes) were screened for genes which allowed an evaluation of an efficacy of a chemoradiotherapy against squamous cell carcinoma. The result verified that a high-precision evaluation was possible by detecting even one gene in both of the gene groups. Further, it was also verified that detecting at least five genes enabled quite a higher-precision evaluation. In other words, detecting at least five genes among the SIM2 gene and so forth enabled an efficacy determination with a precision equivalent to that achieved by detecting all the 191 genes; meanwhile, detecting at least five genes among the FOXE1 gene and so forth enabled an efficacy determination with a precision equivalent to that achieved by detecting all the 121 genes. These have led to the completion of the present invention.

To be more specific, the present invention relates to a method for evaluating an efficacy of a chemoradiotherapy against squamous cell carcinoma, or an agent used in the method. More specifically, the present invention relates to the following.

(1) A method for evaluating an efficacy of a chemoradiotherapy against squamous cell carcinoma, the method comprising the following steps (a) to (c):

(a) detecting an expression level of at least one gene selected from a SIM2 gene and genes co-expressed with the SIM2 gene in a squamous cell carcinoma specimen isolated from a subject;

(b) comparing the expression level detected in the step (a) with a reference expression level of the corresponding gene; and (c) determining that an efficacy of a chemoradiotherapy against squamous cell carcinoma in the subject is high if the expression level in the subject is higher than the reference expression level as a result of the comparison in the step (b).

(2) A method for evaluating an efficacy of a chemoradiotherapy against squamous cell carcinoma, the method comprising the following steps (a) to (c):

(a) detecting an expression level of at least one gene selected from a SIM2 gene and genes co-expressed with the SIM2 gene as well as an expression level of at least one gene selected from a FOXE1 gene and genes co-expressed with the FOXE1 gene in a squamous cell carcinoma specimen isolated from a subject;

(b) comparing the expression levels detected in the step (a) with reference expression levels of the corresponding genes, respectively; and (c) determining that an efficacy of a chemoradiotherapy against squamous cell carcinoma in the subject is high if the expression level of the at least one gene selected from a SIM2 gene and genes co-expressed with the SIM2 gene in the subject is higher than the reference expression level thereof and the expression level of the at least one gene selected from a FOXE1 gene and genes co-expressed with the FOXE1 gene in the subject is lower than the reference expression level thereof as a result of the comparison in the step (b).

(3) An agent for evaluating an efficacy of a chemoradiotherapy against squamous cell carcinoma by the method according to (1) or (2), the agent comprising at least one compound selected from the following (a) to (d):

(a) an oligonucleotide having a length of at least 15 nucleotides and being capable of hybridizing to a transcription product of at least one gene selected from a SIM2 gene and genes co-expressed with the SIM2 gene or a complementary nucleic acid to the transcription product;

(b) an oligonucleotide having a length of at least nucleotides and being capable of hybridizing to a transcription product of at least one gene selected from a FOXE1 gene and genes co-expressed with the FOXE1 gene or a complementary nucleic acid to the transcription product;

(c) an antibody capable of binding to a translation product of at least one gene selected from a SIM2 gene and genes co-expressed with the SIM2 gene; and (d) an antibody capable of binding to a translation product of at least one gene selected from a FOXE1 gene and genes co-expressed with the FOXE1 gene.

Advantageous Effect of Invention

The present invention enables a high-precision evaluation of an efficacy of a chemoradiotherapy against squamous cell carcinoma.

BRIEF DESCRIPTION OF DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Figure 1:
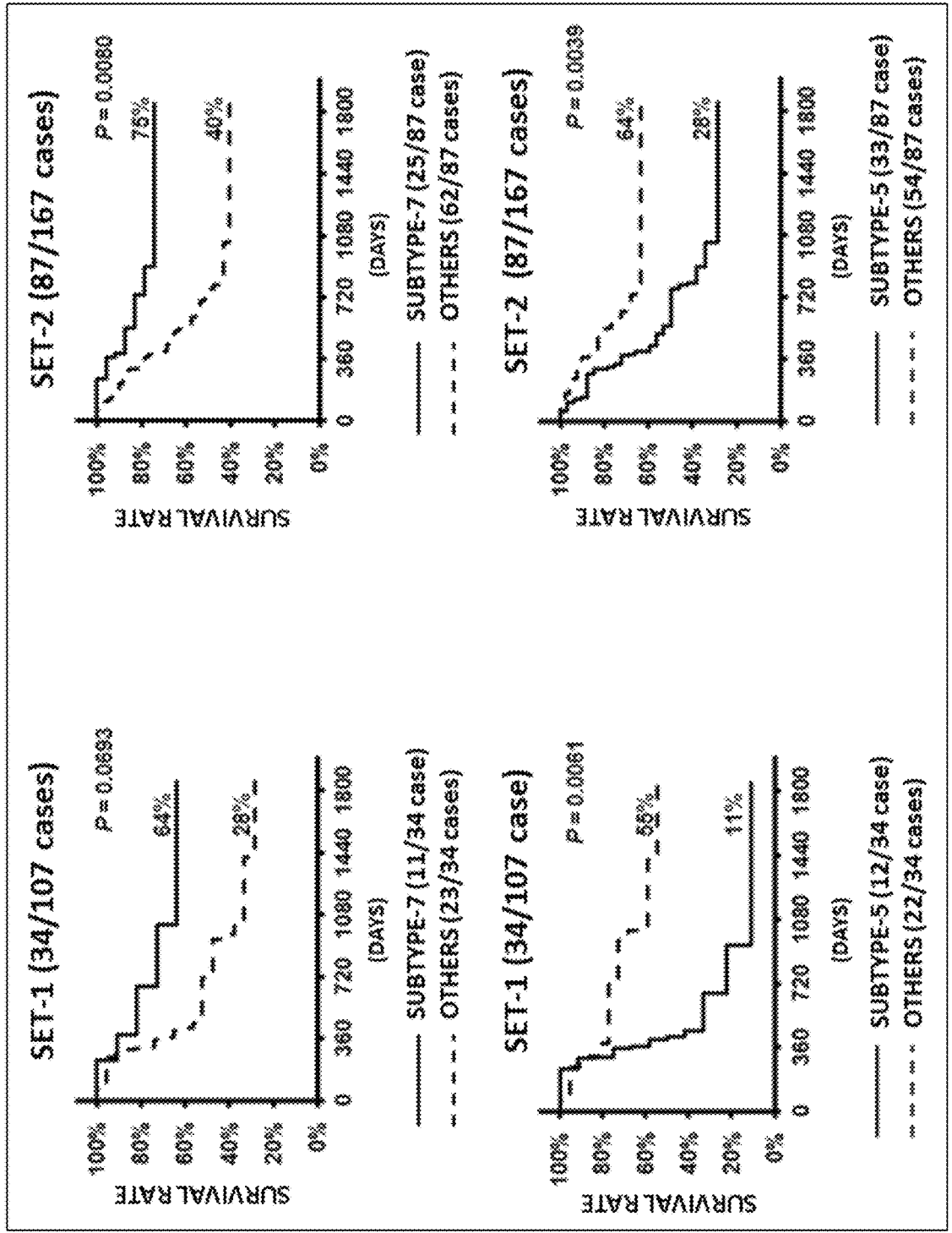
FIG. 1 shows graphs for illustrating the result of an unsupervised cluster analysis based on a comprehensive gene expression profile to identify subtypes correlated with survival rates after a chemoradiotherapy (CRT) against squamous cell carcinoma.

<Method for Evaluating Efficacy of Chemoradiotherapy Against Squamous Cell Carcinoma>

As described later in Examples, an unsupervised cluster analysis based on a comprehensive gene expression profile has been conducted to identify subtypes correlated with treatment prognoses (survival rates) after a chemoradiotherapy against squamous cell carcinoma. The analysis has revealed that a SIM2 gene and genes co-expressed with the SIM2 gene are expressed at high levels in the resulting good prognosis subtype. Thus, the present invention provides a method for evaluating an efficacy of a chemoradiotherapy against squamous cell carcinoma, the method comprising the following steps (a) to (c):

(a) detecting an expression level of at least one gene selected from a SIM2 gene and genes co-expressed with the SIM2 gene in a squamous cell carcinoma specimen isolated from a subject;

(b) comparing the expression level detected in the step (a) with a reference expression level of the corresponding gene; and (c) determining that an efficacy of a chemoradiotherapy against squamous cell carcinoma in the subject is high if the expression level in the subject is higher than the reference expression level as a result of the comparison in the step (b).

Moreover, as described later in Examples, the result of identifying the subtypes correlated with the treatment prognoses after the chemoradiotherapy against squamous cell carcinoma has also revealed that a FOXE1 gene and genes co-expressed with the FOXE1 gene are expressed at high levels in the resulting poor prognosis subtype. Further, it has been found out that it is possible to distinguish a good prognosis group from a poor prognosis group after a chemoradiotherapy with a higher precision on the basis of expressions of the FOXE1 gene and the genes co-expressed with the FOXE1 gene in addition to expressions of the SIM2 gene and the genes co-expressed with the SIM2 gene. Thus, the present invention also provides, as a preferable embodiment thereof, a method for evaluating an efficacy of a chemoradiotherapy against squamous cell carcinoma, the method comprising the following steps (a) to (c):

(a) detecting an expression level of at least one gene selected from a SIM2 gene and genes co-expressed with the SIM2 gene as well as an expression level of at least one gene selected from a FOXE1 gene and genes co-expressed with the FOXE1 gene in a squamous cell carcinoma specimen isolated from a subject;

(b) comparing the expression levels detected in the step (a) with reference expression levels of the corresponding genes, respectively; and (c) determining that an efficacy of a chemoradiotherapy against squamous cell carcinoma in the subject is high if the expression level of the at least one gene selected from a SIM2 gene and genes co-expressed with the SIM2 gene in the subject is higher than the reference expression level thereof and the expression level of the at least one gene selected from a FOXE1 gene and genes co-expressed with the FOXE1 gene in the subject is lower than the reference expression level thereof as a result of the comparison in the step (b).

In the present invention, the term "squamous cell carcinoma" is not particularly limited, as long as it is malignant basal cells of stratified squamous epithelium and the like. Examples thereof include squamous cell carcinomas in: digestive organs such as esophagus (upper esophagus, middle esophagus, lower esophagus) and rectum; head and neck parts such as nasal cavity, maxilla, maxillary sinus, tongue, floor of mouth, gingiva, buccal mucosa, epipharynx, mesopharynx, hypopharynx, and larynx; lung, anus, vulva, vagina, and cervix. The target in the present invention to be evaluated for a chemoradiotherapy efficacy is preferably esophageal squamous cell carcinoma and head and neck squamous cell carcinoma, and more preferably esophageal squamous cell carcinoma.

The "chemoradiotherapy" is a combination therapy of both of a "chemotherapy" through anticancer agent administration or the like and a "radiotherapy" through radiation irradiation. In the present invention, the "chemoradiotherapy" may be a therapy performed only by itself, a preoperative chemoradiotherapy performed before an operation, a postoperative chemoradiotherapy performed after an operation, or a chemoradiotherapy performed in combination with another therapy other than an operation. In the chemotherapy, the type of the anticancer agent is not particularly limited, as long as the anticancer agent is well known to those skilled in the art. Examples of the anticancer agent include platinum preparations such as cisplatin (CDDP), carboplatin, oxaliplatin, and nedaplatin; antimetabolites such as 5-fluorouracil (5-FU), tegafur-uracil, TS-1 (containing tegafur, gimeracil, and oteracil potassium), methotrexate, and gemcitabine hydrochloride; plant alkaloids such as docetaxel (DTX) and irinotecan; alkylating agents such as cyclophosphamide, melphalan, ranimustine, nimustine, and temozolomide; anticancer antibiotics such as doxorubicin; and biological response modifiers such as interferon-α. The administration amount, administration schedule, and so forth of the anticancer agent are selected depending on the type of the anticancer agent and the condition of a subject. Multiple types of anticancer agents may be co-administered. In the radiotherapy, the type of the radiation (for example, γ ray, X-ray, electron beam, proton beam, heavy particle beam), radiation intensity, irradiation time, and so forth are not particularly limited, as long as these are within ranges normally adopted in cancer therapies.

In the present invention, examples of the "efficacy of a chemoradiotherapy against squamous cell carcinoma" include a survival rate and a complete response rate of subjects after a treatment by the chemoradiotherapy (prognosis). To be more specific, the phrase that the efficacy is high means the survival rate is high; more concretely, the survival rate is 50% or higher when five years (1800 days) elapse after a treatment by the chemoradiotherapy. On the other hand, the phrase that the efficacy is low means the survival rate is low; more concretely, the survival rate is lower than 50% when five years elapse after a treatment by the chemoradiotherapy (see FIGS. 1, 2, and 4 to be described later). Meanwhile, the high efficacy also means that the complete response rate is high; more concretely, the complete response rate is 50% or higher two to three months after a treatment by the chemoradiotherapy. On the other hand, the low efficacy also means that the complete response rate is low; more concretely, the complete response rate is lower than 50% two to three months after a treatment by the chemoradiotherapy (see Table 15 to be described later).

In the present invention, a "subject" may be not only a squamous cell carcinoma patient before a treatment by the chemoradiotherapy, but also a squamous cell carcinoma patient during a treatment by the chemoradiotherapy, or a squamous cell carcinoma patient after a treatment by the chemoradiotherapy. Moreover, examples of the "subject" according to the present invention include not only human who has squamous cell carcinoma, but also human who has been subjected to a therapy to remove squamous cell carcinoma but may have a relapse.

A "squamous cell carcinoma specimen isolated from a subject" should be squamous cell carcinoma excised from a subject (human body) and completely isolated from the body from which the squamous cell carcinoma is originated, or a tissue containing such squamous cell carcinoma. Examples thereof include tissues (biopsy samples) containing squamous cell carcinoma sampled from subjects for a test before a treatment is started, and tissues containing squamous cell carcinoma excised by an operation. The "squamous cell carcinoma specimen isolated from a subject" is more preferably biopsy samples. In addition, the timing at which a "squamous cell carcinoma specimen" is isolated from a subject is not particularly limited, but is preferably a timing at which no distant metastasis of the cancer is observed (disease stages: II, III).

The "SIM2 gene" whose expression level is to be detected in the present invention is a gene also called single-minded homolog 2 (*Drosophila melanogaster*), single-minded family bHLH transcription factor 2, SIM, bHLHe15, HMC13F06, or HMC29C01. If derived from human, the SIM2 gene is typically a gene specified under Entrez Gene ID: 6493 (gene having the DNA sequence specified under Ref Seq ID: NM_005069, gene encoding a protein having the amino acid sequence specified under Ref Seq ID: NP_005060).

Moreover, the "genes co-expressed with the SIM2 gene" whose expression levels are to be detected in the present invention are genes whose expressions vary in correlation with the expression of the SIM2 gene (the genes exhibit expression patterns similar to that of the SIM2 gene). Those skilled in the art can judge whether or not the gene expressions of these genes and the SIM2 gene are highly correlated with each other by an analysis employing a method known in the technical field. For example, the judgment is possible by calculating a Pearson correlation coefficient or a Spearman correlation coefficient of gene expression amounts among samples (such as squamous cell carcinoma specimens described above), or the calculation is possible by a clustering method. Alternatively, the co-expression can also be analyzed through a calculation using normalized expression data or standardized and normalized expression data. In the present invention, the "genes co-expressed with the SIM2 gene" are preferably genes correlated with the expression of the SIM2 gene with a Pearson product-moment correlation coefficient of 0.4 or more. Moreover, more preferable examples of the "SIM2 gene and genes co-expressed with the SIM2 gene" include 191 genes shown in the following Tables 1 to 7. Furthermore preferable examples of the genes include 69 genes shown in Table 36 to be described later.

TABLE 1

| ID | Gene name | Gene symbol |
|---|---|---|
| 144568 | alpha-2-macroglobulin-like 1 | A2ML1 |
| 55 | acid phosphatase, prostate | ACPP |
| 83543 | allograft inflammatory factor 1-like | AIF1L |
| 202 | absent in melanoma 1 | AIM1 |
| 391267 | ankyrin repeat domain 20 family, member A11, pseudogene | ANKRD20A11P |
| 148741 | ankyrin repeat domain 35 | ANKRD35 |
| 301 | annexin A1 | ANXA1 |
| 8416 | annexin A9 | ANXA9 |
| 360 | aquaporin 3 (Gill blood group) | AQP3 |
| 9743 | Rho GTPase activating protein 32 | ARHGAP32 |
| 23120 | ATPase, class V, type 10B | ATP10B |
| 84239 | ATPase type 13A4 | ATP13A4 |
| 8424 | butyrobetaine (gamma), 2-oxoglutarate dioxygenase (gamma-butyrobetaine hydroxylase) 1 | BBOX1 |
| 29760 | B-cell linker | BLNK |
| 149428 | BCL2/adenovirus E1B 19 kD interacting protein like | BNIPL |
| 54836 | B-box and SPRY domain containing | BSPRY |
| 84419 | chromosome 15 open reading frame 48 | C15orf48 |
| 643008 | chromosome 17 open reading frame 109 | C17orf109 |
| 79098 | chromosome 1 open reading frame 116 | C1orf116 |
| 163747 | chromosome 1 open reading frame 177 | C1orf177 |
| 54094 | chromosome 21 open reading frame 15 | C21orf15 |
| 79919 | chromosome 2 open reading frame 54 | C2orf54 |
| 375791 | chromosome 9 open reading frame 169 | C9orf169 |
| 81617 | calcium binding protein 39-like | CAB39L |
| 440854 | calpain 14 | CAPN14 |
| 726 | calpain 5 | CAPN5 |
| 100133941 | CD24 molecule | CD24 |
| 1030 | cyclin-dependent kinase inhibitor 2B (p15, inhibits CDK4) | CDKN2B |
| 634 | carcinoembryonic antigen-related cell adhesion molecule 1 (biliary glycoprotein) | CEACAM1 |

TABLE 2

| ID | Gene name | Gene symbol |
|---|---|---|
| 1048 | carcinoembryonic antigen-related cell adhesion molecule 5 | CEACAM5 |
| 4680 | carcinoembryonic antigen-related cell adhesion molecule 6 (non-specific cross reacting antigen) | CEACAM6 |
| 1087 | carcinoembryonic antigen-related cell adhesion molecule 7 | CEACAM7 |
| 8824 | carboxylesterase 2 | CES2 |
| 84952 | cingulin-like 1 | CGNL1 |
| 10752 | cell adhesion, molecule with homology to L1CAM (close homolog of L1) | CHL1 |
| 22802 | chloride channel accessory 4 | CLCA4 |
| 9022 | chloride intracellular channel 3 | CLIC3 |
| 23242 | cordon-bleu homolog (mouse) | COBL |
| 22849 | cytoplasmic polyadenylation element binding protein 3 | CPEB3 |
| 1382 | cellular retinoic acid binding protein 2 | CRABP2 |
| 10321 | cysteine-rich secretory protein 3 | CRISP3 |
| 49860 | cornulin | CRNN |
| 1476 | cystatin B (stefin B) | CSTB |
| 83992 | cortactin binding protein 2 | CTTNBP2 |
| 284340 | chemokine (C—X—C motif) ligand 17 | CXCL17 |
| 3579 | chemokine (C—X—C motif) receptor 2 | CXCR2 |
| 1562 | cytochrome P450, family 2, subfamily C, polypeptide 18 | CYP2C18 |
| 1559 | cytochrome P450, family 2, subfamily C, polypeptide 9 | CYP2C9 |
| 1571 | cytochrome P450, family 2, subfamily E, polypeptide 1 | CYP2E1 |
| 1573 | cytochrome P450, family 2, subfamily J, polypeptide 2 | CYP2J2 |
| 1577 | cytochrome P450, family 3, subfamily A, polypeptide 5 | CYP3A5 |
| 100861540 | CYP3A7-CYP3AP1 readthrough | CYP3A7-CYP3AP1 |
| 1580 | cytochrome P450, family 4, subfamily B, polypeptide 1 | CYP4B1 |
| 66002 | cytochrome P450, family 4, subfamily F, polypeptide 12 | CYP4F12 |
| 1734 | deiodinase, iodothyronine, type II | DIO2 |
| 50506 | dual oxidase 2 | DUOX2 |
| 6990 | dynein, light chain, Tctex-type 3 | DYNLT3 |
| 1893 | extracellular matrix protein 1 | ECM1 |
| 30845 | EH-domain containing 3 | EHD3 |

TABLE 3

| ID | Gene name | Gene symbol |
|---|---|---|
| 26298 | ets homologous factor | EHF |
| 79071 | ELOVL fatty acid elongase 6 | ELOVL6 |
| 2012 | epithelial membrane protein 1 | EMP1 |
| 8909 | endonuclease, polyU-specific | ENDOU |
| 23136 | erythrocyte membrane protein band 4.1-like 3 | EPB41L3 |
| 64097 | erythrocyte membrane protein band 4.1 like 4A | EPB41L4A |
| 54869 | EPS8-like 1 | EPS8L1 |
| 121506 | endoplasmic reticulum protein 27 | ERP27 |
| 2139 | eyes absent homolog 2 (*Drosophila*) | EYA2 |
| 9413 | family with sequence similarity 189, member A2 | FAM189A2 |
| 54097 | family with sequence similarity 3, member B | FAM3B |
| 131177 | family with sequence similarity 3, member D | FAM3D |
| 151354 | family with sequence similarity 84, member A | FAM84A |
| 2327 | flavin containing monooxygenase 2 (non-functional) | FMO2 |
| 2525 | fucosyltransferase 3 (galactoside 3(4)-L-fucosyltransferase, Lewis blood group) | FUT3 |
| 2528 | fucosyltransferase 6 (alpha (1,3) fucosyltransferase) | FUT6 |
| 79695 | UDP-N-acetyl-alpha-D-galactosamine:polypeptide N-acetylgalactosaminyltransfersse 12 (GalNAc-T12) | GALNT12 |
| 11227 | UDP-N-acetyl-alpha-D-galactosamine:polypeptide N-acetylgalactosaminyltransferase 5 (GalNAc-T5) | GALNT5 |
| 8484 | galanin receptor 3 | GALR3 |
| 8522 | growth arrest-specific 7 | GAS7 |
| 163351 | guanylate binding protein family, member 6 | GBP6 |
| 79153 | glycerophosphodiester phosphodiesterase domain containing 3 | GDPD3 |
| 124975 | gamma-glutamyltransferase 6 | GGT6 |
| 2681 | glycoprotein, alpha-galactosyltransferase 1 pseudogene | GGTA1P |
| 23171 | glycerol-3-phosphate dehydrogenase 1-like | GPD1L |
| 266977 | G protein-coupled receptor 110 | GPR110 |
| 84525 | HOP homeobox | HOPX |
| 3248 | hydroxyprostaglandin dehydrogenase 15-(NAD) | HPGD |
| 9957 | heparan sulfate (glucosamine) 3-O-sulfotransferase 1 | HS3ST1 |

TABLE 4

| ID | Gene name | Gene symbol |
|---|---|---|
| 22807 | IKAROS family zinc finger 2 (Helios) | IKZF2 |
| 3557 | interlenkin 1 receptor antagonist | IL1RN |
| 90865 | interleukin 33 | IL33 |
| 27179 | interleukin 36, alpha | IL36A |
| 3695 | integrin, beta 7 | ITGB7 |
| 8850 | K(lysine) acetyltransferase 2B | KAT2B |
| 152831 | klotho beta | KLB |
| 11279 | Kruppel-like factor 8 | KLF8 |
| 43849 | kallikrein-related peptidase 12 | KLK12 |
| 26085 | kallikrein-related peptidase 13 | KLK13 |
| 3860 | keratin 13 | KRT13 |
| 192666 | keratin 24 | KRT24 |
| 3851 | Keratin 4 | KRT4 |
| 196374 | keratin 78 | KRT78 |
| 4008 | LIM domain 7 | LMO7 |
| 84708 | ligand of numb-protein X 1, E3 ubiquitin protein ligase | LNX1 |
| 283278 | uncharacterized LOC283278 | LOC283278 |
| 441178 | uncharacterized LOC441178 | LOC441178 |
| 10161 | lysophosphatidic acid receptor 6 | LPAR6 |
| 4033 | lymphoid-restricted membrane protein | LRMP |
| 120892 | leucine-rich repeat kinase 2 | LRRK2 |
| 66004 | Ly6/neurotoxin 1 | LYNX1 |
| 126868 | mab-21-like 3 (*C. elegans*) | MAB21L3 |
| 346389 | metastasis associated in colon cancer 1 | MACC1 |
| 4118 | mal, T-cell differentiation protein | MAL |
| 55534 | mastermind-like 3 (*Drosophila*) | MAML3 |
| 54682 | MANSC domain containing 1 | MANSC1 |
| 11343 | monoglyceride lipase | MGLL |
| 143098 | membrane protein, palmitoylated 7 (MAGUK p55 subfamily member 7) | MPP7 |
| 10205 | myelin protein zero-like 2 | MPZL2 |
| 143662 | mucin 15, cell surface associated | MUC15 |
| 10529 | nebulette | NEBL |

TABLE 5

| ID | Gene name | Gene symbol |
|---|---|---|
| 10874 | neuromedin U | NMU |
| 4948 | oculocutaneous albinism II | OCA2 |
| 10819 | olfactory receptor, family 7, subfamily E, member 14 pseudogene | OR7E14P |
| 29943 | peptidyl arginine deiminase, type I | PADI1 |
| 5083 | paired box 9 | PAX9 |
| 5307 | paired-like homeodomain 1 | PITX1 |
| 5569 | protein kinase (cAMP-dependent, catalytic) inhibitor alpha | PKIA |
| 51316 | placenta-specific 8 | PLAC8 |
| 144100 | pleckstrin homology domain containing, family A member 7 | PLEKHA7 |
| 5493 | periplakin | PPL |
| 5507 | protein phosphatase 1, regulatory subunit 3C | PPP1R3C |
| 5645 | protease, serine, 2 (trypain 2) | PRSS2 |
| 83886 | protease, serine 27 | PRSS27 |
| 8000 | prostate stem cell antigen | PSCA |
| 5753 | PTK6 protein tyrosine kinase 6 | PTK6 |
| 57111 | RAB25, member RAS oncogene family | RAB25 |
| 5874 | KAB27B, member RAS oncogene family | RAB27B |
| 10125 | RAS guanyl releasing protein 1 (calcium and DAG-regulated) | RASGRP1 |
| 51458 | Rh family, C glycoprotein | RHCG |
| 54101 | receptor-interacting serine-threonine kinase 4 | RIPK4 |
| 138065 | ring finger protein 183 | RNF183 |
| 58528 | Ras-related GTP binding D | RRAGD |
| 57402 | S100 calcium binding protein A14 | S100A14 |
| 23328 | SAM and SH3 domain containing 1 | SASH1 |
| 8796 | sciellin | SCEL |
| 6337 | sodium channel, non-voltage-gated 1 alpha subunit | SCNN1A |
| 6338 | sodium channel, non-voltage-gated 1, beta subunit | SCNN1B |
| 1992 | serpin peptidase inhibitor, clade B (ovalbumin), member 1 | SERPINB1 |

TABLE 5-continued

| ID | Gene name | Gene symbol |
|---|---|---|
| 89778 | serpin peptidase inhibitor, clade B (ovalbumin), member 11 (gene/pseudogene) | SERPINB11 |
| 5275 | serpin peptidase inhibitor, clade B (ovalbumin), member 13 | SERPINB13 |

TABLE 6

| ID | Gene name | Gene symbol |
|---|---|---|
| 389376 | surfactant associated 2 | SFTA2 |
| 83699 | SH3 domain binding glutamic acid-rich protein like 2 | SHSBGRL2 |
| 57619 | shroom family member 3 | SHROOM3 |
| 6493 | single-minded homolog 2 (*Drosophila*) | SIM2 |
| 26266 | solute carrier family 13 (sodium/sulfate symporters), member 4 | SLC13A4 |
| 9120 | solute carrier family 16, member 6 (monocarboxylic acid transporter 7) | SLC16A6 |
| 9194 | solute carrier family 16, member 7 (monocarboxylic acid transporter 2) | SLC16A7 |
| 57152 | secreted LY6/PLAUR domain containing 1 | SLURP1 |
| 57228 | small cell adhesion glycoprotein | SMAGP |
| 26780 | small nucleolar RNA, H/ACA box 68 | SNORA68 |
| 6272 | sortilin 1 | SORT1 |
| 200162 | sperm associated antigen 17 | SPAG17 |
| 132671 | spermatogenesis associated 18 | SPATA18 |
| 11005 | serine peptidase inhibitor, Kazal type 5 | SPINK5 |
| 84651 | serine peptidase inhibitor, Kazal type 7 (putative) | SPINK7 |
| 6698 | small proline-rich protein 1A | SPRR1A |
| 6702 | small proline-rich protein 2C (pseudogene) | SPRR2C |
| 6707 | small proline-rich protein 3 | SPRR3 |
| 55806 | ST6 (alpha-N-acetyl-neuraminyl-2,3-beta-galactosyl-1,3)-N-acetylgalactosaminide alpha-2,6-sialyltransferase 1 | ST6GALNAC1 |
| 415117 | syntaxin 19 | STX19 |
| 258010 | small VCP/p97-interacting protein | SVIP |
| 94122 | synaptotsgmin-like 5 | SYTL5 |
| 7051 | transglutaminase 1 (K polypeptide epidermal type I, protein-glutamine-gamma-glutamyltransferase) | TGM1 |
| 7053 | transglutaminase 3 (E polypeptide, protein-glutamine-gamma-glutamyltransferase) | TGM3 |
| 79875 | thrombospondin, type I, domain containing 4 | THSD4 |
| 120224 | transmembrane protein 45B | TMEM45B |

TABLE 7

| ID | Gene name | Gene symbol |
|---|---|---|
| 132724 | transmembrane protease, serine 11B | TMPRSS11B |
| 9407 | transmembrane protease, serine 11D | TMPRSS11D |
| 28983 | transmembrane protease, serine 11E | TMPRSS11E |
| 7113 | transmembrane protease, serine 2 | TMPRSS2 |
| 9540 | tumor protein p53 inducible protein 3 | TP53I3 |
| 388610 | TMF1-regulated nuclear protein 1 | TRNP1 |
| 22996 | tetratricopeptide repeat domain 39A | TTC39A |
| 23508 | tetratricopeptide repeat domain 9 | TTC9 |
| 11045 | uroplakin 1A | UPK1A |
| 10451 | vav 3 guanine nucleotide exchange factor | VAV3 |
| 147645 | V-set and immunoglobulin domain containing 10 like | VSIG10L |
| 7504 | X-linked Kx blood group (McLeod syndrome) | XK |
| 340481 | zinc finger, DHHC-type containing 21 | ZDHHC21 |
| 7739 | zinc finger protein 185 (LIM domain) | ZNF185 |
| 284391 | zinc finger protein 844 | ZNF844 |

The "FOXE1 gene" whose expression level is to be detected in the present invention is a gene also called forkhead box E1 (thyroid transcription factor 2), TTF2, FOXE2, HFKH4, HFKL5, TITF2, TTF-2, or FKHL15. If derived from human, the FOXE1 gene is typically a gene specified under Entrez Gene ID: 2304 (gene having the DNA sequence specified under Ref Seq ID: NM_004473, gene encoding a protein having the amino acid sequence specified under Ref Seq ID: NP_004464).

Moreover, the "genes co-expressed with the FOXE1 gene" whose expression levels are to be detected in the present invention are, as in the case of the above-described SIM2 gene, genes whose expressions vary in correlation with the expression of the FOXE1 gene (the genes exhibit expression patterns similar to that of the FOXE1 gene). Whether or not the gene expressions of these genes and the FOXE1 gene are highly correlated with each other can also be judged by the same analysis method as that for the above-described SIM2 gene. In the present invention, the "genes co-expressed with the FOXE1 gene" are preferably genes correlated with the expression of the FOXE1 gene with a Pearson product-moment correlation coefficient of 0.4 or more. Moreover, more preferable examples of the "FOXE1 gene and genes co-expressed with the FOXE1 gene" include 121 genes shown in the following Tables 8 to 12. Furthermore preferable examples of the genes include 56 genes shown in Table 35 to be described later.

TABLE 8

| ID | Gene name | Gene symbol |
|---|---|---|
| 344752 | arylacetamide deacetylase-like 2 | AADACL2 |
| 154664 | ATP-binding cassette, sub-family A (ABC1), member 13 | ABCA13 |
| 10058 | ATP-binding cassette, sub-family B (MDR/TAP), member 6 | ABCB6 |
| 4363 | ATP-binding cassette, sub-family C (CFTR/MRP), member 1 | ABCC1 |
| 10057 | ATP-binding cassette, sub-family C (CFTR/MRP), member 5 | ABCC5 |
| 8745 | ADAM metallopeptidase domain 23 | ADAM23 |
| 131 | alcohol dehydrogenase 7 (class IV), mu or sigma polypeptide | ADH7 |
| 84803 | 1-acylglycerol-3-phosphate O-acyltransferase 9 | AGPAT9 |
| 57016 | aldo-keto reductase family 1, member B10 (aldose reductase) | AKR1B10 |
| 1645 | aldo-keto reductase family 1, member C1 (dihydrodiol dehydrogenase 1; 20-alpha (3-alpha)-hydroxysteroid dehydrogenase) | AKR1C1 |
| 8644 | aldo-keto reductase family 1, member C3 (3-alpha hydroxysteroid dehydrogenase, type II) | AKR1C3 |
| 214 | activated leukocyte cell adhesion molecule | ALCAM |
| 216 | aldehyde dehydrogenase 1 family, member A1 | ALDH1A1 |
| 218 | aldehyde dehydrogenase 3 family, member A1 | ALDH3A1 |
| 26084 | Rho guanine nucleotide exchange factor (GEF) 26 | ARHGEF26 |
| 100507524 | ARHGEF26 antisense RNA 1 (non-protein coding) | ARHGEF26-AS1 |
| 8702 | UDP-Gal:betaGlcNAc beta 1,4-galactosyltransferase, polypeptide 4 | B4GALT4 |

TABLE 8-continued

| ID | Gene name | Gene symbol |
| --- | --- | --- |
| 627 | brain-derived neurotrophic factor | BDNF |
| 205428 | chromosome 3 open reading frame 58 | C3orf58 |
| 29113 | chromosome 6 open reading frame 15 | C6orf15 |
| 774 | calcium channel, voltage-dependent, N type, alpha 1B sabunit | CACNA1B |
| 793 | calbindin 1, 28 kDa | CALB1 |
| 873 | carbonyl reductase 1 | CBR1 |

TABLE 9

| ID | Gene name | Gene symbol |
| --- | --- | --- |
| 10344 | chemokine (C—C motif) ligand 26 | CCL26 |
| 60437 | cadherin 26 | CDH26 |
| 55755 | CDK5 regulatory subunit associated protein 2 | CDK5RAP2 |
| 140578 | chondrolectin | CHODL |
| 56548 | carbohydrate (N-acetylglucosamine 6-O) sulfotransferase 7 | CHST7 |
| 49861 | claudin 20 | CLDN20 |
| 26047 | contactin associated protein-like 2 | CNTNAP2 |
| 1400 | collapsin response mediator protein 1 | CRMP1 |
| 57007 | chemokine (C—X—C motif) receptor 7 | CXCR7 |
| 1592 | cytochrome P450, family 26, subfamily A, polypeptide 1 | CYP26A1 |
| 29785 | cytochrome P450, family 2, subfamily S, polypeptide 1 | CYP2S1 |
| 57834 | cytochrome P450, family 4, subfamily F, polypeptide 11 | CYP4F11 |
| 4051 | cytochrome P450, family 4, subfamily F, polypeptide 3 | CYP4F3 |
| 1749 | distal-less homeobox 5 | DLX5 |
| 10655 | doublesex and mab-3 related transcription factor 2 | DMRT2 |
| 956 | ectonucleoside triphosphate diphosphohydrolase 3 | ENTPD3 |
| 84553 | failed axon connections homolog (*Drosophila*) | FAXC |
| 2263 | fibroblast growth factor receptor 2 | FGFR2 |
| 80078 | uncharacterized FLJ13744 | FLJ13744 |
| 2304 | forkhead box E1 (thyroid transcription factor 2) | FOXE1 |
| 11211 | frizzled family receptor 10 | FZD10 |
| 8324 | frizzled family receptor 7 | FZD7 |
| 2539 | glusose-6-phosphate dehydrogenase | G6PD |
| 2729 | glutamate-cysteine ligase, catalytic subunit | GCLC |
| 2730 | glutamate-cysteine ligase, modifier subunit | GCLM |
| 9615 | guanine deaminase | GDA |
| 2736 | GLI family zinc finger 2 | GLI2 |
| 23127 | glycosyltransferase 25 domain containing 2 | GLT25D2 |
| 2719 | glypican 3 | GPC3 |
| 2877 | glutathione peroxidase 2 (gastrointestinal) | GPX2 |
| 2936 | glutathione reductase | GSR |
| 2938 | glutathione S-transferase alpha 1 | GSTA1 |
| 2944 | glutathione S-transferase mu 1 | GSTM1 |

TABLE 10

| ID | Gene name | Gene symbol |
| --- | --- | --- |
| 2946 | glutathione S-transferase mu 2 (muscle) | GSTM2 |
| 2947 | glutathione S-transferase mu 3 (brain) | GSTM3 |
| 9832 | janus kinase and microtubule interacting protein 2 | JAKMIP2 |
| 282973 | Janus kinase and microtubule interacting protein 3 | JAKMIP3 |
| 3790 | potassium voltage-gated channel, delayed-rectifier, subfamily S, member 3 | KCNS3 |
| 57535 | KIAA1324 | KIAA1324 |
| 346689 | killer cell lectin-like receptor subfamily G, member 2 | KLRG2 |
| 100505633 | uncharacterized LOC100505633 | LOC100505633 |
| 338240 | keratin 17 pseudogene | LOC339240 |
| 344887 | NmrA-like family domain containing 1 pseudogene | LOC344887 |
| 54886 | lipid phosphate phosphatase-related protein type 1 | LPPR1 |
| 64101 | leucine rich repeat containing 4 | LRRC4 |
| 4199 | malic enzyme 1, NADP(+)-dependent, cytosolic | ME1 |
| 10461 | c-mer proto-oncogene tyrosine kinase | MERTK |
| 4356 | membrane protein, palmitoylated 3 (MAGUK p55 subfamily member 3) | MPP3 |
| 112609 | melanocortin 2 receptor accessory protein 2 | MRAP2 |
| 23327 | neural precursor cell expressed, developmentally down-regulated 4-like, E3 ubiquitin protein ligase | NEDD4L |
| 4842 | nitric oxide synthase 1 (neuronal) | NOS1 |
| 4897 | neuronal cell adhesion molecule | NRCAM |
| 4915 | neurotrophic tyrosine kinase, receptor, type 2 | NTRK2 |
| 4922 | neurotensin | NTS |
| 26011 | odz, odd Oz/ten-m homolog 4 (*Drosophila*) | ODZ4 |
| 10439 | olfactomedin 1 | OLFM1 |
| 29948 | oxidative stress induced growth inhibitor 1 | OSGIN1 |
| 57144 | p21 protein (Cdc42/Rac)-activated kinase 7 | PAK7 |
| 79605 | piggyBac transposable element derived 5 | PGBD5 |
| 8544 | pirin (iron-binding nuclear protein) | PIR |
| 5521 | protein phosphatase 2, regulatory subunit B, beta | PPP2R2B |
| 5613 | protein kinase, X-linked | PRKX |
| 23362 | pleckstrin and Sec7 domain containing 3 | PSD3 |

TABLE 11

| ID | Gene name | Gene symbol |
|---|---|---|
| 22949 | prostaglandin reductase 1 | PTGR1 |
| 5802 | protein, tyrosine phosphatase, receptor type, S | PTPRS |
| 5865 | RAB3B, member RAS oncogene family | RAB3B |
| 51560 | RAB6B, member RAS oncogene family | RAB6B |
| 9182 | Ras association (RalGDS/AF-6) domain family (N-terminal) member 9 | RASSF9 |
| 6016 | Ras-like without CAAX 1 | RIT1 |
| 401474 | Sterile alpha motif domain containing 12 | SAMD12 |
| 6335 | sodium channel voltage-gated, type IX, alpha subunit | SCN9A |
| 221935 | sidekick cell adhesion molecule 1 | SDK1 |
| S0031 | sema domain, transmembrane domain (TM), and cytoplasmic domain, (semaphorin) 6D | SEMA6D |
| 143686 | sestrin 3 | SESN3 |
| 57568 | signal-induced proliferation-associated 1 like 2 | SIPA1L2 |
| 151473 | solute carrier family 16, member 14 (monocarboxylic acid transporter 14) | SLC16A14 |
| 159371 | solute carrier family 35, member G1 | SLC35G1 |
| 55244 | solute carrier family 47, member 1 | SLC47A1 |
| 83959 | solute carrier family 4, sodium borate transporter, member 11 | SLC4A11 |
| 23657 | solute carrier family 7 (anionic amino acid transporter light chain, xc-system), member 11 | SLC7A11 |
| 23428 | solute carrier family 7 (amino acid transporter light chain, L system), member 8 | SLC7A8 |
| 285195 | solute carrier family 9, subfamily A (NHE9, cation proton antiporter 9), member 9 | SLC9A9 |
| 28232 | solute carrier organic anion transporter family, member 3A1 | SLCO3A1 |
| 50964 | sclerostin | SOST |
| 6657 | SRY (sex determining region Y)-box 2 | SOX2 |
| 347689 | SOX2 overlapping transcript (non-protein coding) | SOX2-OT |
| 140809 | sulfiredoxin 1 | SRXN1 |
| 54879 | Suppression of tumorigenicity 7 like | ST7L |
| 55061 | sushi domain containing 4 | SUSD4 |

TABLE 12

| ID | Gene name | Gene symbol |
|---|---|---|
| 89894 | transmembrane protein 116 | TMEM116 |
| 56649 | transmembrane protease, serine 4 | TMFRSS4 |
| 83857 | transmembrane and tetratricopeptide repeat containing 1 | TMTC1 |
| 7102 | tetraspanin 7 | TSPAN7 |
| 7296 | thioredoxin reductase 1 | TXNRD1 |
| 7348 | uroplakin 1B | UPK1B |
| 144406 | WD repeat domain 66 | WDR66 |
| 7482 | wingless-type MMTV integration site family, member 2B | WNT2B |
| 201501 | zinc finger and BTB domain containing 7C | ZBTB7C |

Note that, in Tables 1 to 12, "ID" means "Entrez Gene ID." If derived from human, the "SIM2 gene and genes co-expressed with the SIM2 gene (hereinafter also referred to as 'SIM2 co-expression gene group')" and the "FOXE1 gene and genes co-expressed with the FOXE1 gene (hereinafter also referred to as 'FOXE1 co-expression gene group')" are typically each a gene specified under Entrez Gene ID. However, the DNA sequence of a gene may be mutated naturally (i.e., non-artificially) by a mutation or the like. Thus, in the present invention, such naturally-occurring mutants may also be detected.

The evaluation method of the present invention detects an expression of at least one gene from the "SIM2 co-expression gene group." An expression of one gene may be detected (for example, only a gene expression of SPRR3 may be detected), expressions of two genes may be detected, or expressions of three genes may be detected (for example, gene expressions of SPRR3, CEACAM1, and PPL may be detected). Nevertheless, from the viewpoint of evaluating an efficacy of a chemoradiotherapy against squamous cell carcinoma with quite a high precision, it is sufficient to detect expressions of at least five genes (for example, expressions of all genes shown in Table 34), but it is preferable to detect expressions of at least ten genes, more preferable to detect expressions of at least 20 genes, furthermore preferable to detect expressions of at least genes, still furthermore preferable to detect expressions of at least 50 genes, yet furthermore preferable to detect expressions of at least 100 genes, and particularly preferable to detect expressions of all the genes in the SIM2 co-expression gene group. Additionally, as described later in Examples, the rank order of the SIM2 co-expression genes shown in Table 36 is a rank order of contributing to the precision improvement in evaluating an efficacy of a chemoradiotherapy against squamous cell carcinoma. Thus, in the evaluation method of the present invention, it is desirable to select a gene (s) based on the rank order and detect the expression(s).

Moreover, from the viewpoint of evaluating an efficacy of a chemoradiotherapy against squamous cell carcinoma with a higher precision in the evaluation method of the present invention, an expression of at least one gene from the "FOXE1 co-expression gene group" may be detected in addition to the detection of an expression of at least one gene from the SIM2 co-expression gene group. From the FOXE1 co-expression gene group, an expression of one gene may be detected (for example, a gene expression of LOC344887 may be detected), expressions of two genes may be detected, or expressions of three genes may be detected (for example, gene expressions of LOC344887, NTRK2, and TMEM116 may be detected). Nevertheless, from the viewpoint of quite a high precision evaluation, expressions of at least five genes (for example, expressions of all genes shown in Table 33) should be detected, it is preferable to detect expressions of at least ten genes, more preferable to detect expressions of at least 20 genes, furthermore preferable to detect expressions of at least 30 genes, still furthermore preferable to detect expressions of at least 50 genes, yet furthermore preferable to detect expressions of at least 100 genes, and particularly preferable to detect expressions of all the genes in the FOXE1 co-expression gene group. Additionally, as described later in Examples, the rank order of the FOXE1 co-expression genes shown in Table 35 is a rank order of contributing to the precision improvement in evaluating an efficacy of a chemoradiotherapy against squamous cell carcinoma. Thus, in the evaluation method of the present invention, it is desirable to select a gene(s) based on the rank order and detect the expression(s).

Note that, as described later in Examples, depending on expression detection methods and statistical analysis methods to be described later, multiple probes may be prepared for one gene, or different signal-ratio threshold settings model weighting settings may be possible for one gene, for example. In such cases, the number of genes detected in the above-described method of the present invention may be a total number.

In the present invention, "detecting an expression level of a gene" and similar phrases mean detecting the degree of the expression of the gene. Moreover, a level of a gene expressed can be grasped as an absolute amount or a relative amount.

Further, in the present invention, the relative amount can be calculated, as described later in Examples, based on an expression amount of a reference gene. The "reference gene" according to the present invention should be a gene which is stably expressed in a sample (such as a squamous cell carcinoma specimen described above), and whose difference in expression amount is small among different samples. The reference gene is preferably genes shown in Tables 16 to 32 to be described later. More preferable are SRSF3, TPM3, ZNF207, ZNF143, PUM1, RAB1A, and LOC101059961. Particularly preferable is SRSF3.

Further, in the present invention, the "expression level of a gene" means to include both a transcription level and a translation level of the gene. Thus, in the present invention, the "detecting an expression level of a gene" includes detections at both an mRNA level and a protein level.

In the present invention, known methods can be used to detect such an expression of a gene. Examples of the method for quantitatively detecting an mRNA level include PCRs (RT-PCR, real-time PCR, quantitative PCR), and DNA microarray analysis. In addition, an mRNA level can be quantitatively detected by counting the number of reads according to what is called a new generation sequencing method. The new generation sequencing method is not particularly limited. Examples thereof include sequencing-by-synthesis (for example, sequencing using Solexa genome analyzer or Hiseq (registered trademark) 2000 manufactured by Illumina, Inc.), pyrosequencing (for example, sequencing using a sequencer GSLX or FLX manufactured by Roche Diagnostics K. K. (454) (what is called 454 sequencing)), sequencing by ligation (for example, sequencing using SoliD (registered trademark) or 5500xl manufactured by Life Technologies Corporation), and the like. Further, the examples of the method for quantitatively detecting an mRNA level also include northern blotting, in situ hybridization, dot blot, RNase protection assay, and mass spectrometry.

Moreover, examples of the method for quantitatively detecting a protein level include mass spectrometry and detection methods using an antibody (immunological methods) such as ELISA methods, antibody array, immunoblotting, imaging cytometry, flow cytometry, radioimmunoassay, immunoprecipitation, and immunohistochemical staining.

Note that those skilled in the art can prepare an mRNA, a nucleic acid cDNA or cRNA complementary thereto, or a protein to be detected by the aforementioned detection methods by taking the type and state of the specimen and so forth into consideration and selecting a known method appropriate therefor.

In the evaluation method of the present invention, the gene expression thus detected is compared with a reference expression level of the gene. Those skilled in the art can perform the comparison by selecting a statistical analysis method as appropriate in accordance with the aforementioned expression detection methods. Examples of the statistical analysis method include a t-test, analysis of variance (ANOVA), Kruskal-Wallistest, Wilcoxon test, Mann-Whitney test, and odds ratio. Moreover, in the event of the comparison, normalized expression data or standardized and normalized expression data can also be used.

Meanwhile, the comparison target "reference expression level of the corresponding gene" is not particularly limited. Those skilled in the art can set the "reference expression level" as what is called a cutoff value in accordance with the aforementioned expression detection methods and statistical analysis methods, so that it is possible to determine that an efficacy of a chemoradiotherapy against squamous cell carcinoma is high or low based on the "reference expression level." The reference expression level may be an average value of gene expression levels for genes detected in a number of squamous cell carcinomas, as will be described later in Examples. Alternatively, the "reference expression level" may be a value determined by comparing expression levels of genes detected in a patient group for whom an efficacy of a chemoradiotherapy against squamous cell carcinoma is high and in a patient group for whom the efficacy is low. Meanwhile, for a patient group for whom a CRT efficacy is high and a patient group for whom the efficacy is low, the "reference expression level" may be predetermined values set based on gene expression amounts in non-cancerous portions, cell lines, and the like. Moreover, as the reference expression level of at least one gene selected from the SIM2 co-expression gene group, it is also possible to use an expression level of the corresponding gene in a squamous cell carcinoma specimen isolated from a patient who has been revealed in advance that an efficacy of a chemoradiotherapy against squamous cell carcinoma is low. On the other hand, as the reference expression level of at least one gene selected from the FOXE1 co-expression gene group, it is also possible to use an expression level of the corresponding gene in a squamous cell carcinoma specimen isolated from a patient who has been revealed in advance that an efficacy of a chemoradiotherapy against squamous cell carcinoma is high.

Then, as a result of such a comparison, if the expression level of at least one gene selected from the SIM2 co-expression gene group in the subject is higher than the reference expression level, it can be determined that an efficacy of a chemoradiotherapy against squamous cell carcinoma in the subject is high. Herein, the result of "higher than the reference expression level" can be determined by those skilled in the art as appropriate based on the aforementioned statistical analysis methods. As will be described later in Examples, an example thereof includes that a detected gene expression level is higher than the corresponding reference expression level, where a significant difference is found therebetween by a t-test (P<0.05). Moreover, the example also includes that a detected gene expression level is twice or more as high as the corresponding reference expression level.

Moreover, from the viewpoint of evaluating an efficacy of a chemoradiotherapy against squamous cell carcinoma with a higher precision in the evaluation method of the present invention, it is preferable to perform a determination based on the expression level of the FOXE1 co-expression gene group, in addition to the determination based on the expression level of the SIM2 co-expression gene group. To be more specific, if the expression level of at least one gene selected from the SIM2 co-expression gene group is higher than the reference expression level thereof and the expression level of at least one gene selected from the FOXE1 co-expression gene group in the subject is lower than the reference expression level thereof, it is preferably determined that an efficacy of a chemoradiotherapy against squamous cell carcinoma in the subject is high. Herein, the result of "lower than the reference expression level" can be determined by those skilled in the art as appropriate based on the aforementioned statistical analysis methods. As will be described later in Examples, an example thereof includes that a detected gene expression level is lower than the corresponding reference expression level, where a significant difference is found therebetween by a t-test (P<0.05). Moreover, the example also includes that a detected gene expression level is half or less of the corresponding reference expression level.

Preferred embodiments of the method for evaluating an efficacy of a chemoradiotherapy against squamous cell carcinoma of the present invention have been described as above. However, the evaluation method of the present invention is not limited to the above-described embodiments. For example, as described above, it has been revealed that the FOXE1 gene and the genes co-expressed with the FOXE1 gene are expressed at high levels in the poor prognosis subtype obtained by the unsupervised cluster analysis based on the comprehensive gene expression profile. Based on this finding, the present invention can also provide a method for evaluating an efficacy of a chemoradiotherapy against squamous cell carcinoma, the method comprising the following steps (a) to (c):

(a) detecting an expression level of at least one gene selected from a FOXE1 gene and genes co-expressed with the FOXE1 gene in a squamous cell carcinoma specimen isolated from a subject;

(b) comparing the expression level detected in the step (a) with a reference expression level of the corresponding gene; and (c) determining that an efficacy of a chemoradiotherapy against squamous cell carcinoma in the subject is high if the expression level in the subject is lower than the reference expression level as a result of the comparison in the step (b).

In addition, as has been described above, the present invention makes it possible to precisely evaluate an efficacy of a chemoradiotherapy against squamous cell carcinoma. Then, based on the result of such an evaluation, it is also possible to determine whether to select a chemoradiotherapy as a method for treating squamous cell carcinoma, or whether to select another treatment method (such as a therapy for removing squamous cell carcinoma by a surgical operation or an endoscopic operation, a therapy for removing squamous cell carcinoma by laser beam irradiation).

Thus, the present invention can also provide a method for treating squamous cell carcinoma, the method comprising a step of performing a chemoradiotherapy on a subject who has been determined that an efficacy of a chemoradiotherapy against squamous cell carcinoma is high according to the evaluation method of the present invention. Moreover, the present invention can also provide a method for treating squamous cell carcinoma, the method comprising a step of performing a therapy for removing squamous cell carcinoma by a surgical operation or an endoscopic operation, or a therapy for removing squamous cell carcinoma by laser beam irradiation, on a subject who has been determined that an efficacy of a chemoradiotherapy against squamous cell carcinoma is not high according to the evaluation method of the present invention.

Additionally, the evaluation of an efficacy of a chemoradiotherapy against squamous cell carcinoma in a subject is normally conducted by a doctor (including one instructed by the doctor, the same shall apply hereinafter). The data on the above-described gene expression level and so forth obtained by the method of the present invention are useful in a diagnosis including the selection of the therapy by a doctor. Thus, the method of the present invention can also be described as a method for collecting and presenting data useful in a diagnosis by a doctor.

<Agent for Evaluating Efficacy of Chemoradiotherapy Against Squamous Cell Carcinoma>

As described above, the evaluation method of the present invention makes it possible to evaluate an efficacy of a chemoradiotherapy against squamous cell carcinoma by detecting expression levels of the SIM2 co-expression gene group and so on at an mRNA (transcription product) level or a protein (translation product) level. Thus, the present invention provides an agent for evaluating an efficacy of a chemoradiotherapy against squamous cell carcinoma by the above-described evaluation method, the agent comprising at least one compound selected from the following (a) to (d):

(a) an oligonucleotide having a length of at least 15 nucleotides and being capable of hybridizing to a transcription product of at least one gene selected from a SIM2 gene and genes co-expressed with the SIM2 gene or a complementary nucleic acid to the transcription product;

(b) an oligonucleotide having a length of at least 15 nucleotides and being capable of hybridizing to a transcription product of at least one gene selected from a FOXE1 gene and genes co-expressed with the FOXE1 gene or a complementary nucleic acid to the transcription product;

(c) an antibody capable of binding to a translation product of at least one gene selected from a SIM2 gene and genes co-expressed with the SIM2 gene; and (d) an antibody capable of binding to a translation product of at least one gene selected from a FOXE1 gene and genes co-expressed with the FOXE1 gene.

The oligonucleotides which the agent of the present invention comprises may be in the form of primer or may be in the form of probe in accordance with the aforementioned detection methods at an mRNA (transcription product) level.

The primer which the agent of the present invention comprises is not particularly limited, as long as it is capable of hybridizing a transcription product (mRNA) of at least one gene selected from the SIM2 co-expression gene group and the FOXE1 co-expression gene group (hereinafter also referred to as "prognosis related gene(s)") or a complementary nucleic acid (cDNA, cRNA) to the transcription product, enabling amplification and detection of the transcription product and so on. The primer may be constituted of only a DNA, or part or whole of the primer may be substituted with an artificial nucleic acid (modified nucleic acid) such as a bridged nucleic acid. Moreover, the size of the primer should be at least approximately 15 nucleotides long or longer, preferably 15 to 100 nucleotides long, more preferably 18 to 50 nucleotides long, and furthermore preferably 20 to 40 nucleotides long. Further, since the number of primers required differs depending on the type of the aforementioned detection methods, the number of primers which the agent of the present invention comprises is not particularly limited. Nevertheless, the agent of the present invention may comprise two or more primers for each one prognosis related gene. Additionally, those skilled in the art can design and prepare such primers by known methods in accordance with the aforementioned detection methods.

The probe which the agent of the present invention comprises is not particularly limited, as long as it is capable of hybridizing a transcription product of the prognosis related gene or a complementary nucleic acid to the transcription product, enabling detection of the transcription product and so on. The probe can be a DNA, an RNA, an artificial nucleic acid, a chimeric molecule thereof, or the like. The probe may be either single-stranded or double-stranded. The size of the probe should be at least approximately 15 nucleotides long or longer, preferably 15 to 1000 nucleotides long, more preferably 20 to 500 nucleotides long, and furthermore preferably 30 to 300 nucleotides long. Those skilled in the art can prepare such probes by known methods. In addition, the probe may be provided in the form immobilized on a substrate as in a microarray.

The antibodies which the agent of the present invention comprises are not particularly limited, as long as they are capable of specifically binding to translation products of the prognosis related genes. For example, an antibody against the translation product may be either a polyclonal antibody or a monoclonal antibody, or may be a functional fragment (such as Fab, Fab', scFv) of an antibody. Those skilled in the art can prepare such antibodies by known methods. Moreover, the antibody may be provided in the form immobilized on a substrate such as a plate for use in an ELISA method, antibody array, and the like.

In addition, the oligonucleotide or antibody which the agent of the present invention comprises may be labeled with a labeling substance in accordance with the aforementioned detection methods. Examples of the labeling substance include fluorescent substances such as FITC, FAM, DEAC, R6G, TexRed, and Cy5; enzymes such as β-D-glucosidase, luciferases, and HRP; radioisotopes such as $^3$H, $^{14}$C, $^{32}$P, $^{35}$S, and $^{123}$I; affinity substances such as biotin and streptavidin; and luminescent substances such as luminal, luciferins, and lucigenin.

Further, the agent of the present invention may comprise other ingredients acceptable as compositions, in addition to the oligonucleotide or antibody. Examples of the other ingredients include carriers, excipients disintegrators, buffers, emulsifiers, suspensions, stabilizers, preservatives, antiseptics, physiological salines, secondary antibodies, and the like.

Furthermore, the agent of the present invention can be combined with a substrate necessary for detection of a label, a positive control or a negative control, a buffer solution used to dilute or wash a specimen, or the like. Thus, a kit for evaluating an efficacy of a chemoradiotherapy against squamous cell carcinoma can also be provided. Further, such a kit may comprise an instruction for the kit.

EXAMPLES

Hereinafter, the present invention will be described more specifically based on Examples. However, the present invention is not limited to the following Examples.

[1] Identification of Subtypes by Unsupervised Cluster Analysis Based on Comprehensive Gene Expression Profile In order to develop a method for evaluating an efficacy of a chemoradiotherapy against squamous cell carcinoma, an unsupervised cluster analysis based on a comprehensive gene expression profile was conducted to identify subtypes correlated with treatment prognoses after a chemoradiotherapy against squamous cell carcinoma.

To be more specific, first, total RNAs were extracted from biopsy tissues of 274 cases of locally advanced esophageal squamous cell carcinoma patients at stages of II-III before a treatment. A comprehensive gene expression profile was obtained by using GeneChip (registered trademark) Human Genome U133 Plus 2.0 Array according to the method recommended by Affymetrix, Inc. The gene expression profile was divided into a 107-case set for subtyping (set-1) and a 167-case set for validation (set-2). A two-dimensional cluster analysis (method for creating two-dimensional phylogenetic trees of gene probe clusters and case clusters) was conducted using Java TreeView and freeware Cluster 3.0 provided from Stanford University. Regarding set-1, gene probes (multiple probes were synthesized and placed on one gene in some cases) which were at the detection limit or below in all the cases and gene probes whose signals did not vary among the cases were excluded. Thus, 2054 gene probes were selected, and an unsupervised cluster analysis was conducted without clinicopathological information. Next, among the obtained two-dimensional phylogenetic trees of the gene probe clusters and the case clusters, the top gene probe clusters were divided into seven sets. The seven gene probe sets were separately subjected to a cluster analysis using gene expression data on case sets-1 and -2.

Thus, five case clusters which exhibited signals of the entire gene probe set at high expression levels with good reproducibility in both of the sets were identified: subtypes-1a, -2b, -3b, -5, and -7. Between each subtype among the subtypes and other samples, the survival curves and the five-year survival rates were compared by using 121 chemoradiotherapy (CRT) cases (set-1=34 cases, set-2=87 cases) in all the 274 cases. Thus, good prognosis subtype-7 and poor prognosis subtype-5 were identified with good reproducibility (see FIG. 1).

[2] Re-Classification into Chemoradiotherapy-Sensitive and Non-Sensitive Subtypes Data mining software GeneSpring of a gene expression analysis array manufactured by Agilent Technologies was used to select gene sets which allowed classifications of CRT-sensitive subtype-7 and non-sensitive subtype-5 with a biological significance, and the genes were used for re-classification. These followed procedures A) to C) below.

A) A t-test (P<0.05) was conducted on gene expression signal values between each subtype of subtypes-7 and -5 identified in [1] and the other samples in set-1. The average values thereof were compared (2-fold or more). Thereby, genes significantly expressed at high levels in the subtypes were selected.

B) From the compositions of the genes selected in A), an activation of a differentiation induction pathway by a transcription factor SIM2 was predicted in subtype-7, and activations of radiation and drug resistance pathways by FOXE1 were predicted in subtype-5. Next, genes co-expressed with SIM2 and FOXE1 were selected by evaluating the expression pattern correlations among the samples in set-1 with a Pearson product-moment correlation coefficient (0.4 or more). The validities of the molecular pathways activated in the two subtypes predicted from the compositions of the selected gene sets were verified.

C) Genes common in A) and B) were selected in each the subtypes. A 191-gene set (Tables 1 to 7) for the subtype-7 classification and a 121-gene set (Tables 8 to 12) for the subtype-5 classification were determined. A clustering analysis was conducted using these gene sets. Subtypes were re-classified in sets-1 and -2, and survival curves were compared between each sample group classified as the subtypes and other sample groups. The result revealed that CRT-sensitive subtype-7 and non-sensitive subtype-5 were classified with good reproducibility (see FIG. 2).

[3] Identification Method for Pure Subtypes-7 and -5

After the classification into subtypes-7 and -5, some samples belonging to both of the subtypes were considered not to belong to any of the subtypes. Thereby, pure subtype-7, pure subtype-5, and the others were classified (see FIG. 3).

[4] Comparison of CRT and Surgical Resection Outcomes Between Pure Subtypes-7 and -5

Figure 4:
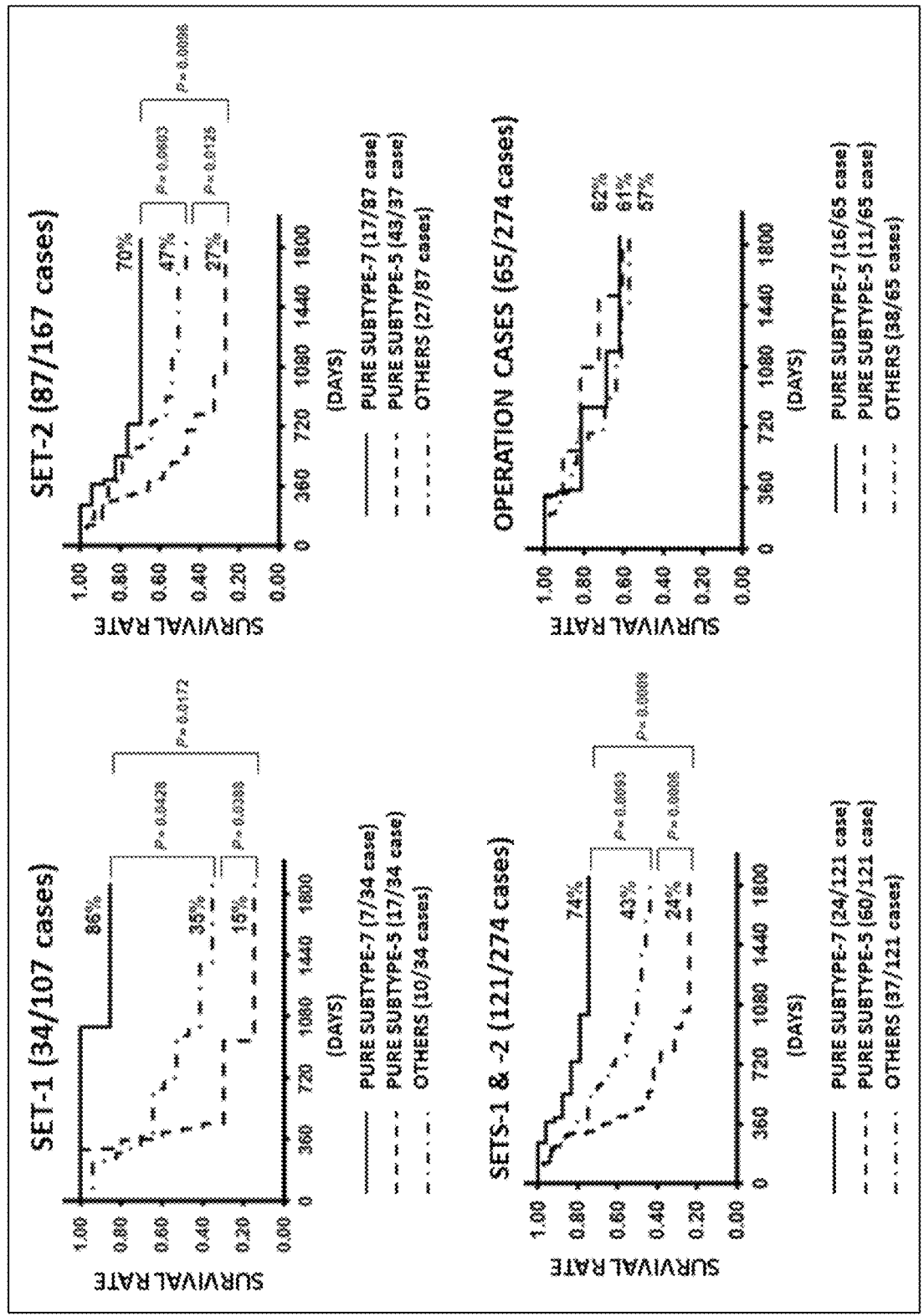
FIG. 4 shows graphs for illustrating a comparison of the survival rates after CRT or surgical resection between a squamous cell carcinoma patient group classified as pure subtype-7 (classified as subtype-7 but not classified as subtype-5) and a squamous cell carcinoma patient group classified as pure subtype-5 (classified as subtype-5 but not classified as subtype-7). In the figure, only the lower right graph illustrates the survival rates after the treatment by surgical resection. The others show graphs for illustrating the survival rates after CRT.

The complete response rates two months after the CRT treatment, survival curves, and five-year survival rates were compared among pure subtype-7, pure subtype-5, and the others classified in [3] (see Table 15, FIG. 4). Further, the same subtype classification was carried out on 65 cases having been subjected to surgical resection (operation), and the survival curves and the five-year survival rates were compared (see FIG. 4).

[5] Evaluation of Differentiation-Inducing Activity of SIM2 Gene Defining CRT-Sensitive Subtype-7

Figure 5:
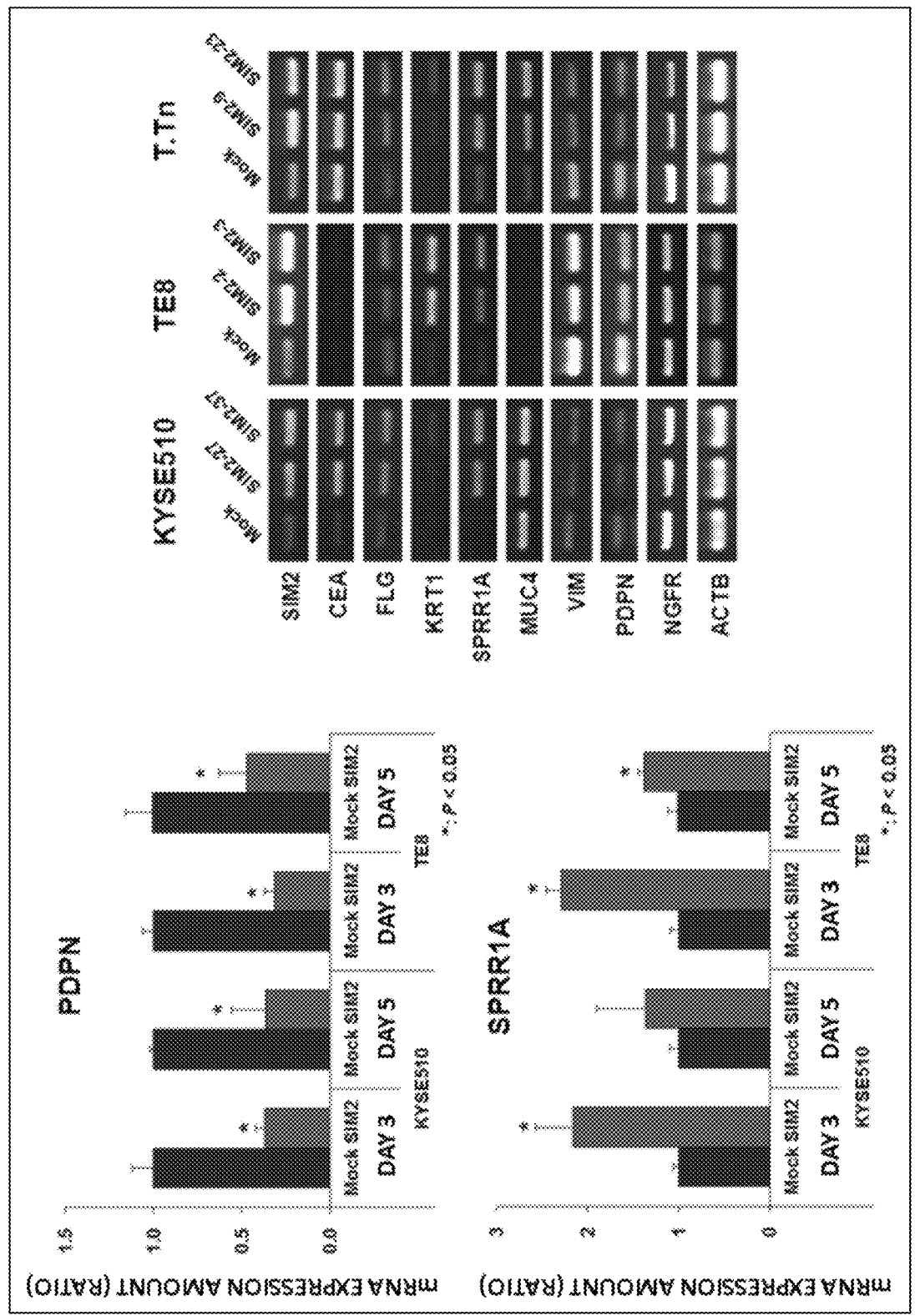
FIG. 5 is a figure for illustrating the result of analyzing the differentiation-inducing activity of the SIM2 gene. In the figure, two graphs on the left are graphs for illustrating the mRNA expression amounts of an undifferentiated-basal-cell marker PDPN and a differentiation marker SPRR1A in esophageal squamous cell carcinoma cell lines (KYSE510 and TE8) transiently expressing the SIM2 gene. The photographs are photographs of gel electrophoresis for illustrating the expression amounts of SIM2, differentiation markers (CEA, FLG, KRT1, SPRR1A, MUC4), and undifferentiation markers (VIM, PDPN, NGFR) in SIM2 stably expressing cell lines (KYSE510-SIM2-27 and -37, TE8-SIM2-2 and -3, T.Tn-SIM2-9 and -23) of esophageal squamous cell carcinoma cell lines KYSE510, TE8, and T.Tn.

To evaluate the differentiation-inducing activity of the SIM2 gene, a SIM2 gene cDNA ligated to a pCMV-AC-GFP plasmid vector was transiently introduced using Lipofectamin (registered trademark) 2000 (Invitrogen Corporation) into esophageal squamous cell carcinoma-derived cell lines KYSE510 and TE8 obtained from RIKEN BRC or JCRB. In control groups, a pCMV-neo plasmid vector was transiently introduced. After cultured for 1 day in a normal medium (RPMI1640 or DMEM, 10% FBS), the resultant was seeded into NanoCulture (registered trademark) Plate (SCIVAX Life Sciences, Inc.) and cultured with a normal medium for 3 days. The total RNA was extracted, and the gene expression amount was measured by a quantitative RT-PCR method. The cDNA was prepared according to SuperScript (registered trademark) III First-Strand Synthesis System for RT-PCR (Invitrogen Corporation). The diluted cDNA was mixed with iQTM SYBER (registered trademark) Green Supermix (BIO-RAD Laboratories, Inc.), primers, and nuclease-freewater, and quantified using MyiQ (registered trademark) (BIO-RAD Laboratories, Inc.). Table 13 shows the base sequences of the primers. FIG. 5 shows the result.

TABLE 13

| Gene | Primer | |
|------|--------|---|
| SIM2 | Forward: | 5'-CTTCCCTCTGGACTCTCACG-3' (SEQ ID NO: 1) |
| | Reverse: | 5'-AGGCTGTGCCTAGCAGTGTT-3' (SEQ ID NO: 2) |
| SPRR1A | Forward: | 5'-TGGCCACTGGATACTGAACA-3' (SEQ ID NO: 3) |
| | Reverse: | 5'-CCCAAATCCATCCTCAAATG-3' (SEQ ID NO: 4) |
| PDPN | Forward: | 5'-TGACTCCAGGAACCAGCGAAG-3' (SEQ ID NO: 5) |
| | Reverse: | 5'-GCGAATGCCTGTTACACTGTTGA-3' (SEQ ID NO: 6) |
| ACTB | Forward: | 5'-GAAGTCCCTTGCCATCCTAA-3' (SEQ ID NO: 7) |
| | Reverse: | 5'-GCACGAAGGCTCATCATTCA-3' (SEQ ID NO: 8) |

The SIM2 gene was introduced into TE8 obtained from RIKEN BRC and KYSE510 and T. Tn obtained from JCRB Cell Bank. The resultant was cultured in a medium containing 400 µg/ml of G-418 for approximately 2 weeks. The G418 resistant colonies were isolated and cultured. The SIM2 gene expression was confirmed by an RT-PCR method. Thus, SIM2-gene stably expressing lines were established. Cell lines in which only a GFP expression plasmid vector was introduced were prepared as control cell lines. To extract the total RNAs and evaluate the differentiation-inducing activities of the SIM2-gene stably expressing lines, the SIM2-gene stably expressing lines were each seeded into NanoCulture (registered trademark) Plate and then cultured with a normal medium for 3 days. The total RNA was extracted, and an RT-PCR method was performed. The cDNA was synthesized using SuperScript (registered trademark) III First-Strand Synthesis System for RT-PCR. The diluted cDNA was mixed with AccuPrime (registered trademark) Taq DNA Polymerase System (Invitrogen), primers, and nuclease-free water, and amplified using GeneAmp (registered trademark) PCR System 9700 (Applied Biosystems Inc.). The resultant was quantified and compared by agarose gel electrophoresis. Table 14 shows the base sequences of the primers. FIG. 5 shows the result.

TABLE 14

| Gene | Primer |
|------|--------|
| CEA | Forward: 5'-AGACTCTGACCAGAGATCGA-3' (SEQ ID NO: 9) Reverse: 5'-GGTGGACAGTTTCATGAAGC-3' (SEQ ID NO: 10) |
| FLG | Forward: 5'-GGAGATTCTGGGTCAAGTAATGTT-3' (SEQ ID NO: 11) Reverse: 5'-TGTGCTAGCCCTGATGTTGA-3' (SEQ ID NO: 12) |
| KRT1 | Forward: 5'-ACCGGAGAAAAGAGCTATGG-3' (SEQ ID NO: 13) Reverse: 5'-TGGGGAGTTTAAGACCTCTC-3' (SEQ ID NO: 14) |
| MUC4 | Forward: 5'-TACTTCAGATGCGATGGCTAC-3' (SEQ ID NO: 15) Reverse: 5'-CTGAGTTCAGGAAATAGGAGA-3' (SEQ ID NO: 16) |
| VIM | Forward: 5'-GCTTTCAAGTGCCTTTCTGC-3' (SEQ ID NO: 17) Reverse: 5'-GTTGGTTGGATACTTGCTGG-3' (SEQ ID NO: 18) |
| NGFR | Forward: 5'-AGCTCTAGACAACCCTGCAA-3' (SEQ ID NO: 19) Reverse: 5'-AGGGTTCCATCTCAGCTCAA-3' (SEQ ID NO: 20) |

Figure 6:
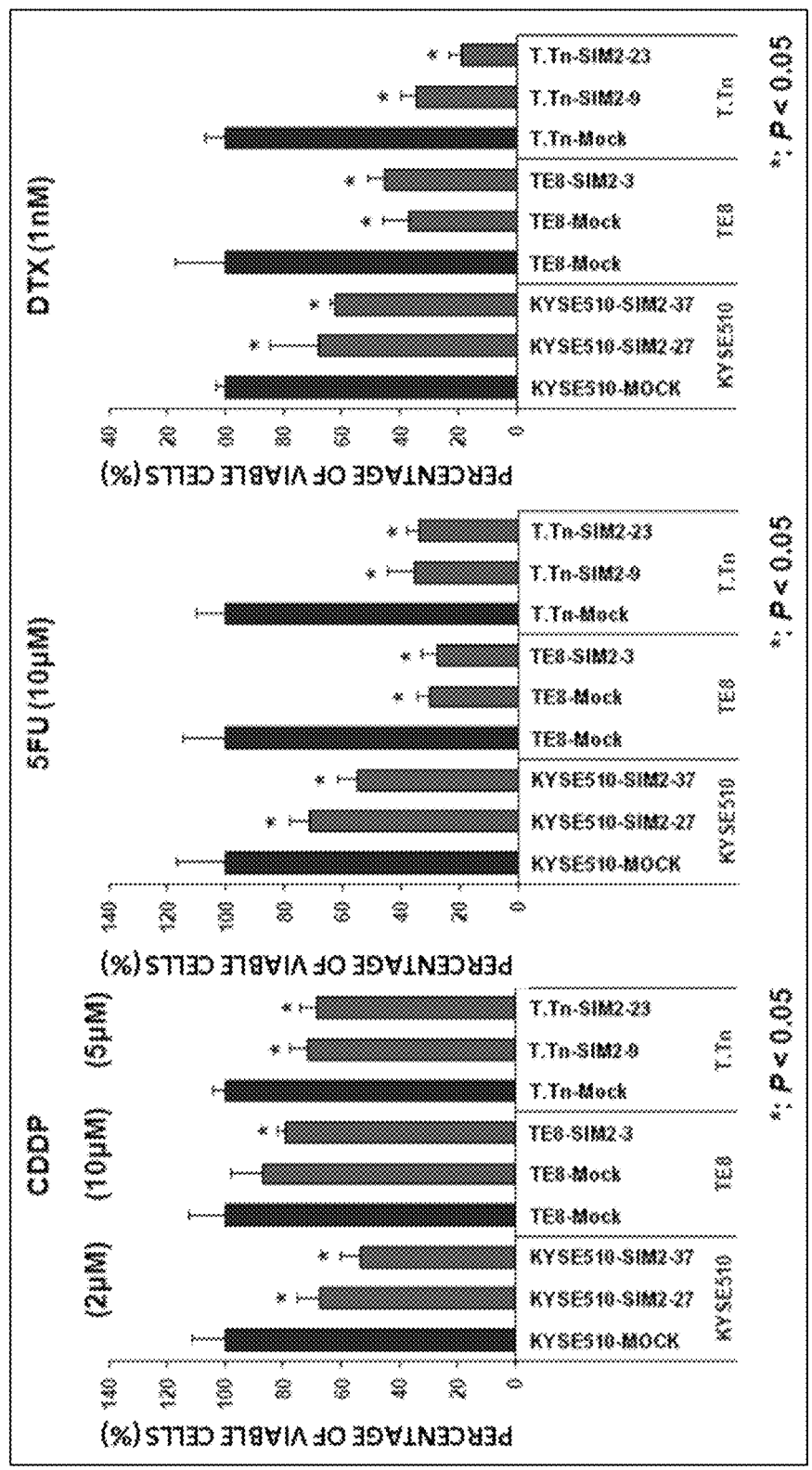
FIG. 6 shows graphs for illustrating the result of analyzing the sensitivities of the SIM2 gene-stably expressing lines to anticancer agents (cisplatin (CDDP), 5-fluorouracil (5-FU), and docetaxel (DTX)) by a two-dimensional culture method.

[6] Evaluation of Anticancer-Agent Sensitivities of SIM2-Gene Stably Expressing Lines by Two-Dimensional Culturing To evaluate the sensitivities of the SIM2-gene stably expressing lines to cisplatin (CDDP), 5-fluorouracil (5-FU), and docetaxel (DTX), an anticancer-agent sensitivity test was conducted. The SIM2-gene stably expressing lines were each seeded into a 6-well plate, cultured with a normal medium for 1 day, and then cultured with a normal medium or a medium supplemented with CDDP (2 µM, 5 µM, 10 µM), 5-FU (10 µM), or DTX (1 nM) for 3 days. After the chemical treatment was completed, the cells were collected using 0.25% trypsin/EDTA and stained with trypan blue. After that, the number of viable cells was counted. FIG. 6 shows the result.

Figure 7:
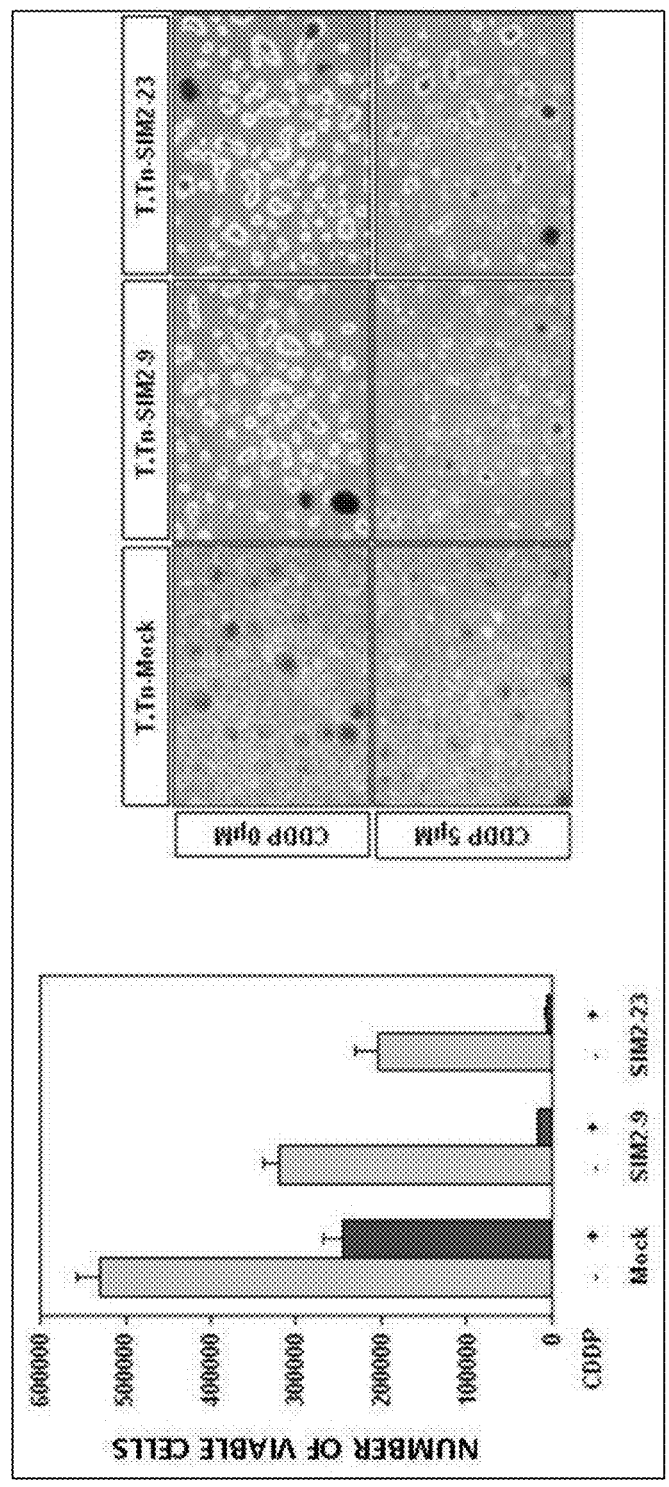
FIG. 7 shows a graph and micrographs for illustrating the result of analyzing the sensitivities of the SIM2-gene stably expressing lines to CDDP long-term administration by a three-dimensional culture method.

[7] Evaluation of Cisplatin Sensitivities of SIM2-Gene Stably Expressing Lines by Three-Dimensional Culturing To evaluate the sensitivities of the SIM2-gene stably expressing lines to CDDP long-term administration, an anticancer-agent sensitivity test was conducted employing three-dimensional culturing. The SIM2-gene stably expressing lines were each seeded into 3.5 cm NanoCulture (registered trademark) Plate, and cultured with a normal medium for 1 day. Then, the medium was replaced with a medium containing CDDP ($5 \times 10^{-6}$M). While the medium containing CDDP ($5 \times 10^{-6}$ M) was replaced at intervals of two days, the culturing was continued for 14 days. After the chemical treatment was completed, the cells were collected using Spheroid Dispersion Solution (SCIVAX Life Sciences, Inc.) and stained with trypan blue. After that, the number of viable cells was counted. FIG. 7 shows the result.

[8] Evaluation of γ-Ray Sensitivities of SIM2-Gene Stably Expressing Lines by Two-Dimensional Culturing To evaluate the sensitivities of the SIM2-gene stably expressing lines to radiation, a γ-ray sensitivity test was conducted. The SIM2-gene stably expressing lines were each seeded into a 6-well plate, cultured with a normal medium for 1 day, and then irradiated with γ rays (0 Gy, 1

Figure 8:
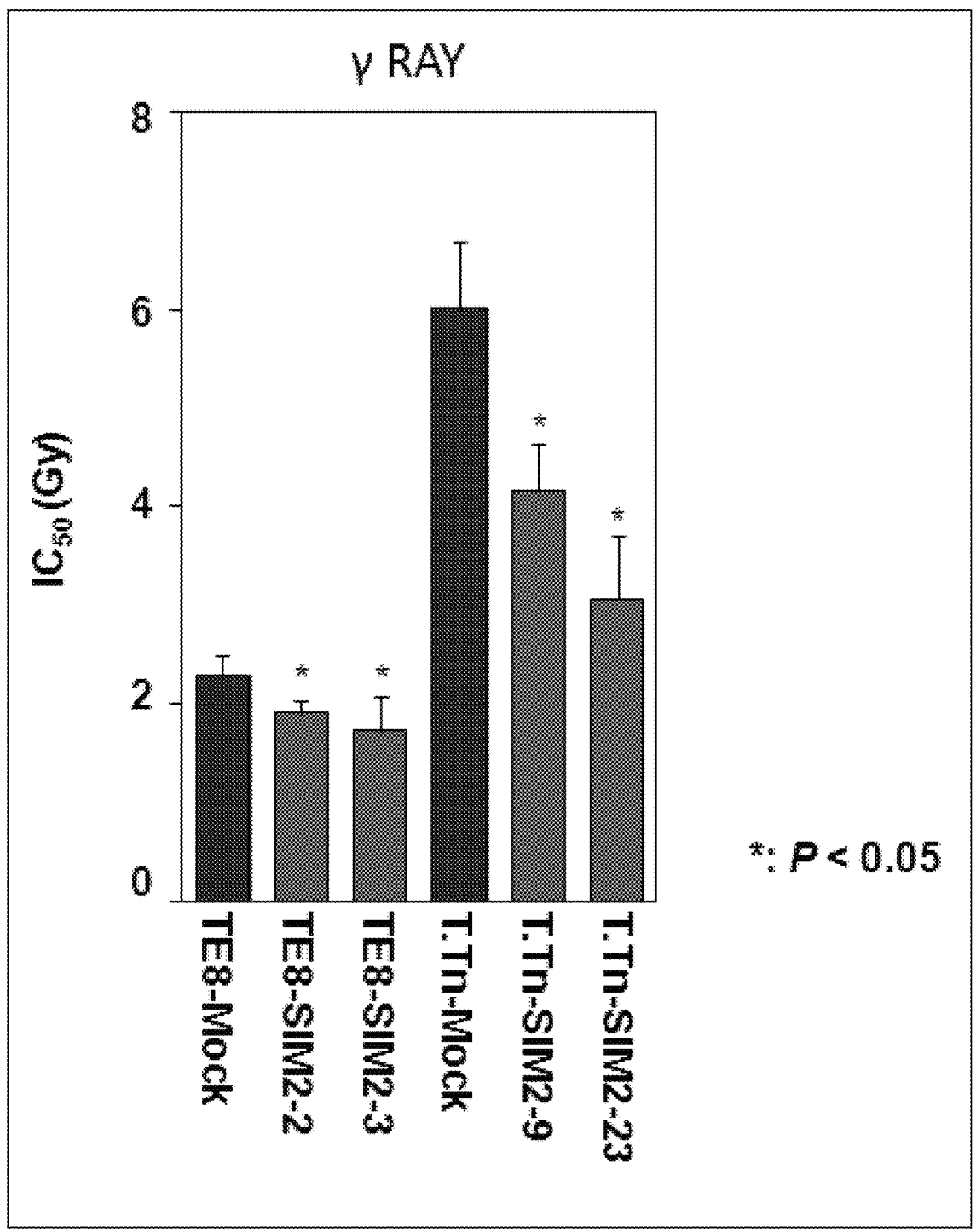
FIG. 8 is a graph for illustrating the result of analyzing the γ-ray sensitivities of the SIM2-gene stably expressing lines by the two-dimensional culture method.

Gy, 5 Gy, 10 Gy). After culturing for 7 days, the cells were collected using 0.25% trypsin/EDTA and stained with trypan blue. After that, the number of viable cells was counted, and the IC50 was calculated. FIG. 8 shows the result.

The results obtained based on the above methods will be described below.

[1] Identification of Subtypes by Unsupervised Cluster Analysis Based on Comprehensive Gene Expression Profile The unsupervised cluster analysis was conducted on the 2054-gene probe set selected in case set-1, the gene phylogenetic trees were divided into seven, and the reproducibilities in case set-2 were checked. As a result, among the seven gene probe clusters, five gene probe clusters were reproduced in set-2, too. As shown in FIG. 1, among case clusters (subtypes) which expressed these five gene probe sets at high levels, subtype-7 exhibited a sensitivity such that the five-year survival rate after CRT was 64% in set-1 and 75% in set-2. On the other hand, subtype-5 was non sensitive: the five-year survival rate after CRT was 11% in set-1 and 28% in set-2.

Figure 2:
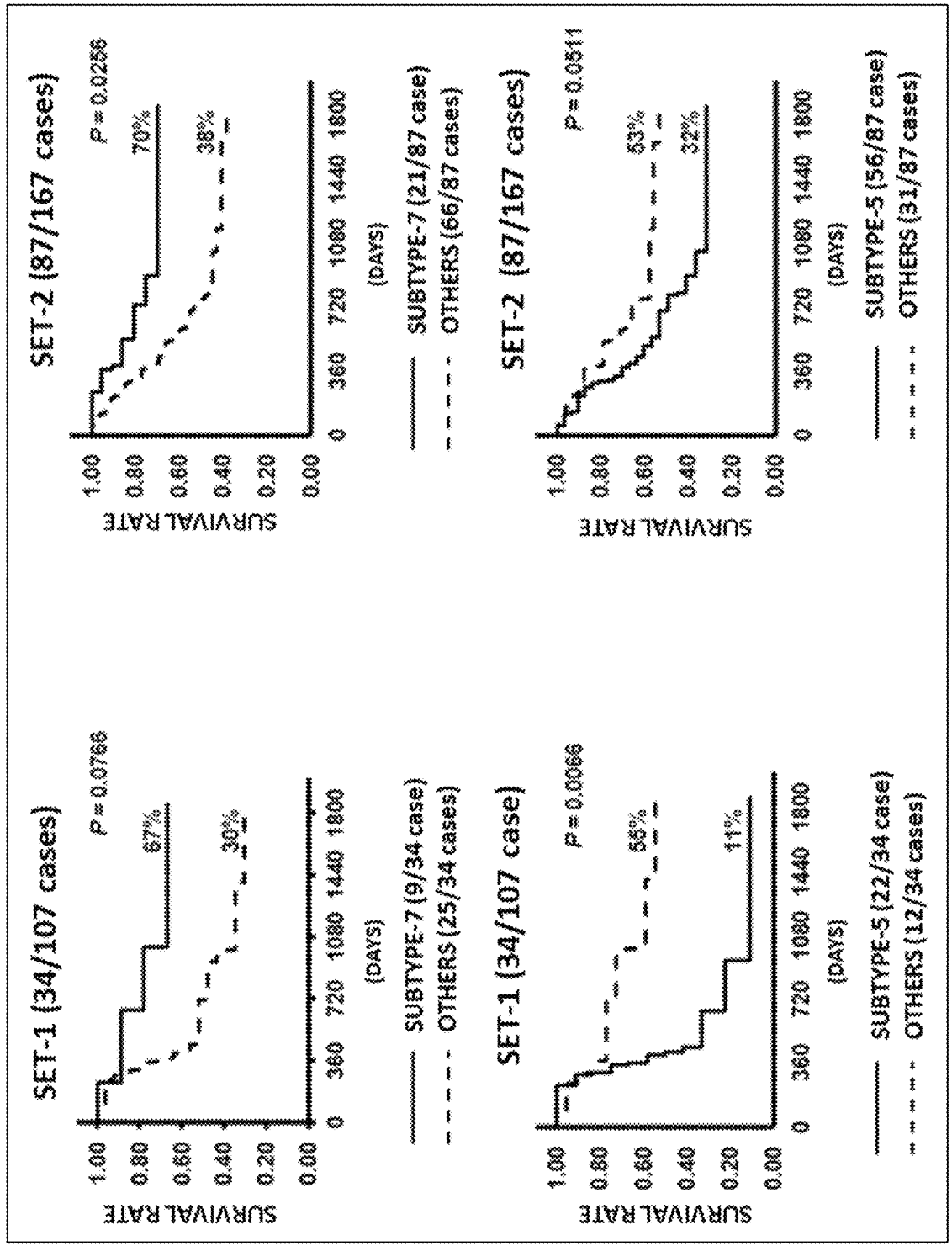
FIG. 2 shows graphs for illustrating a comparison of the survival rates after CRT between a squamous cell carcinoma patient group (in the figure, subtype-7) classified on the basis of high expression levels of a SIM2 gene and genes co-expressed with the SIM2 gene and a squamous cell carcinoma patient group (in the figure, subtype-5) classified on the basis of high expression levels of a FOXE1 gene and genes co-expressed with the FOXE1 gene.

[2] Re-Classification into Chemoradiotherapy-Sensitive Subtype and Non-Sensitive Subtype CRT-sensitive subtype-7 was compared with the others in set-1, and gene probes were selected which satisfied the condition of p<0.05 in the t-test and the condition of the average expression level being 2-fold or more. As a result, there were 599 gene probes. A key transcription factor included among these, that is, a transcription factor controlling the expressions of these genes, was searched for by a correlation analysis on expression amounts in each case, so that SIM2 was found. Among the 599 gene probes selected statistically as described above, genes expressed in correlation with the expression of SIM2 were 256 gene probes. Similarly, FOXE1 was identified as a transcription factor which correlated with 163 gene probes among 525 gene probes specifically expressed in non-sensitive subtype-5. Next, using numerical data on each of the 256 gene probes and the 163 gene probes, the cluster analysis was conducted on set-1 and set-2, so that CRT-sensitive subtype-7 and non-sensitive subtype-5 were re-classified. The survival curves were drawn, and the five-year survival rates were examined. FIG. 2 shows the result. As shown in FIG. 2, the outcome of subtype-7 was favorable; the five-year survival rate was 67% in set-1 and 70% in set-2. On the other hand, that of subtype-5 was unfavorable; the five-year survival rate after CRT was 11% in set-1 and 32% in set-2. The 256 gene probes defining CRT-sensitive subtype-7 were organized as 191 gene names without redundancy, which have been shown in Tables 1 to 7 described above. The 191 genes defining CRT-sensitive subtype-7 included a lot of genes (differentiation markers) expressed in the differentiation layer of esophageal squamous epithelium. On the other hand, the 163 gene probes defining non-sensitive subtype-5 have been shown as 121 genes in Tables 8 to 12 described above. These genes included a lot of undifferentiated-basal-cell markers and the like. Thus, it was shown that SIM2 induced the differentiation of esophageal cancer, and that FOXE1 suppressed the differentiation, and thereby contributed to the acquisition of chemical and radiation resistances.

[3] Identification of Pure Subtypes-7 and -5

Figure 3:
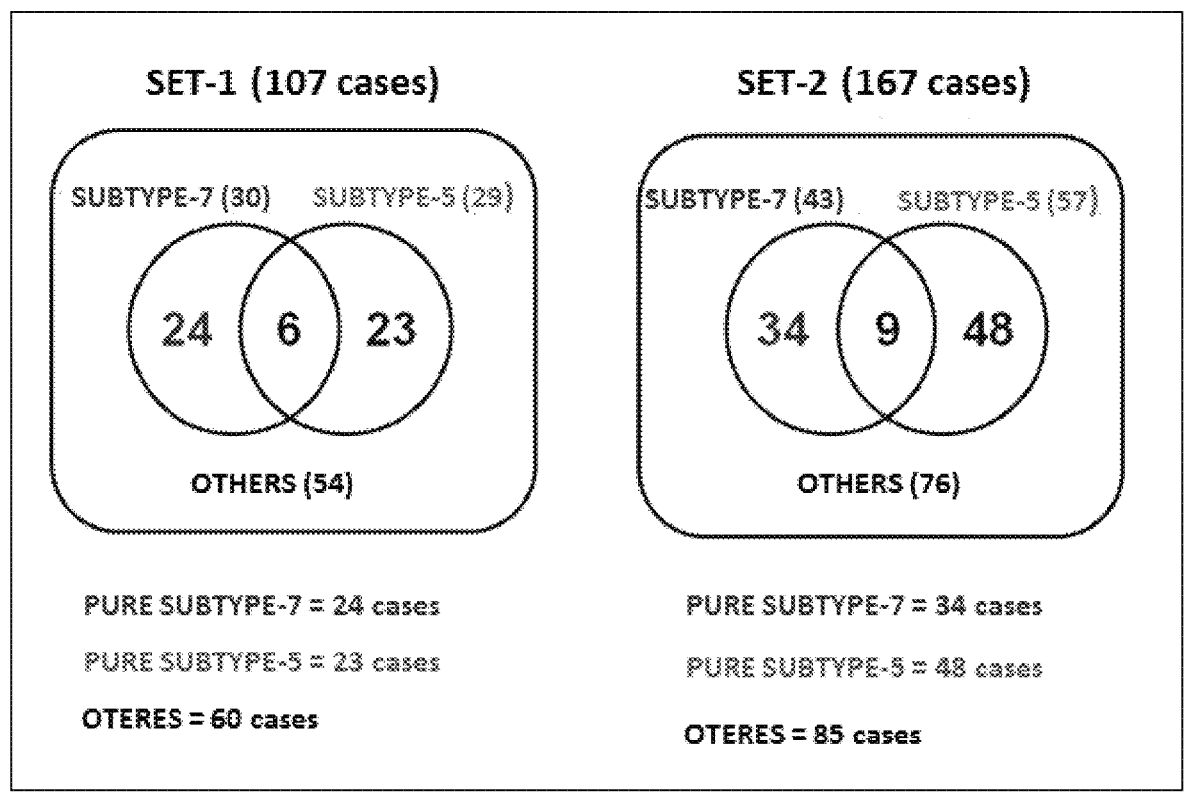
FIG. 3 shows Venn diagrams for illustrating the number of patients belonging to subtype-7, subtype-5, and both of the subtypes in a squamous cell carcinoma patient group.

As shown in FIG. 3, among the 107 cases of set-1, 30 cases were classified as subtype-7, and 29 cases were classified as subtype-5. Since six cases overlapped therebetween, 24 cases were classified as pure subtype-7, and 23 cases were classified as pure subtype-5. There were 60 cases which were other than these two subtypes. Similarly, among the 167 cases of set-2, 34 cases were classified as pure subtype-7, and 48 cases were classified as pure subtype-5. There were 85 cases which were other than the two.

[4] Comparison of CRT and Surgical Resection Outcomes Between Pure Subtypes-7 and -5

Table 15 shows the complete response (CR) rates two months after the CRT treatment on pure subtype-7, pure subtype-5, and the other cases classified in [3]. Note that, in Table 15, "ST" indicates "subtype", "CR" indicates "complete response," and "non CR" indicates "non complete response." As shown in Table 15, the complete response rate of the 121 CRT cases was 47%. Meanwhile, the complete response rate of pure subtype-7 was favorably 100% in set-1 and 59% in set-2 with good reproducibility, and the complete response rate as a whole was 71%. On the other hand, the complete response rate of pure subtype-5 was unfavorably 18% in set-1 and 24% in set-2 with good reproducibility, and the complete response rate as a whole was 23%.

TABLE 15

|  | Set-1 | | | Set-2 | | | All cases | | |
| --- | --- | --- | --- | --- | --- | --- | --- | --- | --- |
|  | CR (number of cases) | non CR (number of cases) | CR rate (%) | CR (number of cases) | non CR (number of cases) | CR rate (%) | CR (number of cases) | non CR (number of cases) | CR rate (%) |
| All cases | 18 | 35 | 51 | 41 | 90 | 46 | 59 | 125 | 47 |
| ST-7 | 7 | 7 | 100 | 10 | 17 | 59 | 17 | 24 | 71 |
| ST-5 | 2 | 11 | 18 | 7 | 29 | 24 | 9 | 40 | 23 |
| Others | 9 | 17 | 53 | 24 | 44 | 55 | 33 | 61 | 54 |

FIG. 4 shows data for comparing the survival curves and the five-year survival rates of pure subtype-7, pure subtype-5, and the other cases in the 121 CRT cases (upper left: set-1, upper right: set-2, lower left: sets-1 & -2). In addition, the 65 operation cases among all the 274 cases were also subjected to the same subtype classification The survival curves and the five-year survival rates were compared (lower right: the operation cases). The five-year survival rate of the 121 CRT cases was 44%. Meanwhile, the five-year survival rate of pure subtype-7 was as high as 86% in set-1 and 70% in set-2 with good reproducibility, and the five-year survival rate as a whole (sets-1 & -2) was 74%. On the other hand, the five-year survival rate of subtype-5 was as low as 15% in set-1 and 27% in set-2 with good reproducibility, and the five-year survival rate as a whole (sets-1 & -2) was 24%. The five-year survival rate of all the 65 cases in the operation cases was 59%. Meanwhile, the five-year survival rates of pure subtype-7, pure subtype-5, and the others were respectively 62%, 61%, and 57%. Hence, no significant difference was found. Thus, it was revealed that subtype-5 and subtype-7, or this subtype classification method, were not prognosis factors for predicting surgical resection prognosis but were effective specially in predicting a CRT treatment outcome.

[5] Evaluation of Differentiation-Inducing Activity of SIM2 Gene Defining CRT-Sensitive Subtype-7

Shown on the left of FIG. 5 are data on the quantitative RT-PCR performed to examine the expressions of an undifferentiated-basal-cell marker PDPN and a differentiation marker SPRR1A at Day 3 and Day 5 after the SIM2 gene cDNA was introduced into the esophageal squamous cell carcinoma cell lines KYSE510 and TE8. At Day 3 after the SIM2 gene introduction, the differentiation marker SPRR1A was increased, while the expression of the undifferentiated-basal-cell marker PDPN was decreased. This result revealed that SIM2 was able to induce the differentiation of the undifferentiated basal cells.

Shown on the right of FIG. 5 were data examined by the RT-PCR performed to examine the expressions of SIM2, differentiation markers (CEA, FLG, KRT1, SPRR1A, MUC4), and undifferentiation markers (VIM, PDPN, NGFR) after the three-dimensional culturing of the SIM2 stably expressing cell lines (KYSE510-SIM2-27 and -37, TE8-SIM2-2 and -3, T.Tn-SIM2-9 and -23) of the esophageal squamous cell carcinoma cell lines KYSE510, TE8, and T.Tn and the control-vector introduced lines (KYSE510-Mock, TE8-Mock, T.Tn-Mock). The expressions of the differentiation markers were high but the expressions of the undifferentiation markers were low in the SIM2 stably expressing cells in comparison with the control cells. These data verified, like the data on the transient SIM2-gene expression induction described above (on the left of FIG. 5), that SIM2 was able to induce the differentiation of the undifferentiated basal cells.

[6] Evaluation of Anticancer-Agent Sensitivities of SIM2-Gene Stably Expressing Lines by Two-Dimensional Culturing As shown in FIG. 6, it was revealed that, in the SIM2 stably expressing lines (KYSE510-SIM2-27 and -37, TE8-SIM2-2 and -3, T.Tn-SIM2-9 and -23), the sensitivities to cisplatin (CDDP), 5-fluorouracil (5-FU), and docetaxel (DTX) were increased in comparison with the control-vector introduced lines (KYSE510-Mock, TE8-Mock, T.Tn-Mock). To be more specific, when the three types of the anticancer agents were each added at a concentration near IC50 to any of the SIM2 stably expressing lines by normal plate two-dimensional culturing, the number of viable cells three days thereafter was significantly (*: $p<0.05$) decreased.

[7] Evaluation of Cisplatin Sensitivities of SIM2-Gene Stably Expressing Lines by Three-Dimensional Culturing Since the cells were saturated in the long-term observation of 5 days or longer at a concentration near IC50 by normal two-dimensional culturing, the effect in 3 days was examined. As a result, the CDDP effect shown in FIG. 6 was significant but small. For this reason, regarding CDDP, a long-term observation of 14 days by the three-dimensional culturing was performed. As shown in FIG. 7 (left: the number of viable cells, right: cell aggregates), the sensitivities of the SIM2 stably expressing lines (T.Tn-SIM2-9 and -23) to CDDP were remarkably increased in comparison with the control-vector introduced line (T.Tn-Mock).

[8] Evaluation of γ-Ray Sensitivities of SIM2-Gene Stably Expressing Lines by Two-Dimensional Culturing As shown in FIG. 8, it was revealed that the γ-ray sensitivities of the SIM2 stably expressing lines (TE8-SIM2-2 and -3, T.Tn-SIM2-9 and -23) were increased in comparison with the control-vector introduced lines (TE8-Mock, T.Tn-Mock). Note that both the parental line of KYSE510 and the control-vector introduced line (KYSE510-Mock) were and excluded from the evaluation because of the high sensitivities to γ ray.

[9] Verification of Presence of Subtypes-5 and -7 in Esophageal Squamous Cell Carcinoma in Other Country and Head and Neck Squamous Cell Carcinoma Microarray data on 53 cases of esophageal squamous cell carcinoma from China under access No: E-GEDO-23400 of the ArrayExpress database in EMBL-EBI and 89 cases of head and neck squamous cell carcinoma from France under access No: E-MTAB-1328 were subjected to a cluster analysis by the same method as the aforementioned [1] and [2]. As a result, although unillustrated, the presences of subtypes-5 and -7 were verified also in esophageal squamous cell carcinoma in the other country and further in squamous cell carcinoma other than esophageal squamous cell carcinoma (i.e., head and neck squamous cell carcinoma).

[10] Identification of Reference Genes Whose Expression Variations were Small Based on Comprehensive Gene Expression Profile As has been described above, it is possible to evaluate an efficacy of a chemoradiotherapy against squamous cell carcinoma on the basis of the gene expression level of the SIM2 co-expression gene group. Further, it is also possible to evaluate the efficacy with a higher precision on the basis of the gene expression level of the FOXE1 co-expression gene group. Additionally, in comprehensively analyzing expression levels of such gene groups, an analysis with a DNA microarray adopted also in the present Examples is useful.

Comprehensive analyses such as a DNA microarray analysis are based on the assumption that total expression amounts of genes are almost the same among samples, allowing a comparison of gene expression levels among the samples (global normalization).

However, such global normalization cannot be adopted in analyses by PCR and the like in which only a limited number of genes are analyzed. Hence, an expression amount of a gene to be analyzed is converted to the relative amount (expression level) based on an expression amount of a gene (reference gene) whose expression variation is small among samples, and the gene expression levels are compared among the samples.

Meanwhile, in the analyses by PCR and the like, reference genes such as β-actin and GAPDH are used which are normally constitutively expressed and said that the expression variations are generally small. Nevertheless, these are not always appropriate as reference genes when squamous cell carcinoma is targeted. Hence, the following analysis was conducted to identify more effective reference genes than β-actin and the like in squamous cell carcinoma.

Based on the comprehensive gene expression profile obtained in [1] described above from the biopsy tissues of 274 cases of esophageal squamous cell carcinoma patients before a treatment by using GeneChip (registered trademark) Human Genome U133 Plus 2.0 Array, reference genes whose expression variations were small among the cases were ranked. As the ranking method for the reference genes whose expression variations were small, the following three methods were used and studied.

Method 1: Calculate the 95% percentile and the 5% percentile of signal values for each gene probe. Divide the difference therebetween by the median (50% percentile) of the signal values of the gene probe.

Method 2: Calculate the median absolute deviation of the signal values for each gene probe. Divide the deviation by the median of the signal values of the gene probe.

Method 3: Calculate the standard deviation of the signal values for each gene probe. Divide the deviation by the average value of the signal values of the gene probe.

The size of the expression variation of each gene was evaluated by the above three methods. To be more specific, in any of the methods, the smaller the gene expression variation, the smaller the numerical value to be calculated. Hence, the gene probes were arranged in ascending order of the numerical values and evaluated. Note that multiple probes were synthesized and placed on one gene in the Array in some cases. Accordingly, for a single gene, the smallest numerical value among numerical values calculated by these methods was selected, and the other values were excluded. Tables 16 to 32 show genes evaluated as having expression variations equivalent to or smaller than β-actin from the analysis result thus obtained. Tables 16 to 19 show a total of 243 genes identified by the method 1. Tables 20 to 26 show a total of 377 genes identified by the method 2. Tables 27 to 32 show a total of 330 genes identified by the method 3.

TABLE 16

| Rank | ID | Gene symbol |
|---|---|---|
| 1 | 6428 | SRSF3 |
| 2 | 7170 | TPM3 |
| 3 | 23435 | TARDBP |
| 4 | 7756 | ZNF207 |
| 5 | 7702 | ZNF143 |
| 6 | 9698 | PUM1 |
| 7 | 5861 | RAB1A |
| 8 | 149013 | LOC101059961 |
| 9 | 54778 | RNF111 |
| 10 | 1665 | DHX15 |
| 11 | 51663 | ZFR |
| 12 | 10236 | HNRNPR |
| 13 | 9813 | EFCAB14 |
| 14 | 65117 | RSRC2 |
| 15 | 5725 | MIR4745 |
| 16 | 155435 | RBM33 |
| 17 | 55252 | ASXL2 |
| 18 | 1655 | DDX5 |
| 19 | 1982 | EIF4G2 |
| 20 | 10978 | CLP1 |
| 21 | 3032 | HADHB |
| 22 | 3190 | HNRNPK |
| 23 | 6791 | AURKAPS1 |
| 24 | 6434 | TRA2B |
| 25 | 25912 | C1orf43 |
| 26 | 5757 | PTMA |
| 27 | 3312 | HSPA8 |
| 28 | 54925 | ZSCAN32 |
| 29 | 10664 | CTCF |
| 30 | 54617 | INO80 |
| 31 | 11315 | PARK7 |
| 32 | 23451 | SF3B1 |
| 33 | 9555 | H2AFY |
| 34 | 9969 | MED13 |
| 35 | 23787 | MTCH1 |
| 36 | 9782 | MATR3 |
| 37 | 57142 | RTN4 |
| 38 | 9877 | LOC441155 |
| 39 | 5685 | PSMA4 |
| 40 | 51441 | YTHDF2 |
| 41 | 10657 | KHDRBS1 |
| 42 | 4735 | SEPT2 |
| 43 | 4841 | NONO |
| 44 | 5781 | PTPN11 |
| 45 | 8943 | AP3D1 |
| 46 | 6726 | SRP9 |
| 47 | 10513 | APPBP2 |
| 48 | 26003 | GORASP2 |
| 49 | 23131 | GPATCH8 |
| 50 | 9318 | COPS2 |
| 51 | 387082 | SUMO4 |
| 52 | 57551 | TAOK1 |
| 53 | 6651 | SON |

TABLE 16-continued

| Rank | ID | Gene symbol |
|---|---|---|
| 54 | 79893 | GGNBP2 |
| 55 | 9673 | SLC25A44 |
| 56 | 26092 | TOR1AIP1 |
| 57 | 6613 | SUMO2 |
| 58 | 6015 | RING1 |
| 59 | 11052 | CPSF6 |
| 60 | 57117 | INTS12 |

TABLE 17

| Rank | ID | Gene symbol |
|---|---|---|
| 61 | 55041 | PLEKHB2 |
| 62 | 5250 | SLC25A3 |
| 63 | 51534 | VTA1 |
| 64 | 5689 | PSMB1 |
| 65 | 1213 | CLTC |
| 66 | 4946 | OAZ1 |
| 67 | 56889 | TM9SF3 |
| 68 | 10521 | DDX17 |
| 69 | 2885 | GRB2 |
| 70 | 6128 | RPL6 |
| 71 | 7009 | TMBIM6 |
| 72 | 829 | CAPZA1 |
| 73 | 79595 | SAP130 |
| 74 | 821 | CANX |
| 75 | 9802 | DAZAP2 |
| 76 | 9733 | SART3 |
| 77 | 127933 | UHMK1 |
| 78 | 7532 | YWHAG |
| 79 | 11021 | RAB35 |
| 80 | 10730 | YME1L1 |
| 81 | 25949 | SYF2 |
| 82 | 54878 | DPP8 |
| 83 | 83440 | ADPGK |
| 84 | 11108 | PRDM4 |
| 85 | 9741 | LAPTM4A |
| 86 | 54980 | C2orf42 |
| 87 | 54859 | ELP6 |
| 88 | 6427 | MIR636 |
| 89 | 10096 | ACTR3 |
| 90 | 9643 | MORF4L2 |
| 91 | 9774 | BCLAF1 |
| 92 | 23196 | FAM120A |
| 93 | 64746 | ACBD3 |
| 94 | 3020 | H3F3A |
| 95 | 9736 | USP34 |
| 96 | 7341 | SUMO1 |
| 97 | 5528 | PPP2R5D |
| 98 | 10971 | YWHAQ |
| 99 | 85369 | STRIP1 |
| 100 | 51478 | HSD17B7 |
| 101 | 387338 | NSUN4 |
| 102 | 3183 | HNRNPC |
| 103 | 2130 | EWSR1 |
| 104 | 6129 | RPL7 |
| 105 | 55802 | DCP1A |
| 106 | 2959 | GTF2B |
| 107 | 71 | ACTG1 |
| 108 | 989 | SEPT7 |
| 109 | 57148 | RALGAPB |
| 110 | 6155 | RPL27 |
| 111 | 23061 | TBC1D9B |
| 112 | 54764 | ZRANB1 |
| 113 | 23429 | RYBP |
| 114 | 4144 | MAT2A |
| 115 | 9443 | MED7 |
| 116 | 7334 | UBE2N |
| 117 | 6433 | SFSWAP |
| 118 | 9857 | CEP350 |
| 119 | 10933 | MORF4L1 |
| 120 | 4637 | MYL6 |

TABLE 18

| Rank | ID | Gene symbol |
|---|---|---|
| 121 | 55334 | SLC39A9 |
| 122 | 4899 | NRF1 |
| 123 | 54870 | QRICH1 |
| 124 | 9416 | DDX23 |
| 125 | 81573 | ANKRD13C |
| 126 | 23054 | NCOA6 |
| 127 | 55249 | YY1AP1 |
| 128 | 129831 | RBM45 |
| 129 | 56829 | ZC3HAV1 |
| 130 | 89910 | UBE3B |
| 131 | 27249 | MMADHC |
| 132 | 378 | ARF4 |
| 133 | 114882 | OSBPL8 |
| 134 | 92400 | RBM18 |
| 135 | 7343 | UBTF |
| 136 | 5683 | PSMA2 |
| 137 | 3838 | KPNA2 |
| 138 | 9093 | DNAJA3 |
| 139 | 10376 | TUBA1B |
| 140 | 3184 | HNRNPD |
| 141 | 9794 | MAML1 |
| 142 | 9320 | TRIP12 |
| 143 | 728558 | ENTPD1-AS1 |
| 144 | 10209 | EIF1 |
| 145 | 23478 | SEC11A |
| 146 | 7874 | USP7 |
| 147 | 3015 | H2AFZ |
| 148 | 2767 | GNA11 |
| 149 | 9689 | BZW1 |
| 150 | 9815 | GIT2 |
| 151 | 26058 | GIGYF2 |
| 152 | 10658 | CELF1 |
| 153 | 54499 | TMCO1 |
| 154 | 55729 | ATF7IP |
| 155 | 4236 | MFAP1 |
| 156 | 7150 | TOP1 |
| 157 | 5682 | PSMA1 |
| 158 | 23041 | MON2 |
| 159 | 2186 | BPTF |
| 160 | 5725 | PTBP1 |
| 161 | 1398 | CRK |
| 162 | 26123 | TCTN3 |
| 163 | 10618 | TGOLN2 |
| 164 | 9711 | KIAA0226 |
| 165 | 9474 | ATG5 |
| 166 | 79188 | TMEM43 |
| 167 | 10694 | CCT8 |
| 168 | 9584 | RBM39 |
| 169 | 51699 | VPS29 |
| 170 | 55145 | THAP1 |
| 171 | 79803 | HPS6 |
| 172 | 25942 | SIN3A |
| 173 | 1973 | EIF4A1 |
| 174 | 23 | ABCF1 |
| 175 | 4170 | MCL1 |
| 176 | 10691 | GMEB1 |
| 177 | 9667 | SAFB2 |
| 178 | 498 | ATP5A1 |
| 179 | 93621 | MRFAP1 |
| 180 | 6924 | TCEB3 |

TABLE 19

| Rank | ID | Gene symbol |
|---|---|---|
| 181 | 6500 | SKP1 |
| 182 | 9567 | GTPBP1 |
| 183 | 54850 | FBXL12 |
| 184 | 64786 | TBC1D15 |
| 185 | 253143 | PRR14L |
| 186 | 203245 | NAIF1 |
| 187 | 55709 | KBTBD4 |
| 188 | 5501 | PPP1CC |
| 189 | 11335 | CBX3 |
| 190 | 23383 | MAU2 |

TABLE 19-continued

| Rank | ID | Gene symbol |
|---|---|---|
| 191 | 9184 | BUB3 |
| 192 | 51343 | FZR1 |
| 193 | 2665 | GDI2 |
| 194 | 64429 | ZDHHC6 |
| 195 | 80196 | RNF34 |
| 196 | 8874 | ARHGEF7 |
| 197 | 9191 | DEDD |
| 198 | 51742 | ARID4B |
| 199 | 5511 | PPP1R8 |
| 200 | 64853 | AIDA |
| 201 | 9851 | KIAA0753 |
| 202 | 4292 | MLH1 |
| 203 | 57634 | EP400 |
| 204 | 10228 | STX6 |
| 205 | 8763 | CD164 |
| 206 | 2800 | GOLGA1 |
| 207 | 6191 | RPS4X |
| 208 | 23204 | ARL6IP1 |
| 209 | 54788 | DNAJB12 |
| 210 | 56252 | YLPM1 |
| 211 | 84961 | FBXL20 |
| 212 | 57693 | ZNF317 |
| 213 | 1642 | DDB1 |
| 214 | 10728 | PTGES3 |
| 215 | 8621 | CDK13 |
| 216 | 30000 | TNPO2 |
| 217 | 10147 | SUGP2 |
| 218 | 84146 | LOC100996620 |
| 219 | 54516 | MTRF1L |
| 220 | 23759 | PPIL2 |
| 221 | 7514 | XPO1 |
| 222 | 5594 | MAPK1 |
| 223 | 6418 | SET |
| 224 | 51434 | ANAPC7 |
| 225 | 9570 | GOSR2 |
| 226 | 10857 | PGRMC1 |
| 227 | 6217 | RPS16 |
| 228 | 8890 | EIF2B4 |
| 229 | 55233 | MOB1A |
| 230 | 7529 | YWHAB |
| 231 | 55109 | AGGF1 |
| 232 | 65056 | GPBP1 |
| 233 | 51622 | CCZ1 |
| 234 | 8841 | HDAC3 |
| 235 | 23760 | PITPNB |
| 236 | 801 | CALM1 |
| 237 | 4947 | OAZ2 |
| 238 | 6188 | RPS3 |
| 239 | 84138 | SLC7A6OS |
| 240 | 81545 | FBXO38 |
| 241 | 905 | CCNT2 |
| 242 | 57794 | SUGP1 |
| 243 | 51138 | COPS4 |

TABLE 20

| Rank | ID | Gene symbol |
|---|---|---|
| 1 | 6428 | SRSF3 |
| 2 | 55252 | ASXL2 |
| 3 | 23451 | SF3B1 |
| 4 | 65117 | RSRC2 |
| 5 | 1655 | DDX5 |
| 6 | 51663 | ZFR |
| 7 | 83440 | ADPGK |
| 8 | 26003 | GORASP2 |
| 9 | 5757 | PTMA |
| 10 | 1213 | CLTC |
| 11 | 54778 | RNF111 |
| 12 | 5250 | SLC25A3 |
| 13 | 7170 | TPM3 |
| 14 | 149013 | LOC101059961 |
| 15 | 7702 | ZNF143 |
| 16 | 1982 | EIF4G2 |
| 17 | 54617 | INO80 |

TABLE 20-continued

| Rank | ID | Gene symbol |
|---|---|---|
| 18 | 23435 | TARDBP |
| 19 | 5861 | RAB1A |
| 20 | 6613 | SUMO2 |
| 21 | 124491 | TMEM170A |
| 22 | 3312 | HSPA8 |
| 23 | 5528 | PPP2R5D |
| 24 | 6427 | MIR636 |
| 25 | 3032 | HADHB |
| 26 | 9698 | PUM1 |
| 27 | 10657 | KHDRBS1 |
| 28 | 155435 | RBM33 |
| 29 | 7756 | ZNF207 |
| 30 | 9969 | MED13 |
| 31 | 10521 | DDX17 |
| 32 | 10236 | HNRNPR |
| 33 | 11315 | PARK7 |
| 34 | 9584 | RBM39 |
| 35 | 9643 | MORF4L2 |
| 36 | 25912 | C1orf43 |
| 37 | 51441 | YTHDF2 |
| 38 | 9802 | DAZAP2 |
| 39 | 9673 | SLC25A44 |
| 40 | 10728 | PTGES3 |
| 41 | 10914 | PAPOLA |
| 42 | 1665 | DHX15 |
| 43 | 4899 | NRF1 |
| 44 | 5685 | PSMA4 |
| 45 | 6132 | RPL8 |
| 46 | 3184 | HNRNPD |
| 47 | 6791 | AURKAPS1 |
| 48 | 54925 | ZSCAN32 |
| 49 | 9987 | HNRNPDL |
| 50 | 57551 | TAOK1 |
| 51 | 4848 | CNOT2 |
| 52 | 10978 | CLP1 |
| 53 | 84081 | NSRP1 |
| 54 | 9555 | H2AFY |
| 55 | 9877 | LOC441155 |
| 56 | 4841 | NONO |
| 57 | 8763 | CD164 |
| 58 | 79893 | GGNBP2 |
| 59 | 79595 | SAP130 |
| 60 | 4236 | MFAP1 |

TABLE 21

| Rank | ID | Gene symbol |
|---|---|---|
| 61 | 23054 | NCOA6 |
| 62 | 3190 | HNRNPK |
| 63 | 4144 | MAT2A |
| 64 | 3020 | H3F3A |
| 65 | 11108 | PRDM4 |
| 66 | 23633 | KPNA6 |
| 67 | 4170 | MCL1 |
| 68 | 23131 | GPATCH8 |
| 69 | 4706 | NDUFAB1 |
| 70 | 55041 | PLEKHB2 |
| 71 | 23478 | SEC11A |
| 72 | 7009 | TMBIM6 |
| 73 | 11052 | CPSF6 |
| 74 | 25949 | SYF2 |
| 75 | 6651 | SON |
| 76 | 54850 | FBXL12 |
| 77 | 54971 | BANP |
| 78 | 55181 | SMG8 |
| 79 | 127933 | UHMK1 |
| 80 | 6434 | TRA2B |
| 81 | 4946 | OAZ1 |
| 82 | 4735 | SEPT2 |
| 83 | 51534 | VTA1 |
| 84 | 4292 | MLH1 |
| 85 | 23326 | USP22 |
| 86 | 57038 | RARS2 |
| 87 | 5781 | PTPN11 |

TABLE 21-continued

| Rank | ID | Gene symbol |
|---|---|---|
| 88 | 989 | SEPT7 |
| 89 | 6738 | TROVE2 |
| 90 | 25972 | UNC50 |
| 91 | 3015 | H2AFZ |
| 92 | 23215 | PRRC2C |
| 93 | 51097 | CCZ1 |
| 94 | 829 | CAPZA1 |
| 95 | 57142 | RTN4 |
| 96 | 55233 | MOB1A |
| 97 | 55656 | INTS8 |
| 98 | 23510 | KCTD2 |
| 99 | 51478 | HSD17B7 |
| 100 | 7189 | TRAF6 |
| 101 | 26092 | TOR1AIP1 |
| 102 | 10989 | IMMT |
| 103 | 91445 | RNF185 |
| 104 | 55249 | YY1AP1 |
| 105 | 9733 | SART3 |
| 106 | 5689 | PSMB1 |
| 107 | 57794 | SUGP1 |
| 108 | 1642 | DDB1 |
| 109 | 51499 | TRIAP1 |
| 110 | 9577 | BRE |
| 111 | 79005 | SCNM1 |
| 112 | 55334 | SLC39A9 |
| 113 | 9730 | VPRBP |
| 114 | 51204 | TACO1 |
| 115 | 55628 | ZNF407 |
| 116 | 7341 | SUMO1 |
| 117 | 4947 | OAZ2 |
| 118 | 64746 | ACBD3 |
| 119 | 54878 | DPP8 |
| 120 | 80196 | RNF34 |

TABLE 22

| Rank | ID | Gene symbol |
|---|---|---|
| 121 | 9782 | MATR3 |
| 122 | 7529 | YWHAB |
| 123 | 6433 | SFSWAP |
| 124 | 147007 | MIR4723 |
| 125 | 54764 | ZRANB1 |
| 126 | 51068 | NMD3 |
| 127 | 7874 | USP7 |
| 128 | 23787 | MTCH1 |
| 129 | 63892 | THADA |
| 130 | 10238 | DCAF7 |
| 131 | 8890 | EIF2B4 |
| 132 | 23014 | FBXO21 |
| 133 | 6426 | SRSF1 |
| 134 | 10933 | MORF4L1 |
| 135 | 100996930 | LINC00621 |
| 136 | 10228 | STX6 |
| 137 | 57532 | NUFIP2 |
| 138 | 7385 | UQCRC2 |
| 139 | 9774 | BCLAF1 |
| 140 | 387082 | SUMO4 |
| 141 | 54467 | ANKIB1 |
| 142 | 55288 | RHOT1 |
| 143 | 22919 | MAPRE1 |
| 144 | 29855 | UBN1 |
| 145 | 9567 | GTPBP1 |
| 146 | 57470 | LRRC47 |
| 147 | 51742 | ARID4B |
| 148 | 85369 | STRIP1 |
| 149 | 5594 | MAPK1 |
| 150 | 57148 | RALGAPB |
| 151 | 51138 | COPS4 |
| 152 | 5501 | PPP1CC |
| 153 | 54471 | SMCR7L |
| 154 | 65992 | DDRGK1 |
| 155 | 55471 | NDUFAF7 |
| 156 | 57693 | ZNF317 |
| 157 | 9527 | GOSR1 |

TABLE 22-continued

| Rank | ID | Gene symbol |
|---|---|---|
| 158 | 54883 | CWC25 |
| 159 | 164 | AP1G1 |
| 160 | 5683 | PSMA2 |
| 161 | 2186 | BPTF |
| 162 | 93621 | MRFAP1 |
| 163 | 3183 | HNRNPC |
| 164 | 567 | B2M |
| 165 | 5725 | MIR4745 |
| 166 | 3454 | IFNAR1 |
| 167 | 253143 | PRR14L |
| 168 | 751 4 | XPO1 |
| 169 | 9857 | CEP350 |
| 170 | 51699 | VPS29 |
| 171 | 387 | RHOA |
| 172 | 29123 | ANKRD11 |
| 173 | 57002 | YAE1D1 |
| 174 | 6155 | RPL27 |
| 175 | 6128 | RPL6 |
| 176 | 23394 | ADNP |
| 177 | 2767 | GNA11 |
| 178 | 8034 | SLC25A16 |
| 179 | 6129 | RPL7 |
| 180 | 2885 | GRB2 |

TABLE 23

| Rank | ID | Gene symbol |
|---|---|---|
| 181 | 55716 | LMBR1L |
| 182 | 10147 | SUGP2 |
| 183 | 57117 | INTS12 |
| 184 | 5692 | PSMB4 |
| 185 | 10130 | PDIA6 |
| 186 | 23196 | FAM120A |
| 187 | 7319 | UBE2A |
| 188 | 253260 | RICTOR |
| 189 | 2959 | GTF2B |
| 190 | 10658 | CELF1 |
| 191 | 7266 | DNAJC7 |
| 192 | 54458 | PRR13 |
| 193 | 9967 | THRAP3 |
| 194 | 27069 | GHITM |
| 195 | 7343 | UBTF |
| 196 | 55729 | ATF7IP |
| 197 | 6731 | SRP72 |
| 198 | 6083 | RPL5 |
| 199 | 10591 | GMEB1 |
| 200 | 27249 | MMADHC |
| 201 | 11276 | SYNRG |
| 202 | 23759 | PPIL2 |
| 203 | 10376 | TUBA1B |
| 204 | 8315 | BRAP |
| 205 | 55967 | NDUFA12 |
| 206 | 27327 | TNRC6A |
| 207 | 119504 | ANAPC16 |
| 208 | 26056 | RAB11FIP5 |
| 209 | 51322 | WAC |
| 210 | 10971 | YWHAQ |
| 211 | 64429 | ZDHHC6 |
| 212 | 26065 | LSM14A |
| 213 | 51611 | DPH5 |
| 214 | 5660 | PSAP |
| 215 | 91603 | ZNF830 |
| 216 | 7150 | TOP1 |
| 217 | 10479 | SLC9A6 |
| 218 | 6829 | SUPT5H |
| 219 | 55164 | SHQ1 |
| 220 | 55810 | FOXJ2 |
| 221 | 51538 | ZCCHC17 |
| 222 | 1973 | EIF4A1 |
| 223 | 9184 | BUB3 |
| 224 | 7536 | SF1 |
| 225 | 5193 | PEX12 |
| 226 | 9477 | MED20 |
| 227 | 23383 | MAU2 |

TABLE 23-continued

| Rank | ID | Gene symbol |
|---|---|---|
| 228 | 79169 | C1orf35 |
| 229 | 114659 | LRRC37B |
| 230 | 79699 | ZYG11B |
| 231 | 2802 | GOLGA3 |
| 232 | 57102 | C12orf4 |
| 233 | 950 | SCARB2 |
| 234 | 9815 | GIT2 |
| 235 | 26130 | GAPVD1 |
| 236 | 10209 | EIF1 |
| 237 | 55660 | PRPF40A |
| 238 | 5298 | PI4KB |
| 239 | 92335 | STRADA |
| 240 | 7532 | YWHAG |

TABLE 24

| Rank | ID | Gene symbol |
|---|---|---|
| 241 | 51434 | ANAPC7 |
| 242 | 79939 | SLC35E1 |
| 243 | 6603 | SMARCD2 |
| 244 | 55852 | TEX2 |
| 245 | 9741 | LAPTM4A |
| 246 | 10735 | STAG2 |
| 247 | 29072 | SETD2 |
| 248 | 8897 | MTMR3 |
| 249 | 10664 | CTCF |
| 250 | 2801 | GOLGA2 |
| 251 | 64786 | TBC1D15 |
| 252 | 57109 | REXO4 |
| 253 | 7334 | UBE2N |
| 254 | 11011 | TLK2 |
| 255 | 4637 | MYL6 |
| 256 | 9711 | KIAA0226 |
| 257 | 81573 | ANKRD13C |
| 258 | 9416 | DDX23 |
| 259 | 9169 | SCAF11 |
| 260 | 8943 | AP3D1 |
| 261 | 54870 | QRICH1 |
| 262 | 9255 | AIMP1 |
| 263 | 7109 | TRAPPC10 |
| 264 | 23386 | NUDCD3 |
| 265 | 8567 | MADD |
| 266 | 339448 | C1orf174 |
| 267 | 8773 | SNAP23 |
| 268 | 9693 | RAPGEF2 |
| 269 | 23063 | WAPAL |
| 270 | 11153 | FICD |
| 271 | 6185 | RPN2 |
| 272 | 1974 | EIF4A2 |
| 273 | 23192 | ATG4B |
| 274 | 71 | ACTG1 |
| 275 | 6879 | TAF7 |
| 276 | 801 | CALM1 |
| 277 | 9919 | SEC16A |
| 278 | 22984 | PDCD11 |
| 279 | 9647 | PPM1F |
| 280 | 51247 | PAIP2 |
| 281 | 9570 | GOSR2 |
| 282 | 162427 | FAM134C |
| 283 | 5609 | MAP2K7 |
| 284 | 147179 | WIPF2 |
| 285 | 51188 | SS18L2 |
| 286 | 728558 | ENTPD1-AS1 |
| 287 | 79086 | SMIM7 |
| 288 | 65056 | GPBP1 |
| 289 | 4771 | NF2 |
| 290 | 57130 | ATP13A1 |
| 291 | 27229 | TUBGCP4 |
| 292 | 7988 | ZNF212 |
| 293 | 7727 | ZNF174 |
| 294 | 79074 | C2orf49 |
| 295 | 821 | CANX |
| 296 | 85451 | UNK |
| 297 | 22930 | RAB3GAP1 |

TABLE 24-continued

| Rank | ID | Gene symbol |
|---|---|---|
| 298 | 51634 | RBMX2 |
| 299 | 56658 | TRIM39 |
| 300 | 9667 | SAFB2 |

TABLE 25

| Rank | ID | Gene symbol |
|---|---|---|
| 301 | 1487 | CTBP1 |
| 302 | 55207 | ARL8B |
| 303 | 5936 | RBM14-RBM4 |
| 304 | 55585 | UBE2Q1 |
| 305 | 1398 | CRK |
| 306 | 27072 | VPS41 |
| 307 | 55173 | MRPS10 |
| 308 | 3065 | HDAC1 |
| 309 | 9827 | RGP1 |
| 310 | 55737 | VPS35 |
| 311 | 53339 | BTBD1 |
| 312 | 55578 | SUPT20H |
| 313 | 6468 | FBXW4 |
| 314 | 103910 | MYL12B |
| 315 | 10923 | SUB1 |
| 316 | 56829 | ZC3HAV1 |
| 317 | 55830 | GLT8D1 |
| 318 | 49854 | ZBTB21 |
| 319 | 1915 | EEF1A1 |
| 320 | 10575 | CCT4 |
| 321 | 23061 | TBC1D9B |
| 322 | 2286 | FKBP2 |
| 323 | 23760 | PITPNB |
| 324 | 9794 | MAML1 |
| 325 | 51490 | C9orf114 |
| 326 | 54516 | MTRF1L |
| 327 | 8899 | PRPF4B |
| 328 | 79676 | OGFOD2 |
| 329 | 11165 | NUDT3 |
| 330 | 92400 | RBM18 |
| 331 | 51652 | CHMP3 |
| 332 | 6015 | RING1 |
| 333 | 57673 | BEND3 |
| 334 | 54205 | CYCS |
| 335 | 1315 | COPB1 |
| 336 | 255812 | SDHAP1 |
| 337 | 4682 | NUBP1 |
| 338 | 80207 | OPA3 |
| 339 | 84187 | TMEM164 |
| 340 | 85021 | REPS1 |
| 341 | 4649 | MYO9A |
| 342 | 22796 | COG2 |
| 343 | 3033 | HADH |
| 344 | 2800 | GOLGA1 |
| 345 | 6670 | SP3 |
| 346 | 23369 | PUM2 |
| 347 | 148479 | PHF13 |
| 348 | 23013 | SPEN |
| 349 | 51755 | CDK12 |
| 350 | 23592 | LEMD3 |
| 351 | 2969 | GTF2I |
| 352 | 1937 | EEF1G |
| 353 | 84236 | RHBDD1 |
| 354 | 23660 | ZKSCAN5 |
| 355 | 23211 | ZC3H4 |
| 356 | 9922 | IQSEC1 |
| 357 | 114883 | OSBPL9 |
| 358 | 55193 | PBRM1 |
| 359 | 23167 | EFR3A |
| 360 | 56957 | OTUD7B |

TABLE 26

| Rank | ID | Gene symbol |
|---|---|---|
| 361 | 285521 | COX18 |
| 362 | 10944 | C11orf58 |
| 363 | 64427 | TTC31 |
| 364 | 9960 | USP3 |
| 365 | 55920 | RCC2 |
| 366 | 1108 | CHD4 |
| 367 | 55681 | SCYL2 |
| 368 | 4594 | MUT |
| 369 | 9183 | ZW10 |
| 370 | 10513 | APPBP2 |
| 371 | 23429 | RYBP |
| 372 | 54433 | GAR1 |
| 373 | 132949 | AASDH |
| 374 | 51808 | PHAX |
| 375 | 56623 | INPP5E |
| 376 | 55527 | FEM1A |
| 377 | 54499 | TMCO1 |

TABLE 27

| Rank | ID | Gene symbol |
|---|---|---|
| 1 | 6428 | SRSF3 |
| 2 | 7170 | TPM3 |
| 3 | 7702 | ZNF143 |
| 4 | 7756 | ZNF207 |
| 5 | 9698 | PUM1 |
| 6 | 5861 | RAB1A |
| 7 | 65117 | RSRC2 |
| 8 | 51663 | ZFR |
| 9 | 149013 | LOC101059961 |
| 10 | 54925 | ZSCAN32 |
| 11 | 1982 | EIF4G2 |
| 12 | 54778 | RNF111 |
| 13 | 23435 | TARDBP |
| 14 | 10236 | HNRNPR |
| 15 | 1665 | DHX15 |
| 16 | 11315 | PARK7 |
| 17 | 10978 | CLP1 |
| 18 | 9555 | H2AFY |
| 19 | 9969 | MED13 |
| 20 | 5725 | MIR4745 |
| 21 | 55252 | ASXL2 |
| 22 | 4841 | NONO |
| 23 | 25912 | C1orf43 |
| 24 | 10664 | CTCF |
| 25 | 10657 | KHDRBS1 |
| 26 | 3032 | HADHB |
| 27 | 9877 | LOC441155 |
| 28 | 51478 | HSD17B7 |
| 29 | 23131 | GPATCH8 |
| 30 | 6434 | TRA2B |
| 31 | 1655 | DDX5 |
| 32 | 11052 | CPSF6 |
| 33 | 9802 | DAZAP2 |
| 34 | 5689 | PSMB1 |
| 35 | 3183 | HNRNPC |
| 36 | 3190 | HNRNPK |
| 37 | 3312 | HSPA8 |
| 38 | 155435 | RBM33 |
| 39 | 1213 | CLTC |
| 40 | 26003 | GORASP2 |
| 41 | 9813 | EFCAB14 |
| 42 | 5250 | SLC25A3 |
| 43 | 387082 | SUMO4 |
| 44 | 6726 | SRP9 |
| 45 | 23451 | SF3B1 |
| 46 | 10521 | DDX17 |
| 47 | 9643 | MORF4L2 |
| 48 | 9673 | SLC25A44 |
| 49 | 23196 | FAM120A |
| 50 | 54617 | INO80 |
| 51 | 9782 | MATR3 |
| 52 | 6015 | RING1 |
| 53 | 6651 | SON |

TABLE 27-continued

| Rank | ID | Gene symbol |
|---|---|---|
| 54 | 57117 | INTS12 |
| 55 | 51441 | YTHDF2 |
| 56 | 111008 | PRDM4 |
| 57 | 51534 | VTA1 |
| 58 | 9857 | CEP350 |
| 59 | 25949 | SYF2 |
| 60 | 11021 | RAB35 |

TABLE 28

| Rank | ID | Gene symbol |
|---|---|---|
| 61 | 79893 | GGNBP2 |
| 62 | 55041 | PLEKHB2 |
| 63 | 8943 | AP3D1 |
| 64 | 3184 | HNRNPD |
| 65 | 829 | CAPZA1 |
| 66 | 10376 | TUBA1B |
| 67 | 5528 | PPP2R5D |
| 68 | 10971 | YWHAQ |
| 69 | 4946 | OAZ1 |
| 70 | 9774 | BCLAF1 |
| 71 | 10228 | STX6 |
| 72 | 7874 | USP7 |
| 73 | 6427 | MIR636 |
| 74 | 10933 | MORF4L1 |
| 75 | 51699 | VPS29 |
| 76 | 57551 | TAOK1 |
| 77 | 54859 | ELP6 |
| 78 | 57142 | RTN4 |
| 79 | 79595 | SAP130 |
| 80 | 9733 | SART3 |
| 81 | 2130 | EWSR1 |
| 82 | 989 | SEPT7 |
| 83 | 64746 | ACBD3 |
| 84 | 26092 | TOR1AIP1 |
| 85 | 5781 | PTPN11 |
| 86 | 55334 | SLC39A9 |
| 87 | 4144 | MAT2A |
| 88 | 127933 | UHMK1 |
| 89 | 9567 | GTPBP1 |
| 90 | 92400 | RBM18 |
| 91 | 5685 | PSMA4 |
| 92 | 23061 | TBC1D9B |
| 93 | 6791 | AURKAPS1 |
| 94 | 10658 | CELF1 |
| 95 | 85369 | STRIP1 |
| 96 | 6613 | SUMO2 |
| 97 | 9741 | LAPTM4A |
| 98 | 6426 | SRSF1 |
| 99 | 55249 | YY1AP1 |
| 100 | 51742 | ARID4B |
| 101 | 23215 | PRRC2C |
| 102 | 6924 | TCEB3 |
| 103 | 4735 | SEPT2 |
| 104 | 9416 | DDX23 |
| 105 | 7334 | UBE2N |
| 106 | 4637 | MYL6 |
| 107 | 64429 | ZDHHC6 |
| 108 | 6124 | RPL4 |
| 109 | 23054 | NCOA6 |
| 110 | 10728 | PTGES3 |
| 111 | 6738 | TROVE2 |
| 112 | 9318 | COPS2 |
| 113 | 5725 | PTBP1 |
| 114 | 4899 | NRF1 |
| 115 | 54980 | C2orf42 |
| 116 | 5594 | MAPK1 |
| 117 | 7009 | TMBIM6 |
| 118 | 54878 | DPP8 |
| 119 | 10096 | ACTR3 |
| 120 | 114882 | OSBPL8 |

TABLE 29

| Rank | ID | Gene symbol |
|---|---|---|
| 121 | 6128 | RPL6 |
| 122 | 26058 | GIGYF2 |
| 123 | 54764 | ZRANB1 |
| 124 | 9570 | GOSR2 |
| 125 | 51611 | DPH5 |
| 126 | 7343 | UBTF |
| 127 | 56829 | ZC3HAV1 |
| 128 | 7529 | YWHAB |
| 129 | 10694 | CCT8 |
| 130 | 5757 | PTMA |
| 131 | 1487 | CTBP1 |
| 132 | 6129 | RPL7 |
| 133 | 9443 | MED7 |
| 134 | 23787 | MTCH1 |
| 135 | 55233 | MOB1A |
| 136 | 23760 | PITPNB |
| 137 | 498 | ATP5A1 |
| 138 | 221302 | ZUFSP |
| 139 | 81573 | ANKRD13C |
| 140 | 8763 | CD164 |
| 141 | 2885 | GRB2 |
| 142 | 10147 | SUGP2 |
| 143 | 55181 | SMG8 |
| 144 | 1642 | DDB1 |
| 145 | 9794 | MAML1 |
| 146 | 23383 | MAU2 |
| 147 | 10209 | EIF1 |
| 148 | 2800 | GOLGA1 |
| 149 | 4771 | NF2 |
| 150 | 8890 | EIF2B4 |
| 151 | 4236 | MFAP1 |
| 152 | 23063 | WAPAL |
| 153 | 23167 | EFR3A |
| 154 | 2186 | BPTF |
| 155 | 54870 | QRICH1 |
| 156 | 4682 | NUBP1 |
| 157 | 56252 | YLPM1 |
| 158 | 27249 | MMADHC |
| 159 | 10730 | YME1L1 |
| 160 | 1973 | EIF4A1 |
| 161 | 9584 | RBM39 |
| 162 | 8621 | CDK13 |
| 163 | 91603 | ZNF830 |
| 164 | 55164 | SHQ1 |
| 165 | 10735 | STAG2 |
| 166 | 2767 | GNA11 |
| 167 | 80196 | RNF34 |
| 168 | 56658 | TRIM39 |
| 169 | 129831 | RBM45 |
| 170 | 4947 | OAZ2 |
| 171 | 81545 | FBXO38 |
| 172 | 89910 | UBE3B |
| 173 | 9711 | KIAA0226 |
| 174 | 10989 | IMMT |
| 175 | 79803 | HPS6 |
| 176 | 11313 | LYPLA2 |
| 177 | 23211 | ZC3H4 |
| 178 | 2665 | GDI2 |
| 179 | 6433 | SFSWAP |
| 180 | 23041 | MON2 |

TABLE 30

| Rank | ID | Gene symbol |
|---|---|---|
| 181 | 10440 | TIMM17A |
| 182 | 93621 | MRFAP1 |
| 183 | 23013 | SPEN |
| 184 | 3838 | KPNA2 |
| 185 | 71 | ACTG1 |
| 186 | 55628 | ZNF407 |
| 187 | 84790 | TUBA1C |
| 188 | 2969 | GTF2I |
| 189 | 821 | CANX |
| 190 | 10277 | UBE4B |

TABLE 30-continued

| Rank | ID | Gene symbol |
|---|---|---|
| 191 | 11102 | RPP14 |
| 192 | 378 | ARF4 |
| 193 | 56478 | EIF4ENIF1 |
| 194 | 25942 | SIN3A |
| 195 | 9184 | BUB3 |
| 196 | 7150 | TOP1 |
| 197 | 203245 | NAIF1 |
| 198 | 10270 | AKAP8 |
| 199 | 10238 | DCAF7 |
| 200 | 51138 | COPS4 |
| 201 | 5511 | PPP1R8 |
| 202 | 6083 | RPL5 |
| 203 | 10691 | GMEB1 |
| 204 | 147007 | MIR4723 |
| 205 | 6418 | SET |
| 206 | 9736 | USP34 |
| 207 | 23 | ABCF1 |
| 208 | 23204 | ARL6IP1 |
| 209 | 84138 | SLC7A6OS |
| 210 | 65056 | GPBP1 |
| 211 | 11034 | DSTN |
| 212 | 8841 | HDAC3 |
| 213 | 6500 | SKP1 |
| 214 | 54205 | CYCS |
| 215 | 6767 | ST13 |
| 216 | 5501 | PPP1CC |
| 217 | 54516 | MTRF1L |
| 218 | 55898 | UNC45A |
| 219 | 64853 | AIDA |
| 220 | 5683 | PSMA2 |
| 221 | 9689 | BZW1 |
| 222 | 2801 | GOLGA2 |
| 223 | 23518 | R3HDM1 |
| 224 | 905 | CCNT2 |
| 225 | 4238 | MFAP3 |
| 226 | 9815 | GIT2 |
| 227 | 79699 | ZYG11B |
| 228 | 253143 | PRR14L |
| 229 | 9960 | USP3 |
| 230 | 83440 | ADPGK |
| 231 | 3146 | HMGB1 |
| 232 | 1937 | EEF1G |
| 233 | 11335 | CBX3 |
| 234 | 55527 | FEM1A |
| 235 | 55776 | SAYSD1 |
| 236 | 26135 | SERBP1 |
| 237 | 9093 | DNAJA3 |
| 238 | 10137 | RBM12 |
| 239 | 23429 | RYBP |
| 240 | 3015 | H2AFZ |

TABLE 31

| Rank | ID | Gene symbol |
|---|---|---|
| 241 | 79086 | SMIM7 |
| 242 | 22919 | MAPRE1 |
| 243 | 6188 | RPS3 |
| 244 | 3182 | HNRNPAB |
| 245 | 23394 | ADNP |
| 246 | 6468 | FBXW4 |
| 247 | 84146 | LOC100996620 |
| 248 | 51622 | CCZ1 |
| 249 | 387032 | ZKSCAN4 |
| 250 | 55802 | DCP1A |
| 251 | 9987 | HNRNPDL |
| 252 | 515 | ATP5F1 |
| 253 | 54788 | DNAJB12 |
| 254 | 55729 | ATF7IP |
| 255 | 9441 | MED26 |
| 256 | 1385 | CREB1 |
| 257 | 51538 | ZCCHC17 |
| 258 | 10914 | PAPOLA |
| 259 | 6827 | SUPT4H1 |
| 260 | 57148 | RALGAPB |

TABLE 31-continued

| Rank | ID | Gene symbol |
|---|---|---|
| 261 | 114883 | OSBPL9 |
| 262 | 8897 | MTMR3 |
| 263 | 9320 | TRIP12 |
| 264 | 54471 | SMCR7L |
| 265 | 10575 | CCT4 |
| 266 | 10569 | SLU7 |
| 267 | 55119 | PRPF38B |
| 268 | 7988 | ZNF212 |
| 269 | 79169 | C1orf35 |
| 270 | 10600 | USP16 |
| 271 | 3192 | HNRNPU |
| 272 | 6093 | ROCK1 |
| 273 | 7532 | YWHAG |
| 274 | 10367 | MICU1 |
| 275 | 6187 | RPS2 |
| 276 | 26130 | GAPVD1 |
| 277 | 129138 | ANKRD54 |
| 278 | 55109 | AGGF1 |
| 279 | 23471 | TRAM1 |
| 280 | 7385 | UQCRC2 |
| 281 | 9716 | AQR |
| 282 | 54826 | GIN1 |
| 283 | 27069 | GHITM |
| 284 | 10959 | TMED2 |
| 285 | 55000 | TUG1 |
| 286 | 6499 | SKIV2L |
| 287 | 5710 | PSMD4 |
| 288 | 8899 | PRPF4B |
| 289 | 23386 | NUDCD3 |
| 290 | 6603 | SMARCD2 |
| 291 | 5193 | PEX12 |
| 292 | 79728 | PALB2 |
| 293 | 55716 | LMBR1L |
| 294 | 9667 | SAFB2 |
| 295 | 9406 | ZRANB2 |
| 296 | 7555 | CNBP |
| 297 | 1398 | CRK |
| 298 | 91966 | CXorf40A |
| 299 | 51634 | RBMX2 |
| 300 | 54850 | FBXL12 |

TABLE 32

| Rank | ID | Gene symbol |
|---|---|---|
| 301 | 92335 | STRADA |
| 302 | 26056 | RAB11FIP5 |
| 303 | 7514 | XPO1 |
| 304 | 9797 | TATDN2 |
| 305 | 84261 | FBXW9 |
| 306 | 9202 | ZMYM4 |
| 307 | 3735 | KARS |
| 308 | 4659 | PPP1R12A |
| 309 | 8678 | BECN1 |
| 310 | 7528 | YY1 |
| 311 | 9255 | AIMP1 |
| 312 | 23219 | FBXO28 |
| 313 | 23759 | PPIL2 |
| 314 | 54455 | FBXO42 |
| 315 | 7248 | TSC1 |
| 316 | 11176 | BAZ2A |
| 317 | 27102 | EIF2AK1 |
| 318 | 400 | ARL1 |
| 319 | 728558 | ENTPD1-AS1 |
| 320 | 57448 | BIRC6 |
| 321 | 27072 | VPS41 |
| 322 | 56886 | UGGT1 |
| 323 | 7375 | USP4 |
| 324 | 51322 | WAC |
| 325 | 2597 | GAPDH |
| 326 | 4691 | LOC100996253 |
| 327 | 5976 | UPF1 |

TABLE 32-continued

| Rank | ID | Gene symbol |
|---|---|---|
| 328 | 10857 | PGRMC1 |
| 329 | 54918 | CMTM6 |
| 330 | 6155 | RPL27 |

Among the reference genes (control genes) equivalent to or more useful than β-actin thus obtained, SRSF3, TPM3, ZNF207, ZNF143, PUM1, RAB1A, and LOC101059961 included in the top ten genes by all of the methods were more useful reference genes in analyzing gene expression levels in squamous cell carcinoma. Particularly, the SRSF3 gene was the highest in all of the methods 1 to 3 and was the most useful reference gene.

[11] Subtype Classification Using Sets of Small Number of Genes

As described above, in the analyses by PCR and the like, it is desirable to limit the number of genes analyzed as small as possible. Hence, to verify that an evaluation of an efficacy of a chemoradiotherapy against squamous cell carcinoma was possible even by analyzing groups of a few genes, further gene probe screening was studied from the 163 gene probes (see Tables 8 to 12) useful in the subtype-5 classification and the 256 gene probes (see Tables 1 to 7) useful in the subtype-7 classification.

Figure 9:
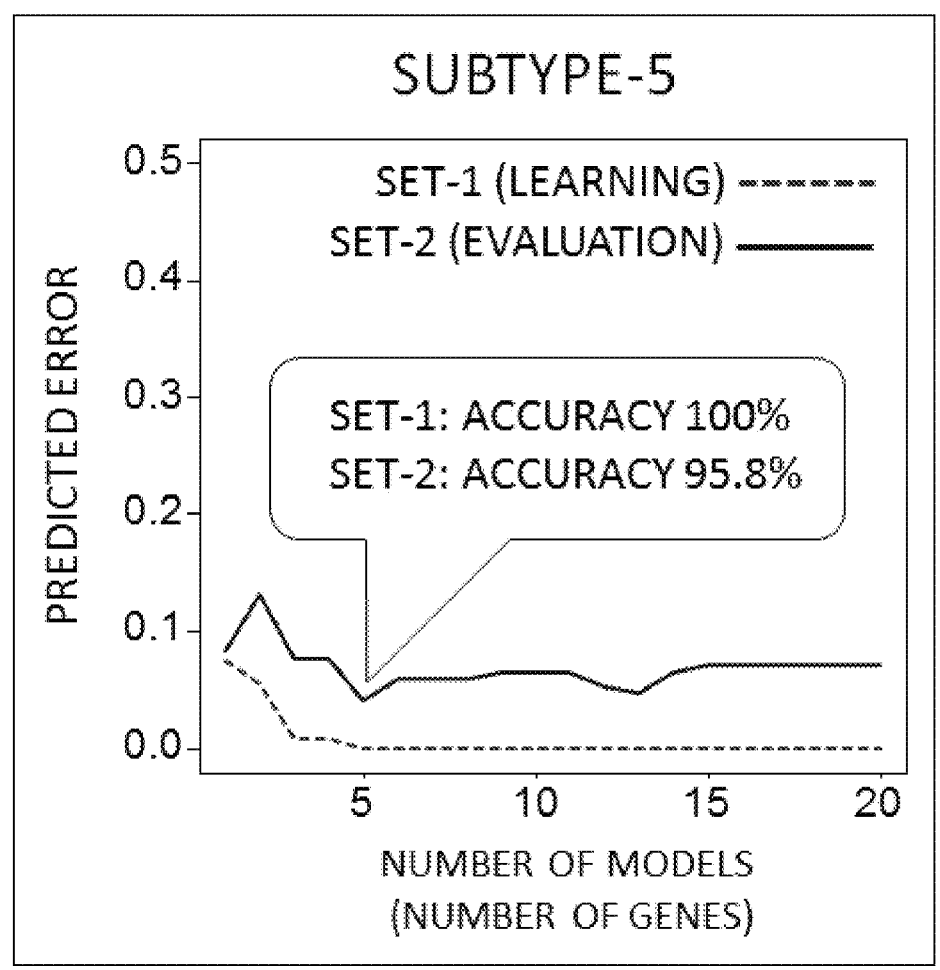
FIG. 9 is a graph for illustrating the result of analyzing, by a weighted majority voting determination method, predicted errors for subtype-5 in a 107-case set (set-1) for subtyping and a 167-case set (set-2) for validation with the number of genes analyzed being increased from 1 to 20 in total.
Figure 10:
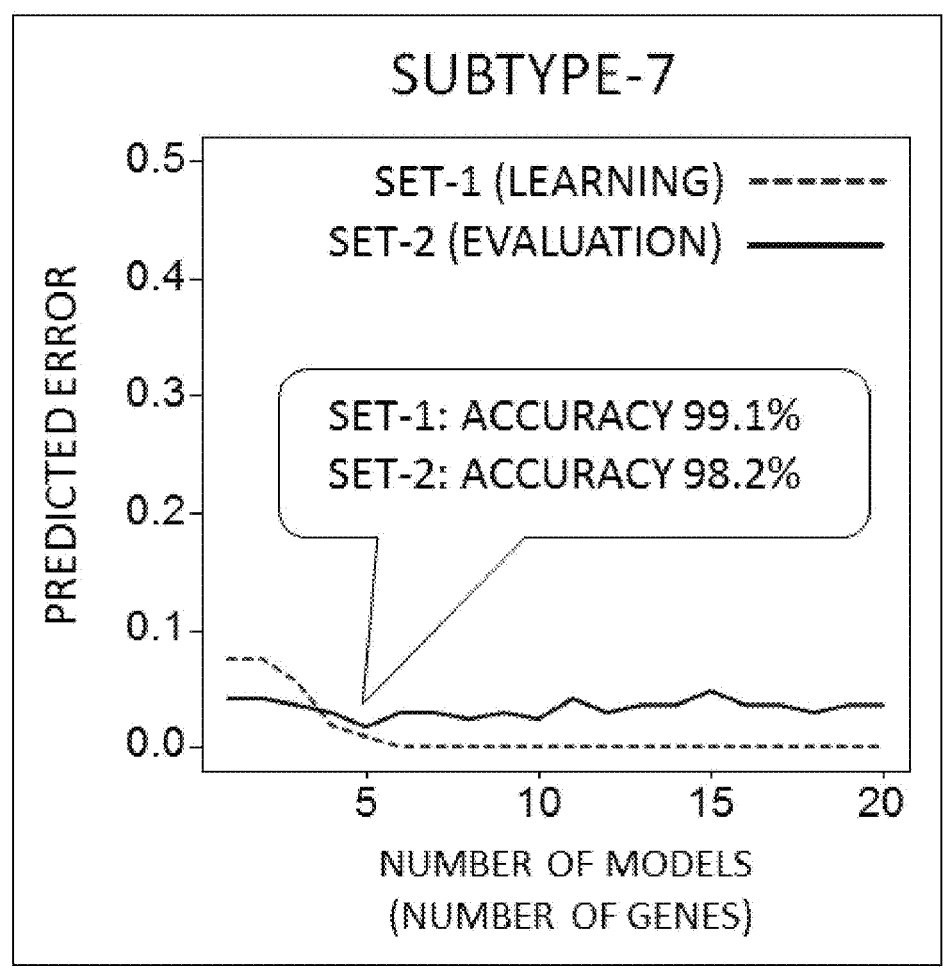
FIG. 10 is a graph for illustrating the result of analyzing, by the weighted majority voting determination method, predicted errors for subtype-7 in the set-1 and the set-2 with the number of genes analyzed being increased from 1 to 20 in total.

Concretely, boosting (weighted majority voting determination method), one of model construction procedures based on efficient gene combinations, was employed to select genes from the 107-case set for subtyping (aforementioned set-1) and evaluated by using the 167-case set for validation (aforementioned set-2). Moreover, in this event, the SRSF3 gene, which was the highest in all of the methods 1 to 3 in [10], was used as the reference gene. The study was conducted using a signal ratio obtained by dividing a signal value of each gene probe by a signal value of the SRSF3 gene. Note that boosting is a procedure to obtain a prediction result with a high precision by: efficiently selecting a simple prediction model, defining an appropriate weight, and determining a combination by weighted majority voting. In the present Examples, as the simple prediction model, a decision tree with a depth of 1 based on each gene was constructed. The number of models was increased from 1 to 20, and predicted errors in sets-1 and -2 were calculated for each subtype. The decision tree with a depth of 1 based on each gene herein was binarized based on a certain threshold of the signal ratio of each gene. FIG. 9 shows the result of the predicted errors of sets-1 and -2 for subtypes (-5, -7) obtained with the number of models being increased from 1 to 20 in total.

Figure 11:
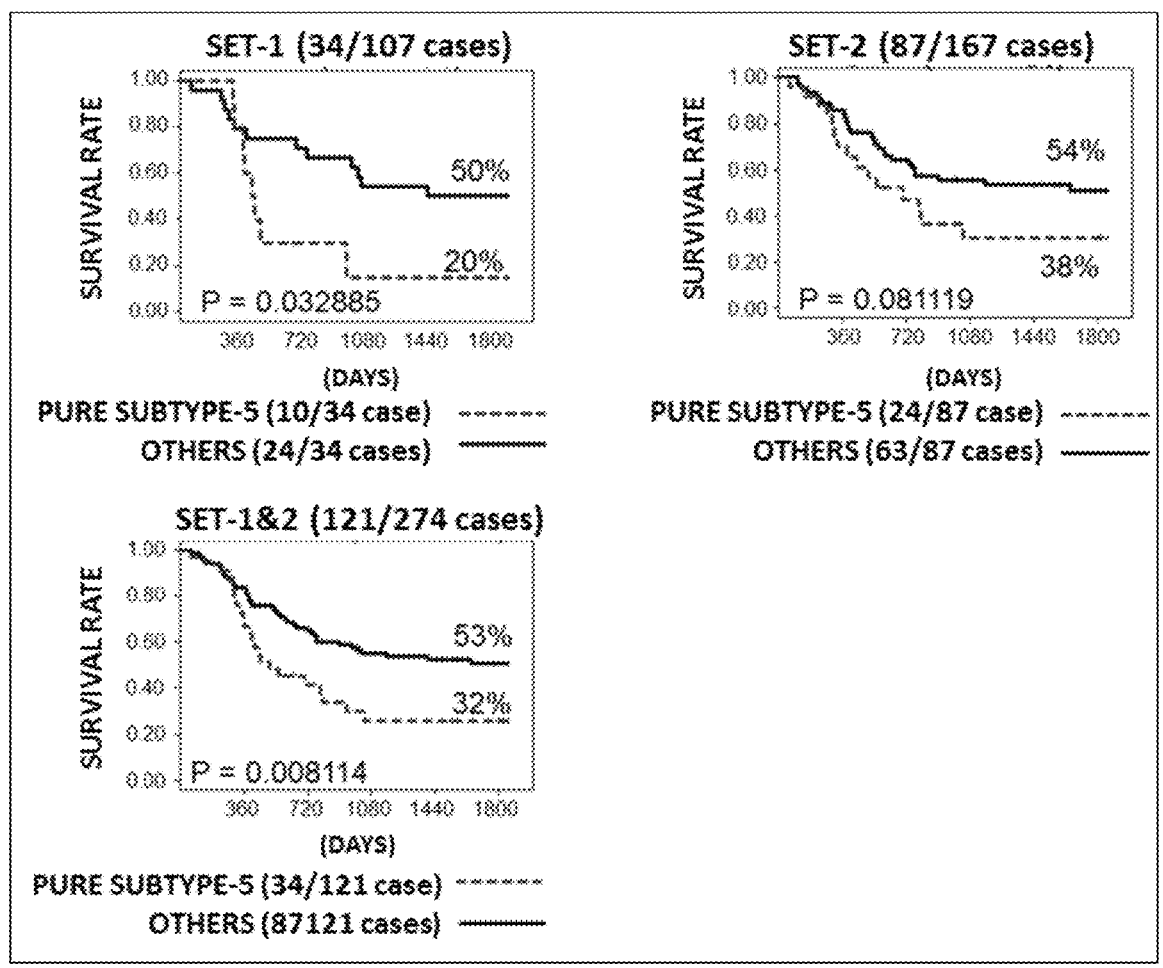
FIG. 11 shows graphs for illustrating a comparison of the survival rates after CRT between the squamous cell carcinoma patient group classified as pure subtype-5 and the other squamous cell carcinoma patient group, the comparison targeting the set-1 and the set-2, on the basis of expression levels of five genes (see Table 33) selected from a gene group defining subtype-5.
Figure 12:
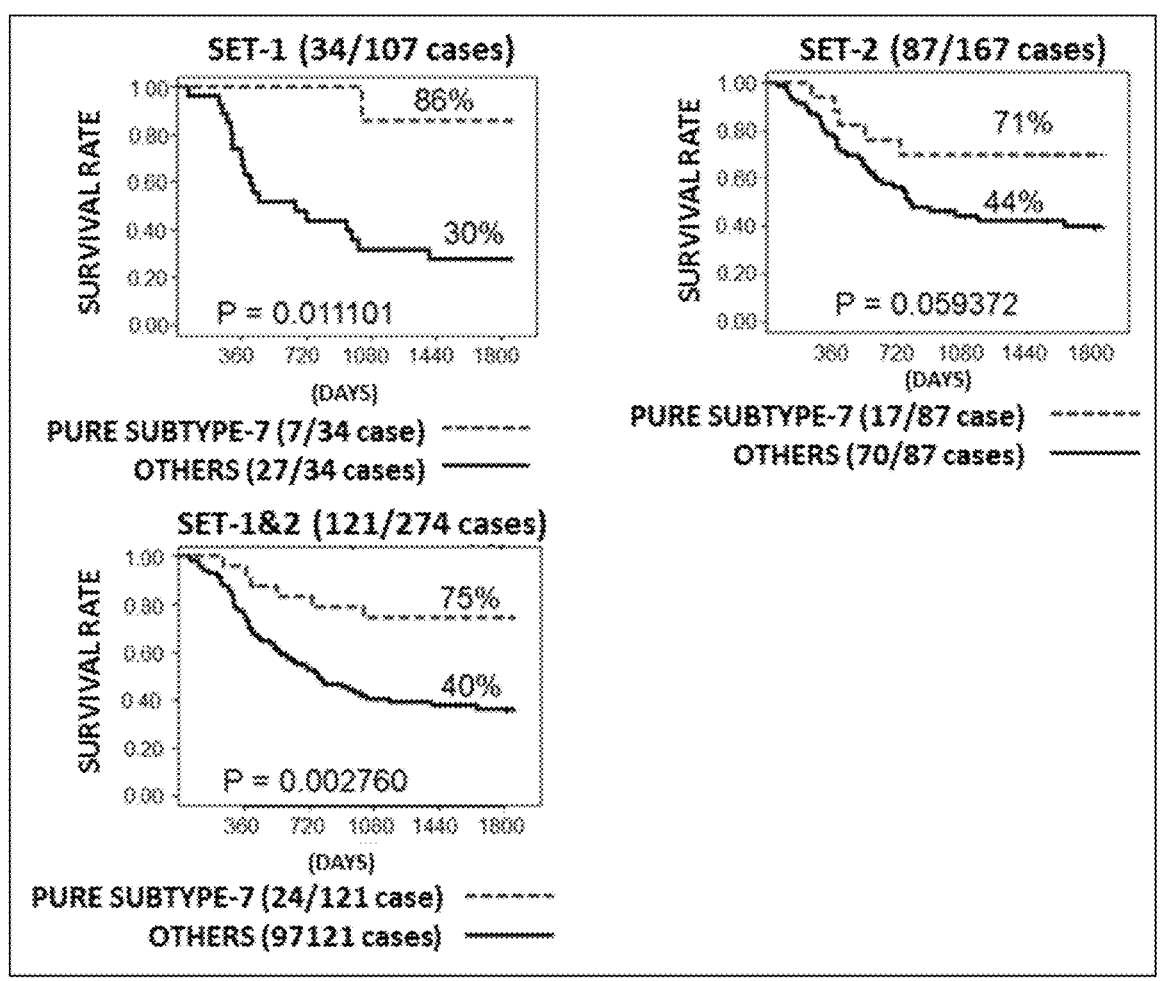
FIG. 12 shows graphs for illustrating a comparison of the survival rates after CRT between the squamous cell carcinoma patient group classified as pure subtype-7 and the other squamous cell carcinoma patient group, the comparison targeting the set-1 and the set-2, on the basis of expression levels of five genes (see Table 34) selected from a gene group defining subtype-7.

As shown in FIG. 9, even when the number of genes to be analyzed was 1, the predicted error was suppressed to approximately 0.1, verifying the usefulness of the genes according to the present invention. Moreover, in set-1 serving as the learning data, the predicted error was decreased as the number of models was increased. Meanwhile, in set-2 serving as the evaluation data, the error was minimum when the number of models was 5. Further, similar trends were obtained in the two-subtype predictions; when the number of models was 5, the accuracy was 95.8% for subtype-5, and the accuracy reached 98.2% for subtype-7. These verified that: it was possible to use common thresholds in set-1 and set-2; the SRSF3 gene was quite usable as the reference gene; and even a gene set of only five models enabled a prediction of each subtype with quite a high precision. Note that the five-model gene sets, the thresholds of the signal ratios thereof, and the weights of the models for the respective subtypes were as shown in Tables 33 and 34. Additionally, in Table 33, LOC344887 was selected twice in total. The same gene was redundantly selected because of the differences in the thresholds of the signal ratios and the weights of the models. Further, it was also verified as shown in FIGS. 11 and 12 that the survival analyses for pure subtypes-5 and -7 in this event were equivalent to the analysis using all of the 163 gene probes useful in the subtype-5 classification and the 256 gene probes useful in the subtype-7 classification.

TABLE 33

| Selected order | ID | Gene symbol | Signal ratio threshold | Weight of model |
|---|---|---|---|---|
| 1 | 344887 | LOC344887 | 0.131 | 1.258 |
| 2 | 4915 | NTRK2 | 0.152 | 1.503 |
| 3 | 89894 | TMEM116 | 0.125 | 1.286 |
| 4 | 28232 | SLCO3A1 | 0.135 | 0.982 |
| 5 | 344887 | LOC344887 | 0.089 | 0.908 |

TABLE 34

| Selected order | ID | Gene symbol | Signal ratio threshold | Weight of model |
|---|---|---|---|---|
| 1 | 6707 | SPRR3 | 2.111 | 1.258 |
| 2 | 634 | CEACAM1 | 0.013 | 0.795 |
| 3 | 5493 | PPL | 0.656 | 1.192 |
| 4 | 2327 | FMO2 | 0.105 | 1.321 |
| 5 | 26780 | SNORA68 | 0.050 | 0.945 |

[12] Evaluation and Ranking of Gene Sets by Re-Sampling

Figure 13:
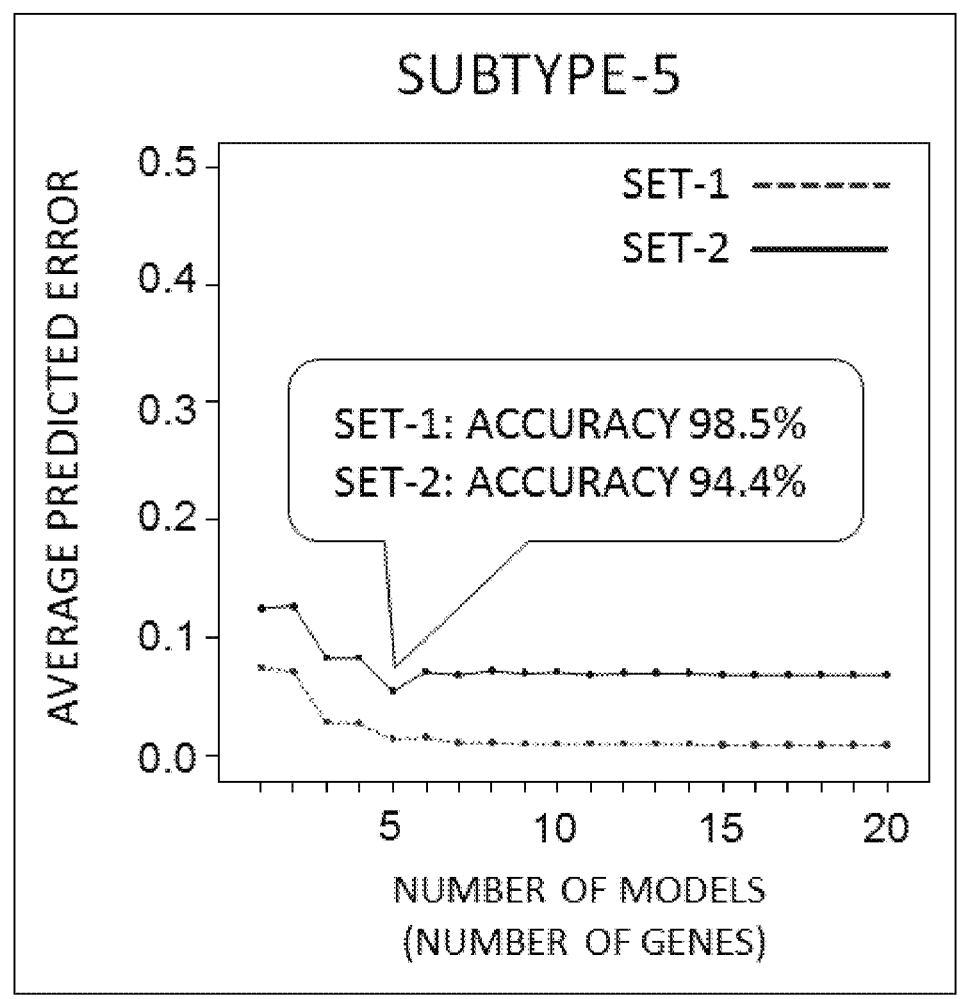
FIG. 13 is a graph for illustrating the result of performing re-samplings 1000 times from data on the cases of the set-1 for subtype-5 to construct models, followed by evaluations targeting the sets-1 and -2 by using these models (1 to 20 genes in total, selected by each re-sampling), and calculating average predicted errors.
Figure 14:
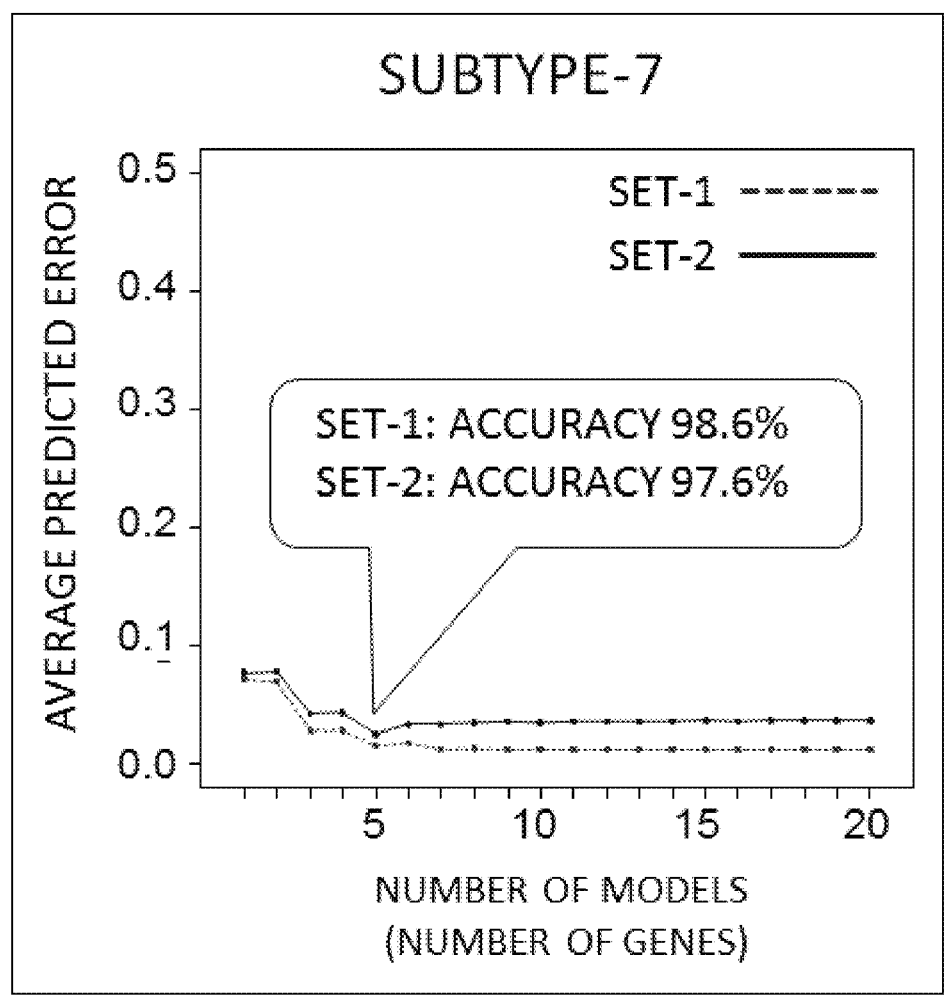
FIG. 14 is a graph for illustrating the result of performing the re-samplings 1000 times from data on the cases of the set-1 for subtype-7 to construct models, followed by evaluations targeting the sets-1 and -2 by using these models (1 to 20 genes in total, selected by each re-sampling), and calculating average predicted errors.

The preliminary studies in the aforementioned [11] and so on suggested the presences of a large number of useful sets of a few genes. Hence, re-samplings were performed 1000 times from data on the 107 cases of set-1 to select 200 cases while allowing redundancy. As a result of each re-sampling, models were constructed as learning data and evaluated by using sets-1 and -2. Average predicted errors were calculated based on the 1000 re-samplings. In addition, genes selected in five-model gene sets selected by each re-sampling were ranked according to the number of selections. The gene sets were selected from the 163 gene probes useful in the subtype-5 classification and the 256 gene probes useful in the subtype-7 classification. The number of selections was calculated such that even when different gene probes were selected, if the genes were the same, the number of selections was incremented. Then, in the 1000 re-samplings as described above, average values of predicted errors of sets-1 and -2 were calculated with the number of models from 1 to 20 in total. FIGS. 13 and 14 show the obtained result.

As apparent from the result shown in FIGS. 13 and 14, it was verified that, in the five-model gene set, the prediction accuracy of set-2 was maximum; more concretely, the average accuracy was 94.4% for subtype-5, and the accuracy reached 97.6% for subtype-7.

Moreover, when the genes included in the five-models by the 1000 re-samplings were summarized, the genes selected in the top groups varied. While 56 genes (see Table 35) were selected in subtype-5, 69 genes (see Table 36) were selected in subtype-7.

Thus, it was verified that, among the 163 genes (see Tables 8 to 12) useful in the subtype-5 classification and the 256 genes (see Tables 1 to 7) useful in the subtype-7 classification, the genes in Tables 35 and 36 were particularly useful genes in evaluating an efficacy of a chemoradiotherapy against squamous cell carcinoma.

TABLE 35

| Rank | Gene symbol | Number of selections |
|---|---|---|
| 1 | LOC344887 | 911 |
| 2 | NTRK2 | 841 |
| 3 | AKR1C1 | 652 |
| 4 | TMEM116 | 402 |
| 5 | SCN9A | 352 |
| 6 | NRCAM | 260 |
| 7 | SAMD12 | 252 |
| 8 | JAKMIP3 | 227 |
| 9 | CCL26 | 145 |
| 10 | MRAP2 | 84 |
| 11 | FAXC | 79 |
| 12 | SOX2-OT | 76 |
| 13 | GCLC | 61 |
| 14 | SLC35G1 | 58 |
| 15 | AKR1C3 | 56 |
| 16 | SLCO3A1 | 51 |
| 17 | ABCC5 | 50 |
| 18 | ABCC1 | 49 |
| 19 | GPX2 | 45 |
| 20 | ARHGEF26-AS1 | 39 |
| 20 | SLC16A14 | 39 |
| 22 | ARHGEF26 | 38 |
| 23 | ADAM23 | 24 |
| 23 | SOX2 | 24 |
| 25 | ALDH1A1 | 22 |
| 26 | SEMA6D | 20 |
| 27 | FOXE1 | 17 |
| 28 | CYP26A1 | 15 |
| 29 | LRRC4 | 13 |
| 29 | SOST | 13 |
| 31 | COLGALT2 | 9 |
| 31 | PAK7 | 9 |
| 33 | MPP3 | 8 |
| 34 | B4GALT4 | 7 |
| 34 | CLDN20 | 7 |
| 36 | CACNA1B | 6 |
| 36 | GSTM3 | 6 |
| 38 | NTS | 4 |
| 38 | TXNRD1 | 4 |
| 40 | CDK5RAP2 | 3 |
| 40 | GSR | 3 |
| 42 | ENTPD3 | 2 |
| 42 | GPC3 | 2 |
| 42 | LOC100505633 | 2 |
| 42 | SLC4A11 | 2 |
| 46 | AADACL2 | 1 |
| 46 | BDNF | 1 |
| 46 | CHODL | 1 |
| 46 | CHST7 | 1 |
| 46 | CYP4F3 | 1 |
| 46 | GDA | 1 |
| 46 | GSTA1 | 1 |
| 46 | NEDD4L | 1 |
| 46 | RAB3B | 1 |
| 46 | SLC47A1 | 1 |
| 46 | UPK1B | 1 |

TABLE 36

| Rank | Gene symbol | Number of selections |
|---|---|---|
| 1 | FMO2 | 978 |
| 2 | PPL | 703 |
| 3 | SPRR3 | 573 |
| 4 | CD24 | 529 |
| 5 | SPINK5 | 272 |
| 6 | TGM1 | 192 |
| 7 | SERPINB1 | 150 |
| 8 | SCEL | 138 |
| 9 | S100A14 | 134 |
| 10 | RHCG | 133 |
| 11 | IL1RN | 111 |
| 12 | MPZL2 | 100 |
| 13 | CRNN | 75 |
| 14 | C1orf177 | 72 |
| 15 | KRT13 | 64 |
| 16 | CRABP2 | 51 |
| 17 | C2orf54 | 48 |
| 17 | LYNX1 | 48 |
| 17 | SNORA68 | 48 |
| 20 | LOC441178 | 47 |
| 21 | CLIC3 | 46 |
| 22 | GBP6 | 44 |
| 23 | AQP3 | 36 |
| 24 | EPS8L1 | 35 |
| 25 | A2ML1 | 33 |
| 25 | PITX1 | 33 |
| 27 | ENDOU | 30 |
| 28 | CYP2C18 | 28 |
| 29 | BLNK | 25 |
| 30 | SLURP1 | 21 |
| 31 | C21orf15 | 20 |
| 31 | ZNF185 | 20 |
| 33 | ANXA1 | 17 |
| 34 | C9orf169 | 15 |
| 35 | MAL | 11 |
| 36 | CXCR2 | 10 |
| 36 | ECM1 | 10 |
| 36 | TMPRSS11B | 10 |
| 39 | GALR3 | 9 |
| 39 | PRSS27 | 9 |
| 41 | SLC16A7 | 6 |
| 42 | ARHGAP32 | 5 |
| 42 | BNIPL | 5 |
| 42 | GDPD3 | 5 |
| 42 | SPRR1A | 5 |
| 46 | KLK13 | 4 |
| 46 | TMPRSS11D | 4 |
| 48 | MGLL | 3 |
| 48 | PLEKHA7 | 3 |
| 48 | RAB25 | 3 |
| 48 | TRNP1 | 3 |
| 52 | ANKRD20A11P | 2 |
| 52 | CAPN5 | 2 |
| 52 | CEACAM1 | 2 |
| 52 | CEACAM7 | 2 |
| 52 | EHF | 2 |
| 52 | IKZF2 | 2 |
| 52 | KRT78 | 2 |
| 52 | PPP1R3C | 2 |
| 60 | ATP13A4 | 1 |
| 60 | CLCA4 | 1 |
| 60 | CSTB | 1 |
| 60 | FAM3D | 1 |
| 60 | NMU | 1 |
| 60 | PRSS2 | 1 |
| 60 | PTK6 | 1 |
| 60 | SPAG17 | 1 |
| 60 | SPRR2C | 1 |
| 60 | TMPRSS11E | 1 |

INDUSTRIAL APPLICABILITY

As has been described above, the present invention makes it possible to evaluate an efficacy of a chemoradiotherapy against squamous cell carcinoma on the basis of an expression level of at least one gene selected from the SIM2 co-expression gene group. Further, it is also possible to evaluate the efficacy with a higher precision on the basis of an expression level of at least one gene selected from the FOXE1 co-expression gene group.

Thus, the evaluation method of the present invention and the agent used in the method are quite effective in determining a therapeutic strategy against squamous cell carcinoma.

SEQUENCE LISTING FREE TEXT

SEQ ID NOs: 1 to 20
<223> Artificially synthesized primer sequence

The invention claimed is:

1. A method of measuring gene expression in a squamous cell carcinoma, the method comprising:
   detecting expression levels of at least two genes selected from a SIM2 gene and genes co-expressed with the SIM2 gene in a squamous cell carcinoma specimen isolated from a subject, wherein the genes co-expressed with the SIM2 gene are genes correlated with the expression of the SIM2 gene with a Pearson product-moment correlation coefficient of 0.4 or more.

2. A method for evaluating an efficacy of a chemoradiotherapy against squamous cell carcinoma, the method comprising the following steps (a) to (c):
   (a) detecting expression levels of at least five genes selected from a SIM2 gene and genes co-expressed with the SIM2 gene in a squamous cell carcinoma specimen isolated from a subject;
   (b) comparing the expression levels detected in step (a) with reference expression levels of the corresponding genes; and
   (c) determining that an efficacy of a chemoradiotherapy against squamous cell carcinoma in the subject is high if the expression levels in the subject are higher than the reference expression levels as a result of the comparison in step (b),
   wherein the genes co-expressed with the SIM2 gene are genes correlated with the expression of the SIM2 gene with a Pearson product-moment correlation coefficient of 0.4 or more.

3. A method for evaluating an efficacy of a chemoradiotherapy against squamous cell carcinoma, the method comprising the following steps (a) to (c):
   (a) detecting an expression level of at least one gene selected from a SIM2 gene and genes co-expressed with the SIM2 gene as well as an expression level of at least one gene selected from a FOXE1 gene and genes co-expressed with the FOXE1 gene in a squamous cell carcinoma specimen isolated from a subject;
   (b) comparing the expression levels detected in step (a) with reference expression levels of the corresponding genes, respectively; and
   (c) determining that an efficacy of a chemoradiotherapy against squamous cell carcinoma in the subject is high if the expression level of the at least one gene selected from a SIM2 gene and genes co-expressed with the SIM2 gene in the subject is higher than the reference expression level thereof and the expression level of the at least one gene selected from a FOXE1 gene and genes co-expressed with the FOXE1 gene in the subject is lower than the reference expression level thereof as a result of the comparison in step (b).

4. A method for treating squamous cell carcinoma in a subject, the method comprising the following steps (a) to (d):
   (a) detecting an expression level of at least one gene selected from a SIM2 gene and genes co-expressed with the SIM2 gene in a squamous cell carcinoma specimen isolated from a subject;
   (b) comparing the expression level detected in step (a) with a reference expression level of the corresponding gene;
   (c) determining that an efficacy of a chemoradiotherapy against squamous cell carcinoma in the subject is high if the expression level in the subject is higher than the reference expression level as a result of the comparison in step (b); and
   (d) performing a chemoradiotherapy on the subject who is determined that an efficacy of a chemoradiotherapy against squamous cell carcinoma is high in step (c), or performing a therapy for removing squamous cell carcinoma by a surgical operation or an endoscopic operation, or a therapy for removing squamous cell carcinoma by laser beam irradiation, on the subject who is determined that an efficacy of a chemoradiotherapy against squamous cell carcinoma is not high in step (c).

5. A method for treating squamous cell carcinoma in a subject, the method comprising the following steps (a) to (d):
   (a) detecting an expression level of at least one gene selected from a SIM2 gene and genes co-expressed with the SIM2 gene as well as an expression level of at least one gene selected from a FOXE1 gene and genes co-expressed with the FOXE1 gene in a squamous cell carcinoma specimen isolated from a subject;
   (b) comparing the expression levels detected in step (a) with reference expression levels of the corresponding genes, respectively;
   (c) determining that an efficacy of a chemoradiotherapy against squamous cell carcinoma in the subject is high if the expression level of the at least one gene selected from a SIM2 gene and genes co-expressed with the SIM2 gene in the subject is higher than the reference expression level thereof and the expression level of the at least one gene selected from a FOXE1 gene and genes co-expressed with the FOXE1 gene in the subject is lower than the reference expression level thereof as a result of the comparison in step (b); and
   (d) performing a chemoradiotherapy on the subject who is determined that an efficacy of a chemoradiotherapy against squamous cell carcinoma is high in step (c), or performing a therapy for removing squamous cell carcinoma by a surgical operation or an endoscopic operation, or a therapy for removing squamous cell carcinoma by laser beam irradiation, on the subject who is determined that an efficacy of a chemoradiotherapy against squamous cell carcinoma is not high in step (c).

6. A kit for measuring gene expression in a squamous cell carcinoma by the method according to claim 5 and evaluating an efficacy of a chemoradiotherapy against squamous cell carcinoma, the kit comprising at least two oligonucleotides selected from the following (a) and/or at least two antibodies selected from the following (b):

(a) an oligonucleotide having a length of at least 15 nucleotides and being capable of hybridizing to a transcription product of at least one gene selected from a SIM2 gene and genes co-expressed with the SIM2 gene or a complementary nucleic acid to the transcription product; and (b) an antibody capable of binding to a translation product of at least one gene selected from a SIM2 gene and genes co-expressed with the SIM2 gene, wherein the genes co-expressed with the SIM2 gene are genes correlated with the expression of the SIM2 gene with a Pearson product-moment correlation coefficient of 0.4 or more.

* * * * *

```
                        SEQUENCE LISTING

<160> NUMBER OF SEQ ID NOS: 20

<210> SEQ ID NO 1
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 1
cttccctctg gactctcacg                                                   20

<210> SEQ ID NO 2
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 2
aggctgtgcc tagcagtgtt                                                   20

<210> SEQ ID NO 3
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 3
tggccactgg atactgaaca                                                   20

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 4
cccaaatcca tcctcaaatg                                                   20

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonuceltide primer sequence

<400> SEQUENCE: 5
tgactccagg aaccagcgaa g                                                 21

<210> SEQ ID NO 6
<211> LENGTH: 23
<212> TYPE: DNA
<213> ORGANISM: Artificial Sequence
<220> FEATURE:
<223> OTHER INFORMATION: Synthetic oligonuceltide primer sequence

<400> SEQUENCE: 6
gcgaatgcct gttacactgt tga                                               23
```

-continued

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 7
gaagtccctt gccatcctaa                                          20

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 8
gcacgaaggc tcatcattca                                          20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 9
agactctgac cagagatcga                                          20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 10
ggtggacagt ttcatgaagc                                          20

<210> SEQ ID NO 11
<211> LENGTH: 24
<212> TYPE: DNA
<213> ORGANISM: Artificial Sequence
<220> FEATURE:
<223> OTHER INFORMATION: Synthetic oligonuceltide primer sequence

<400> SEQUENCE: 11
ggagattctg ggtcaagtaa tgtt                                     24

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 12
tgtgctagcc ctgatgttga                                          20

<210> SEQ ID NO 13
<211> LENGTH: 20
<212> TYPE: DNA
<213> ORGANISM: Artificial Sequence
<220> FEATURE:

<223> OTHER INFORMATION: Synthetic oligonuceltide primer sequence

<400> SEQUENCE: 13
accggagaaa agagctatgg                                              20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 14
tggggagttt aagacctctc                                              20

<210> SEQ ID NO 15
<211> LENGTH: 21
<212> TYPE: DNA
<213> ORGANISM: Artificial Sequence
<220> FEATURE:
<223> OTHER INFORMATION: Synthetic oligonuceltide primer sequence

<400> SEQUENCE: 15
tacttcagat gcgatggcta c                                            21

<210> SEQ ID NO 16
<211> LENGTH: 21
<212> TYPE: DNA
<213> ORGANISM: Artificial Sequence
<220> FEATURE:
<223> OTHER INFORMATION: Synthetic oligonuceltide primer sequence

<400> SEQUENCE: 16
ctgagttcag gaaataggag a                                            21

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 17
gctttcaagt gcctttctgc                                              20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 18
gttggttgga tacttgctgg                                              20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 19
agctctagac aaccctgcaa                                              20

```
<210> SEQ ID NO 20
<211> LENGTH: 20
<212> TYPE: DNA
<213> ORGANISM: Artificial Sequence
<220> FEATURE:
<223> OTHER INFORMATION: Synthetic oligonuceltide primer sequence

<400> SEQUENCE: 20
agggttccat ctcagctcaa                                              20
```